US008354228B2

(12) United States Patent
Ron

(10) Patent No.: US 8,354,228 B2
(45) Date of Patent: Jan. 15, 2013

(54) HUMAN SEF ISOFORMS AND METHODS OF USING SAME FOR CANCER DIAGNOSIS AND GENE THERAPY

(75) Inventor: Dina Ron, Kiryat-Tivon (IL)

(73) Assignee: Technion Research & Development Foundation Ltd., Haifa (IL)

( * ) Notice: Subject to any disclaimer, the term of this patent is extended or adjusted under 35 U.S.C. 154(b) by 0 days.

(21) Appl. No.: 12/591,960

(22) Filed: Dec. 7, 2009

(65) Prior Publication Data

US 2010/0093840 A1 Apr. 15, 2010

Related U.S. Application Data

(63) Continuation of application No. 11/493,608, filed on Jul. 27, 2006, now Pat. No. 7,629,325, which is a continuation-in-part of application No. 10/963,439, filed on Oct. 11, 2004, now abandoned.

(51) Int. Cl.
*C12Q 1/68* (2006.01)

(52) U.S. Cl. ........................................................ 435/6.1

(58) Field of Classification Search ........................ None
See application file for complete search history.

(56) References Cited

U.S. PATENT DOCUMENTS

2004/0235104 A1* 11/2004 Yang ............................ 435/69.1
2004/0260389 A1 12/2004 Case et al.
2004/0265834 A1 12/2004 Xiong et al.
2006/0079444 A1 4/2006 Ron
2006/0293240 A1 12/2006 Ron

OTHER PUBLICATIONS

Alberts et al. (Molecular Biology of the Cell, 3rd edition, 1994, p. 465).*
Greenbaum et al. (Genome Biology, 2003, vol. 4, Issue 9, pp. 117.1-117.8).*
Yang et al (JBC, 2003, 278(35): 33232-33238).*
Darby et al (Oncogene, 2006, 25:4122-4127).*
Hanks et al (Int J Radiat Oncol Biol Phys, 1988, 14(2): Abstract).*
Hanks et al (Int J Radiat Oncol Biol Phys, 1988, 14(2): 243-248).*
Tockman et al (Cancer Res., 1992, 52:2711s-2718s).*
Official Action Dated May 2, 2007 From the US Patent and Trademark Office Re.: U.S. Appl. No. 11/493,608.
Official Action Dated Oct. 7, 2008 From the US Patent and Trademark Office Re.: U.S. Appl. No. 11/493,608.
Official Action Dated Nov. 17, 2006 From the US Patent and Trademark Office Re.: U.S. Appl. No. 11/493,608.
Official Action Dated Jan. 27, 2006 From the US Patent and Trademark Office Re.: U.S. Appl. No. 10/963,439.
Official Action Dated Jun. 30, 2005 From the US Patent and Trademark Office Re.: U.S. Appl. No. 10/963,439.
Kitsberg et al. "Keratinocyte Growth Factor Induces Mammary and Prostatic Hyperplasia and Mammary Adenocarcinoma in Transgenic Mice", Oncogene, 13, p. 2507-2515, 1996.
Kovalenko et al. "Sef Inhibits Fibroblast Growth Factor Signaling by Inhibiting FGFR1 Tyrosine Phosphorylation and Subsequent ERK Activation", J. Biol. Chem., vol. 278 (16) p. 14087-14091, 2003.
Lin et al. "Cloning of the Mouse Sef Gene and Comparative analysis of its Expression with Fgf8 and Spry2 During Embryogenesis", Mech. Dev. 113, 163-168, 2002.
Mahendra et al. "Antiangiogenic Cancer Gene Therapy by Adeno-Associated Virus 2-Mediated Stable Expression of the Soluble FMS-Like Tyrosine Kinase-1 Receptor", Cancer Gene Therapy, 12: 26-34, 2005. Abstract.
MCKeehan et al. "The Heparan Sulfate-Fibroblast Growth Factor Family: Diversity of Structure and Function", Medline, Prog. Nucleic Acid. Res. Mol. Biol, vol. 59 p. 135-176, 1998. Abstract.
Rolland "Gene Medicines: The End of the Beginning", Advanced Drug Delivery Reviews, 57: 669-673, 2005.
Shaoul et al. "Fibroblast Growth Factor Receptors Display Both Common and Distinct Signaling Pathways", Oncogene, 10: 1553-1561, 1995.
Siddiqi et al. "Increased Expression of Keratinocyte Growth Factor in Human Pancreatic Cancer", Biochemical and Biophysical Reaserch Communications, vol. 215 (1): p. 309-315, 1995.
Siegfried et al. "Distinct Patterns of Expression of Keratinocyte Growth Factor and its Receptor in Endometrial Carcinoma",Cancer vol. 79 p. 1166-1171, 1997.
Tsang et al. "Identification of Sef, a Novel Modulator of FGF Signalling", Nature Cell Biology, vol. 4, 2002.
Visco et al. "Expression of Keratinocyte Growth Factor Receptor Compared with that of Epidermal Growth Factor Receptor and erbB-2 in Endometrial Adenocarcinoma", International Journal of Oncology, vol. 15, p. 431-435, 1999.
Xiong et al. "hSef Inhibits PC-12 Cell Differentiation by Interfering With Ras-Mitogen-Activated Protein Kinase MAPK Signaling", Journal of Biological Chemistry, vol. 258 (50): p. 50273-50282, 2003.
Yang et al. "A Novel Interleukin-17 Recptor-Like protein Idetified in Human Umbilical Vein Endothelial Cells Antagonizes Basic Fibroblast Growth Factor-Induced signaling", Journal of Biol. Chem., vol. 278 (35), p. 33232-8, 2003.
Zetter "Angiogenesis and Tumor Metastasis", Annual Reveiw of Medicine vol. 409: p. 407-424, 1998.
Zisman-Rozen et al. "Downregulation of sef, an Inhibitor of Receptor Tyrosine Kinase Signaling, is Common to a Variety of Human Carcinomas", oncogene, vol. 26: p. 6093-6098, 2007.

(Continued)

*Primary Examiner* — Sean Aeder

(57) ABSTRACT

A method and pharmaceutical compositions useful for inhibiting the growth of solid tumors are provided. Specifically, the method is effected by administering to a subject in need thereof an agent capable of upregulating the expression level and/or activity of at least a functional portion of Sef, wherein the functional portion being capable of inhibiting RTK-mediated cell proliferation. Also provided are methods and kits for diagnosing and staging of cancer by detecting the expression level of hSef in a tissue sample, wherein a decrease in hSef expression level is indicative of cancer.

14 Claims, 18 Drawing Sheets
(6 of 18 Drawing Sheet(s) Filed in Color)

OTHER PUBLICATIONS

Murphy et al. "Evidence for Distinct Alterations in the FGF Axis in Prostate Cancer Progression to an Aggressive Clinical Phenotype", Accepted Article for The Journal of Pathology, 220(4): 452-460, Mar. 2010.

Official Action Dated Jan. 10, 2008 From the US Patent and Trademark Office Re.: U.S. Appl. No. 11/493,608.

Notice of Allowance Dated Jul. 30, 2009 From the US Patent and Trademark Office Re.: U.S. Appl. No. 11/493,608.

Official Action Dated Apr. 3, 2009 From the US Patent and Trademark Office Re.: U.S. Appl. No. 11/493,608.

Dermer "Another Anniversary for the War on Cancer", Bio/Technology, 12: 320, 1994.

Freshney "Culture of Animal Cells—A Manual of Basic Technique", Alan R. Lyss Inc. NY, p. 3-4, 1983.

Guan et al. "Successful Management of Postoperative Recurrence of Hepatocellular Carcinoma With P53 Gene Therapy Combining Transcatheter Arterial Chemoembolization", World Journal of Gastroenterology, 11: 3803-3805, 2005.

Gura "Systems for Identifying New Drugs Are Often Faulty", Science, 278: 1041-1042, 1997.

Lang et al. "Phase I Trial of Adenovirus-Mediated P53 Gene Therapy for Recurrent Glioma: biological and Clinical Results", Journal of Clinical Oncology, 21(13): 2508-2518, 2003.

Murphy et al. "Evidence for Distinct Alterations in the FGF Axis in Prostate Cancer Progression to an Aggressive Clinical Phenotype", Acepted Article for The Journal of Pathology, 220(4): 452-460, Mar. 2010.

Toru et al. "Expression cDNA Cloning of the KGF Receptor by Creation of a Trasforming Autocrine Loop", Science, vol. 251, p. 72-75, 1991.

Yang et al. "A Novel Interleukin-17 Receptor-Like Protein Identified in Human Umbilical Vein Endothelial Cells Antagonizes Basic Fibroblast Growth Factor-Induced Signaling", The Journal of Biological Chemistry, 278(35): 33232-33238, Aug. 29, 2003.

* cited by examiner

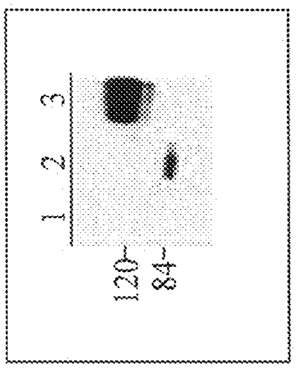
Figure 2a
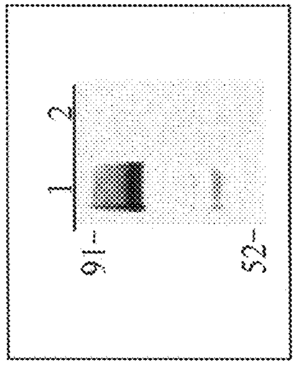
Figure 2b
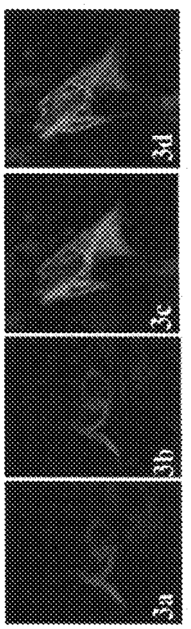
Figures 3a-d

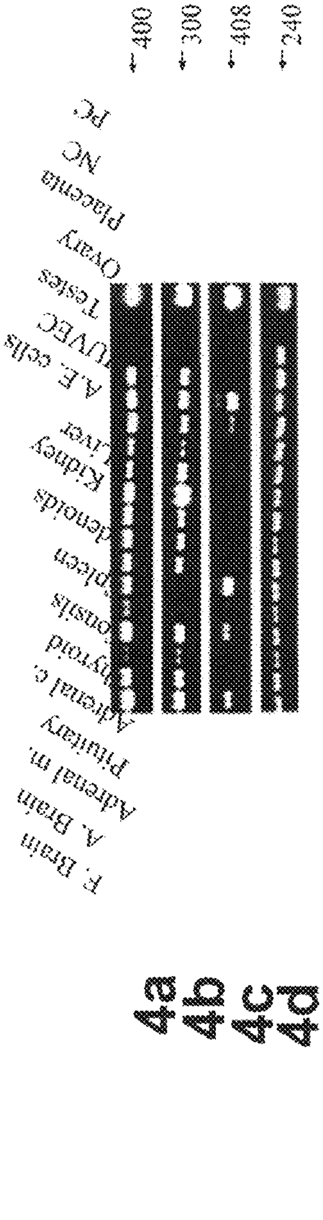
Figures 4a-d

TGAAGCGGGCAGAAAGAGTGGTGGATGATGTCCGGGGACTGGCATGA

CCCTGGGTCTCAGCAGTGCTGCTTGCATTTGGACTCCATGGGGCTTTGT

GTTGGAAGAGCAAATTGGCTTCACTCTGCATCATGTTCTCTTGTTTTCC

CACAGGGAGTGGGGCCAGCCAGCAGAAACAGTGGGCTGTACAACATC

ACCTTCAAATATGACAATTGTACCACCTACTTGAATCCAGTG

Figure 13a

*SGQKEWWMMSGDWHDPGSQQCCLHLDSMGLCVGRANWLHSASCSLV

FPQGVGPASRNSGLYNITFKYDNCTTYLNPV

Figure 13b

CGCCAACCTGTCTGCTCTTCGCGGGGTCCGCGGCCGGCCTGGGTCTCAC
TCCTCCCGCGCATCCTCCTGGTTTCCCTCCCCGGACGCGTGTCCTCCGG
CCCTGGCCGAGATGAAAGCGGCTGCCCGACCCCGGCTTTGTGTTGCTA
ATGAGGGAGTGGGGCCAGCCAGCAGAAACAGTGGGCTGTACAACATC
ACCTTCAAATATGACAATTGTACCACCTACTTGAATCCAGTG

Figure 14a

ANLSALRGVRGRPGSHSSRASSWFPSPDACPPALAEMKAAARPRLCVANE
GVGPASRNSGLYNITFKYDNCTTYLNPV

Figure 14b

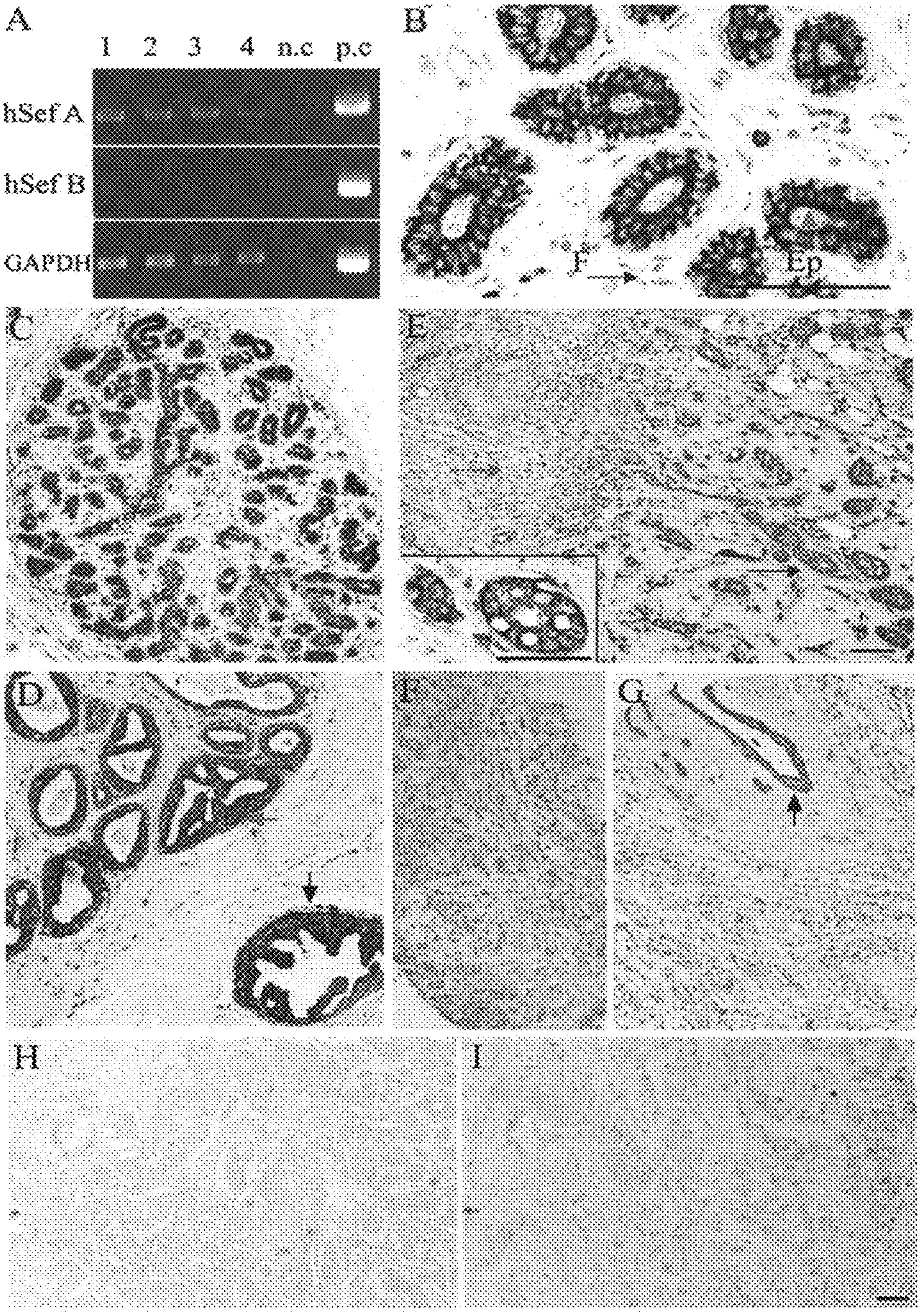
Figures 15a-i

Figures 16a-f
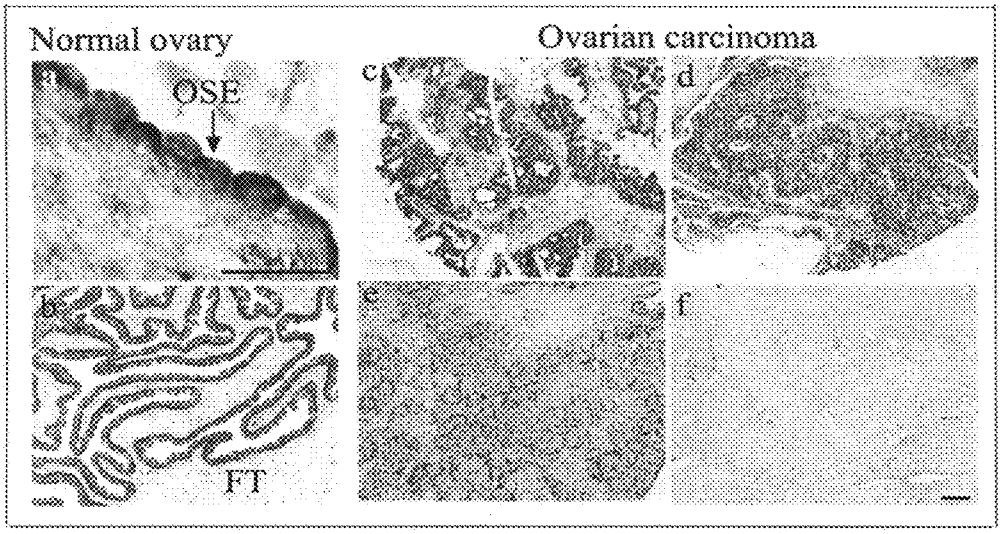
Figures 17a-f
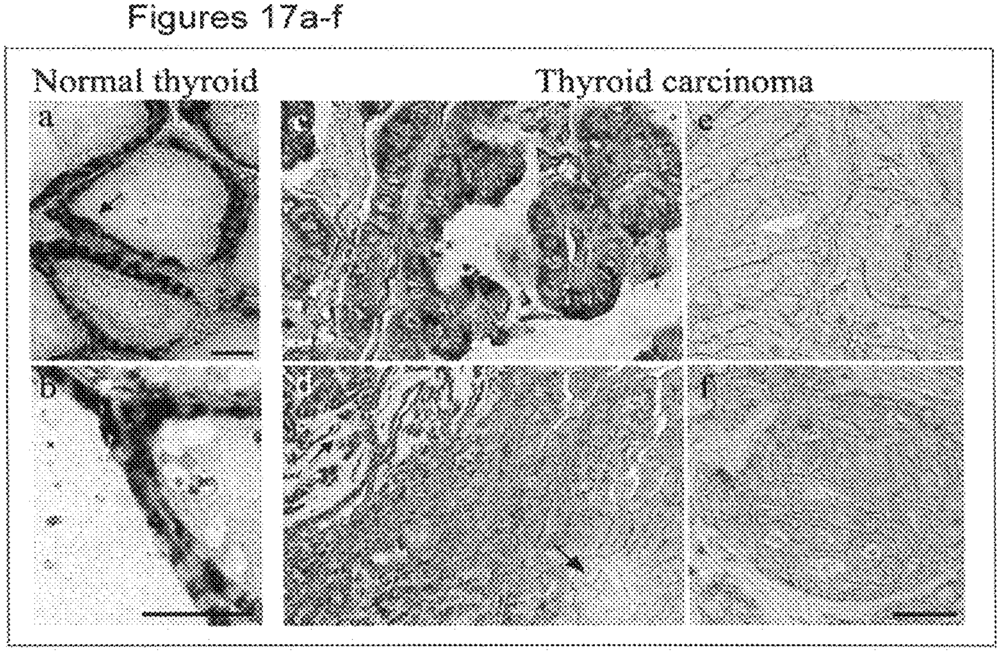

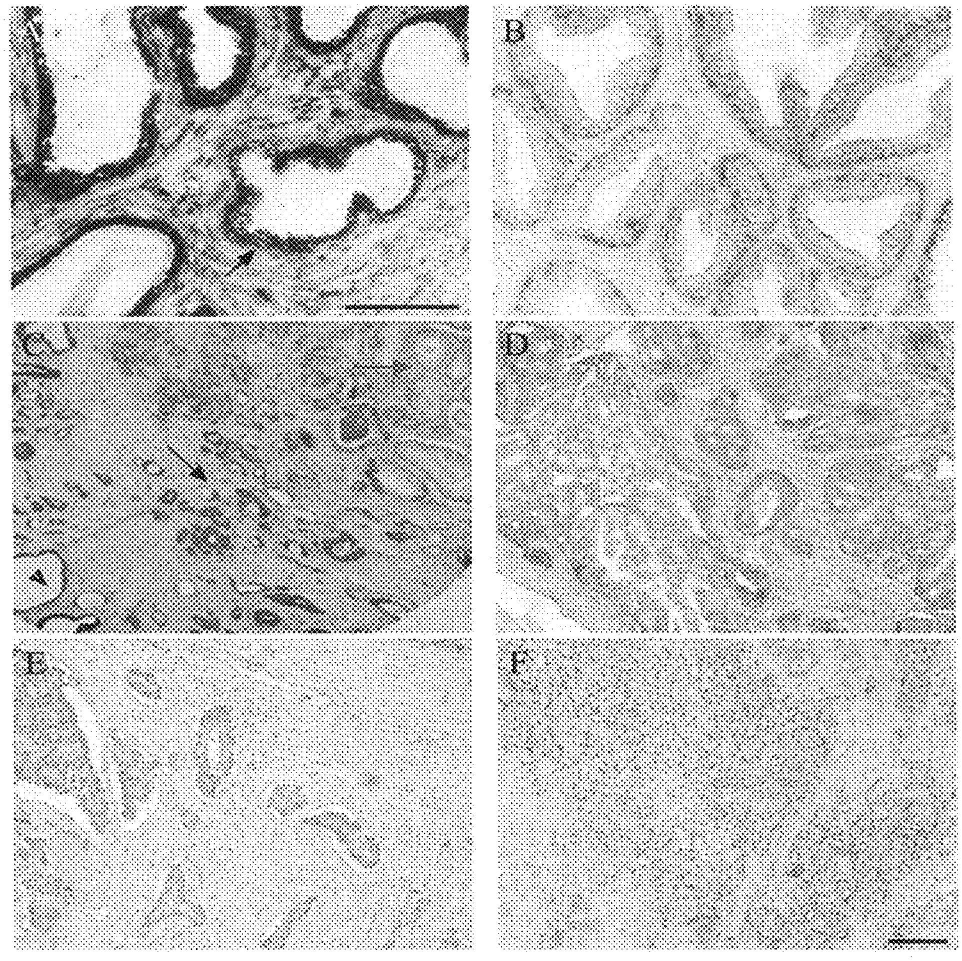
Figures 18a-f

SEQUENCE LISTING

<160> NUMBER OF SEQ ID NOS: 31

<210> SEQ ID NO 1
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 1
agtggcaatg cttagactct ttcgt 25

<210> SEQ ID NO 2
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 2
gcgtgccaga cagagtgcta ggcat 25

<210> SEQ ID NO 3
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 3
gaggatccaa gctttgttac aaaggggcga ccgcgt 36

<210> SEQ ID NO 4
<211> LENGTH: 2214
<212> TYPE: DNA
<213> ORGANISM: Homo sapiens

<400> SEQUENCE: 4
gcgtgccaga cagagtgcta ggcatggggg cagaggtgaa tcagatgaca gccacctctc 60
accacgagga gtggctgaaa gtgtgactgg actacaggca atcctggcct tggcagggag 120
tggggccagc cagcagaaac agtgggctgt acaacatcac cttcaaatat gacaattgta 180
ccacctactt gaatccagtg gggaagcatg tgattgctga cgcccagaat atcaccatca 240
gccagtatgc ttgccatgac caagtggcag tcaccattct ttggtcccca ggggccctcg 300
gcatcgaatt cctgaaagga tttcgggtaa tactggagga gctgaagtcg gagggaagac 360
agtgccaaca actgattcta aaggatccga agcagctcaa cagtagcttc aaaagaactg 420
gaatggaatc tcaacctttc ctgaatatga aatttgaaac ggattatttc gtaaaggttg 480
tcccttttcc ttccattaaa aacgaaagca attaccaccc tttcttcttt agaacccgag 540
cctgtgacct gttgttacag ccggacaatc tagcttgtaa acccttctgg aagcctcgga 600
acctgaacat cagccagcat ggctcggaca tgcaggtgtc cttcgaccac gcaccgcaca 660
acttcggctt ccgtttcttc tatcttcact acaagctcaa gcacgaagga cctttcaagc 720
gaaagacctg taagcaggag caaactacag agatgaccag ctgcctcctt caaaatgttt 780
ctccagggga ttatataatt gagctggtgg atgacactaa cacaacaaga aaagtgatgc 840
attatgcctt aaagccagtg cactccccgt gggccgggcc catcagagcc gtggccatca 900
cagtgccact ggtagtcata tcggcattcg cgacgctctt cactgtgatg tgccgcaaga 960

-continued agcaacaaga aaatatatat tcacatttag atgaagagag ctctgagtct tccacataca 1020
ctgcagcact cccaagagag aggctccggc cgcggccgaa ggtctttctc tgctattcca 1080
gtaaagatgg ccagaatcac atgaatgtcg tccagtgttt cgcctacttc ctccaggact 1140
tctgtggctg tgaggtggct ctggacctgt gggaagactt cagcctctgt agagaagggc 1200
agagagaatg ggtcatccag aagatccacg agtcccagtt catcattgtg gtttgttcca 1260
aaggcatgaa gtactttgtg gacaagaaga actacaaaca caaaggaggt ggccgaggct 1320
cggggaaagg agagctcttc ctggtggcgg tgtcagccat tgccgaaaag ctccgccagg 1380
ccaagcagag ttcgtccgcg gcgctcagca agtttatcgc cgtctacttt gattattcct 1440
gcgagggaga cgtccccggt atcctagacc tgagtaccaa gtacagactc atggacaatc 1500
ttcctcagct ctgttcccac ctgcactccc gagaccacgg cctccaggag ccggggcagc 1560
acacgcgaca gggcagcaga aggaactact tccggagcaa gtcaggccgg tccctatacg 1620
tcgccatttg caacatgcac cagtttattg acgaggagcc cgactggttc gaaaagcagt 1680
tcgttccctt ccatcctcct ccactgcgct accgggagcc agtcttggag aaatttgatt 1740
cgggcttggt tttaaatgat gtcatgtgca aaccagggcc tgagagtgac ttctgcctaa 1800
aggtagaggc ggctgttctt ggggcaaccg gaccagccga ctcccagcac gagagtcagc 1860
atgggggcct ggaccaagac ggggaggccc ggcctgccct tgacggtagc gccgccctgc 1920
aacccctgct gcacacggtg aaagccggca gcccctcgga catgccgcgg gactcaggca 1980
tctatgactc gtctgtgccc tcatccgagc tgtctctgcc actgatggaa ggactctcga 2040
cggaccagac agaaacgtct tccctgacgg agagcgtgtc ctcctcttca ggcctgggtg 2100
aggaggaacc tcctgccctt ccttccaagc tcctctcttc tgggtcatgc aaagcagatc 2160
ttggttgccg cagctacact gatgaactcc acgcggtcgc ccctttgtaa caaa 2214

<210> SEQ ID NO 5
<211> LENGTH: 739
<212> TYPE: PRT
<213> ORGANISM: Homo sapiens

<400> SEQUENCE: 5

Met Ala Pro Trp Leu Gln Leu Cys Ser Val Phe Phe Thr Val Asn Ala
1 5 10 15

Cys Leu Asn Gly Ser Gln Leu Ala Val Ala Ala Gly Gly Ser Gly Arg
20 25 30

Ala Arg Gly Ala Asp Thr Cys Gly Trp Arg Gly Val Gly Pro Ala Ser
35 40 45

Arg Asn Ser Gly Leu Tyr Asn Ile Thr Phe Lys Tyr Asp Asn Cys Thr
50 55 60

Thr Tyr Leu Asn Pro Val Gly Lys His Val Ile Ala Asp Ala Gln Asn
65 70 75 80

Ile Thr Ile Ser Gln Tyr Ala Cys His Asp Gln Val Ala Val Thr Ile
85 90 95

Leu Trp Ser Pro Gly Ala Leu Gly Ile Glu Phe Leu Lys Gly Phe Arg
100 105 110

Val Ile Leu Glu Glu Leu Lys Ser Glu Gly Arg Gln Cys Gln Gln Leu
115 120 125

Ile Leu Lys Asp Pro Lys Gln Leu Asn Ser Ser Phe Lys Arg Thr Gly
130 135 140

Met Glu Ser Gln Pro Phe Leu Asn Met Lys Phe Glu Thr Asp Tyr Phe
145 150 155 160

-continued

```
Val Lys Val Val Pro Phe Pro Ser Ile Lys Asn Glu Ser Asn Tyr His
                165                 170                 175

Pro Phe Phe Phe Arg Thr Arg Ala Cys Asp Leu Leu Leu Gln Pro Asp
            180                 185                 190

Asn Leu Ala Cys Lys Pro Phe Trp Lys Pro Arg Asn Leu Asn Ile Ser
        195                 200                 205

Gln His Gly Ser Asp Met Gln Val Ser Phe Asp His Ala Pro His Asn
    210                 215                 220

Phe Gly Phe Arg Phe Phe Tyr Leu His Tyr Lys Leu Lys His Glu Gly
225                 230                 235                 240

Pro Phe Lys Arg Lys Thr Cys Lys Gln Glu Gln Thr Thr Glu Met Thr
                245                 250                 255

Ser Cys Leu Leu Gln Asn Val Ser Pro Gly Asp Tyr Ile Ile Glu Leu
            260                 265                 270

Val Asp Asp Thr Asn Thr Thr Arg Lys Val Met His Tyr Ala Leu Lys
        275                 280                 285

Pro Val His Ser Pro Trp Ala Gly Pro Ile Arg Ala Val Ala Ile Thr
    290                 295                 300

Val Pro Leu Val Val Ile Ser Ala Phe Ala Thr Leu Phe Thr Val Met
305                 310                 315                 320

Cys Arg Lys Lys Gln Gln Glu Asn Ile Tyr Ser His Leu Asp Glu Glu
                325                 330                 335

Ser Ser Glu Ser Ser Thr Tyr Thr Ala Ala Leu Pro Arg Glu Arg Leu
            340                 345                 350

Arg Pro Arg Pro Lys Val Phe Leu Cys Tyr Ser Ser Lys Asp Gly Gln
        355                 360                 365

Asn His Met Asn Val Val Gln Cys Phe Ala Tyr Phe Leu Gln Asp Phe
    370                 375                 380

Cys Gly Cys Glu Val Ala Leu Asp Leu Trp Glu Asp Phe Ser Leu Cys
385                 390                 395                 400

Arg Glu Gly Gln Arg Glu Trp Val Ile Gln Lys Ile His Glu Ser Gln
                405                 410                 415

Phe Ile Ile Val Val Cys Ser Lys Gly Met Lys Tyr Phe Val Asp Lys
            420                 425                 430

Lys Asn Tyr Lys His Lys Gly Gly Gly Arg Gly Ser Gly Lys Gly Glu
        435                 440                 445

Leu Phe Leu Val Ala Val Ser Ala Ile Ala Glu Lys Leu Arg Gln Ala
    450                 455                 460

Lys Gln Ser Ser Ser Ala Ala Leu Ser Lys Phe Ile Ala Val Tyr Phe
465                 470                 475                 480

Asp Tyr Ser Cys Glu Gly Asp Val Pro Gly Ile Leu Asp Leu Ser Thr
                485                 490                 495

Lys Tyr Arg Leu Met Asp Asn Leu Pro Gln Leu Cys Ser His Leu His
            500                 505                 510

Ser Arg Asp His Gly Leu Gln Glu Pro Gly Gln His Thr Arg Gln Gly
        515                 520                 525

Ser Arg Arg Asn Tyr Phe Arg Ser Lys Ser Gly Arg Ser Leu Tyr Val
    530                 535                 540

Ala Ile Cys Asn Met His Gln Phe Ile Asp Glu Glu Pro Asp Trp Phe
545                 550                 555                 560

Glu Lys Gln Phe Val Pro Phe His Pro Pro Pro Leu Arg Tyr Arg Glu
                565                 570                 575

Pro Val Leu Glu Lys Phe Asp Ser Gly Leu Val Leu Asn Asp Val Met
            580                 585                 590
```

```
Cys Lys Pro Gly Pro Glu Ser Asp Phe Cys Leu Lys Val Glu Ala Ala
        595                 600                 605

Val Leu Gly Ala Thr Gly Pro Ala Asp Ser Gln His Glu Ser Gln His
    610                 615                 620

Gly Gly Leu Asp Gln Asp Gly Glu Ala Arg Pro Ala Leu Asp Gly Ser
625                 630                 635                 640

Ala Ala Leu Gln Pro Leu Leu His Thr Val Lys Ala Gly Ser Pro Ser
                645                 650                 655

Asp Met Pro Arg Asp Ser Gly Ile Tyr Asp Ser Ser Val Pro Ser Ser
            660                 665                 670

Glu Leu Ser Leu Pro Leu Met Glu Gly Leu Ser Thr Asp Gln Thr Glu
        675                 680                 685

Thr Ser Ser Leu Thr Glu Ser Val Ser Ser Ser Ser Gly Leu Gly Glu
    690                 695                 700

Glu Glu Pro Pro Ala Leu Pro Ser Lys Leu Leu Ser Ser Gly Ser Cys
705                 710                 715                 720

Lys Ala Asp Leu Gly Cys Arg Ser Tyr Thr Asp Glu Leu His Ala Val
                725                 730                 735

Ala Pro Leu


<210> SEQ ID NO 6
<211> LENGTH: 707
<212> TYPE: PRT
<213> ORGANISM: Homo sapiens

<400> SEQUENCE: 6

Leu Asp Tyr Arg Gln Ser Trp Pro Trp Gln Gly Val Gly Pro Ala Ser
1               5                   10                  15

Arg Asn Ser Gly Leu Tyr Asn Ile Thr Phe Lys Tyr Asp Asn Cys Thr
            20                  25                  30

Thr Tyr Leu Asn Pro Val Gly Lys His Val Ile Ala Asp Ala Gln Asn
        35                  40                  45

Ile Thr Ile Arg Gln Tyr Ala Cys His Asp Gln Val Ala Val Thr Ile
    50                  55                  60

Leu Trp Ser Pro Gly Ala Leu Gly Ile Glu Phe Leu Lys Gly Phe Arg
65                  70                  75                  80

Val Ile Leu Glu Glu Leu Lys Ser Glu Gly Arg Gln Cys Gln Gln Leu
                85                  90                  95

Ile Leu Lys Asp Pro Lys Gln Leu Asn Ser Ser Phe Lys Arg Thr Gly
            100                 105                 110

Met Glu Ser Gln Pro Phe Leu Asn Met Lys Phe Glu Thr Asp Tyr Phe
        115                 120                 125

Val Lys Val Val Pro Phe Pro Ser Ile Lys Asn Glu Ser Asn Tyr His
    130                 135                 140

Pro Phe Phe Phe Arg Thr Arg Ala Cys Asp Leu Leu Leu Gln Pro Asp
145                 150                 155                 160

Asn Leu Ala Cys Lys Pro Phe Trp Lys Pro Arg Asn Leu Asn Ile Ser
                165                 170                 175

Gln His Gly Ser Asp Met Gln Val Ser Phe Asp His Ala Pro His Asn
            180                 185                 190

Phe Gly Phe Arg Phe Phe Tyr Leu His Tyr Lys Leu Lys His Glu Gly
        195                 200                 205

Pro Phe Lys Arg Lys Thr Cys Lys Gln Glu Gln Thr Thr Glu Met Thr
    210                 215                 220
```

-continued

```
Ser Cys Leu Leu Gln Asn Val Ser Pro Gly Asp Tyr Ile Ile Glu Leu
225                 230                 235                 240

Val Asp Asp Thr Asn Thr Thr Arg Lys Val Met His Tyr Ala Leu Lys
                245                 250                 255

Pro Val His Ser Pro Trp Ala Gly Pro Ile Arg Ala Val Ala Ile Thr
            260                 265                 270

Val Pro Leu Val Val Ile Ser Ala Phe Ala Thr Leu Phe Thr Val Met
        275                 280                 285

Cys Arg Lys Lys Gln Gln Glu Asn Ile Tyr Ser His Leu Asp Glu Glu
    290                 295                 300

Ser Ser Glu Ser Ser Thr Tyr Thr Ala Ala Leu Pro Arg Glu Arg Leu
305                 310                 315                 320

Arg Pro Arg Pro Lys Val Phe Leu Cys Tyr Ser Ser Lys Asp Gly Gln
                325                 330                 335

Asn His Met Asn Val Val Gln Cys Phe Ala Tyr Phe Leu Gln Asp Phe
            340                 345                 350

Cys Gly Cys Glu Val Ala Leu Asp Leu Trp Glu Asp Phe Ser Leu Cys
        355                 360                 365

Arg Glu Gly Gln Arg Glu Trp Val Ile Gln Lys Ile His Glu Ser Gln
    370                 375                 380

Phe Ile Ile Val Val Cys Ser Lys Gly Met Lys Tyr Phe Val Asp Lys
385                 390                 395                 400

Lys Asn Tyr Lys His Lys Gly Gly Gly Arg Gly Ser Gly Lys Gly Glu
                405                 410                 415

Leu Phe Leu Val Ala Val Ser Ala Ile Ala Glu Lys Leu Arg Gln Ala
            420                 425                 430

Lys Gln Ser Ser Ser Ala Ala Leu Ser Lys Phe Ile Ala Val Tyr Phe
        435                 440                 445

Asp Tyr Ser Cys Glu Gly Asp Val Pro Gly Ile Leu Asp Leu Ser Thr
    450                 455                 460

Lys Tyr Arg Leu Met Asp Asn Leu Pro Gln Leu Cys Ser His Leu His
465                 470                 475                 480

Ser Arg Asp His Gly Leu Gln Glu Pro Gly Gln His Thr Arg Gln Gly
                485                 490                 495

Ser Arg Arg Asn Tyr Phe Arg Ser Lys Ser Gly Arg Ser Leu Tyr Val
            500                 505                 510

Ala Ile Cys Asn Met His Gln Phe Ile Asp Glu Glu Pro Asp Trp Phe
        515                 520                 525

Glu Lys Gln Phe Val Pro Phe His Pro Pro Pro Leu Arg Tyr Arg Glu
    530                 535                 540

Pro Val Leu Glu Lys Phe Asp Ser Gly Leu Val Leu Asn Asp Val Met
545                 550                 555                 560

Cys Lys Pro Gly Pro Glu Ser Asp Phe Cys Leu Lys Val Glu Ala Ala
                565                 570                 575

Val Leu Gly Ala Thr Gly Pro Ala Asp Ser Gln His Glu Ser Gln His
            580                 585                 590

Gly Gly Leu Asp Gln Asp Gly Glu Ala Arg Pro Ala Leu Asp Gly Ser
        595                 600                 605

Ala Ala Leu Gln Pro Leu Leu His Thr Val Lys Ala Gly Ser Pro Ser
    610                 615                 620

Asp Met Pro Arg Asp Ser Gly Ile Tyr Asp Ser Ser Val Pro Ser Ser
625                 630                 635                 640

Glu Leu Ser Leu Pro Leu Met Glu Gly Leu Ser Thr Asp Gln Thr Glu
                645                 650                 655
```

-continued

```
Thr Ser Ser Leu Thr Glu Ser Val Ser Ser Ser Ser Gly Leu Gly Glu
            660                 665                 670

Glu Glu Pro Pro Ala Leu Pro Ser Lys Leu Leu Ser Ser Gly Ser Cys
        675                 680                 685

Lys Ala Asp Leu Gly Cys Arg Ser Tyr Thr Asp Glu Leu His Ala Val
    690                 695                 700

Ala Pro Leu
705


<210> SEQ ID NO 7
<211> LENGTH: 2339
<212> TYPE: DNA
<213> ORGANISM: Homo sapiens

<400> SEQUENCE: 7

agcggattcg ctcttctttt cctccgggaa aagaaacggg aagtggccgt gggccggtga     60

attccgtgta gtggccaagc ttgttccaaa gagggggagg tgttgacagt ctcttgccca    120

ctgaagcgtg ccagacagag tgctaggcat gggggcagag gtgaatcaga tgacagccac    180

ctctcaccac gaggagtggc tgaaagtgtg actggactac aggcaatcct ggccttggca    240

gggagtgggg ccagccagca gaaacagtgg gctgtacaac atcaccttca aatatgacaa    300

ttgtaccacc tacttgaatc cagtggggaa gcatgtgatt gctgacgccc agaatatcac    360

catcaggcag tatgcttgcc atgaccaagt ggcagtcacc attctttggt ccccaggggc    420

cctcggcatc gaattcctga aaggatttcg ggtaatactg gaggagctga agtcggaggg    480

aagacagtgc caacaactga ttctaaagga tccgaagcag ctcaacagta gcttcaaaag    540

aactggaatg gaatctcaac ctttcctgaa tatgaaattt gaaacggatt atttcgtaaa    600

ggttgtccct tttccttcca ttaaaaacga aagcaattac caccctttct tctttagaac    660

ccgagcctgt gacctgttgt tacagccgga caatctagct tgtaaaccct tctggaagcc    720

tcggaacctg aacatcagcc agcatggctc ggacatgcag gtgtccttcg accacgcacc    780

gcacaacttc ggcttccgtt tcttctatct tcactacaag ctcaagcacg aaggaccttt    840

caagcgaaag acctgtaagc aggagcaaac tacagagatg accagctgcc tccttcaaaa    900

tgtttctcca ggggattata taattgagct ggtggatgac actaacacaa caagaaaagt    960

gatgcattat gccttaaagc cagtgcactc cccgtgggcc gggcccatca gagccgtggc   1020

catcacagtg ccactggtag tcatatcggc attcgcgacg ctcttcactg tgatgtgccg   1080

caagaagcaa caagaaaata tatattcaca tttagatgaa gagagctctg agtcttccac   1140

atacactgca gcactcccaa gagagaggct ccggccgcgg ccgaaggtct ttctctgcta   1200

ttccagtaaa gatggccaga atcacatgaa tgtcgtccag tgtttcgcct acttcctcca   1260

ggacttctgt ggctgtgagg tggctctgga cctgtgggaa gacttcagcc tctgtagaga   1320

agggcagaga gaatgggtca tccagaagat ccacgagtcc cagttcatca ttgtggtttg   1380

ttccaaaggt atgaagtact ttgtggacaa gaagaactac aaacacaaag gaggtggccg   1440

aggctcgggg aaaggagagc tcttcctggt ggcggtgtca gccattgccg aaaagctccg   1500

ccaggccaag cagagttcgt ccgcggcgct cagcaagttt atcgccgtct actttgatta   1560

ttcctgcgag ggagacgtcc ccggtatcct agacctgagt accaagtaca gactcatgga   1620

caatcttcct cagctctgtt cccacctgca ctcccgagac cacggcctcc aggagccggg   1680

gcagcacacg cgacagggca gcagaaggaa ctacttccgg agcaagtcag gccggtccct   1740

atacgtcgcc atttgcaaca tgcaccagtt tattgacgag gagcccgact ggttcgaaaa   1800
```

-continued gcagttcgtt cccttccatc ctcctccact gcgctaccgg gagccagtct tggagaaatt 1860
tgattcgggc ttggttttaa atgatgtcat gtgcaaacca gggcctgaga gtgacttctg 1920
cctaaaggta gaggcggctg ttcttggggc aaccggacca gccgactccc agcacgagag 1980
tcagcatggg ggcctggacc aagacgggga ggcccggcct gcccttgacg gtagcgccgc 2040
cctgcaaccc ctgctgcaca cggtgaaagc cggcagcccc tcggacatgc cgcgggactc 2100
aggcatctat gactcgtctg tgccctcatc cgagctgtct ctgccactga tggaaggact 2160
ctcgacggac cagacagaaa cgtcttccct gacggagagc gtgtcctcct cttcaggcct 2220
gggtgaggag gaacctcctg cccttccttc caagctcctc tcttctgggt catgcaaagc 2280
agatcttggt tgccgcagct acactgatga actccacgcg gtcgcccctt tgtaacaaa 2339

<210> SEQ ID NO 8
<211> LENGTH: 234
<212> TYPE: DNA
<213> ORGANISM: Homo sapiens

<400> SEQUENCE: 8
tgaagcgggc agaaagagtg gtggatgatg tccggggact ggcatgaccc tgggtctcag 60
cagtgctgct tgcatttgga ctccatgggg ctttgtgttg gaagagcaaa ttggcttcac 120
tctgcatcat gttctcttgt tttcccacag ggagtggggc cagccagcag aaacagtggg 180
ctgtacaaca tcaccttcaa atatgacaat tgtaccacct acttgaatcc agtg 234

<210> SEQ ID NO 9
<211> LENGTH: 585
<212> TYPE: DNA
<213> ORGANISM: Homo sapiens

<400> SEQUENCE: 9
gcggccgccg cggccaccgc ccactcgggg ctggccagcg gcgggcggcc ggggcgcaga 60
gaacggcctg gctgggcgag cgcacggcca tggccccgtg gctgcagctc tgctccgtct 120
tctttacggt caacgcctgc ctcaacggct cgcagctggc tgtggccgct ggcgggtccg 180
gccgcgcgcg gggcgccgac acctgtggct ggagggtaag gcgagggcgg cgggtttctt 240
gccgtcgcca actcgcgggg aacgcagcgc gcacaggtgc tcgcggggag gcgagcccgc 300
gccaacctgt ctgctcttcg cggggtccgc ggccggcctg ggtctcactc ctcccgcgca 360
tcctcctggt ttccctcccc ggacgcgtgt cctccggccc tggccgagat gaaagcggct 420
gcccgacccc ggctttgtgt tgctaatgag ggagtggggc cagccagcag aaacagtggg 480
ctgtacaaca tcaccttcaa atatgacaat tgtaccacct acttgaatcc agtggggaag 540
catgtgattg ctgacgccca gaatatcacc atcagccagt atgct 585

<210> SEQ ID NO 10
<211> LENGTH: 2240
<212> TYPE: DNA
<213> ORGANISM: Homo sapiens

<400> SEQUENCE: 10
gaggatcctg acggccatgg ccccgtggct gcagctctgc tccgtcttct ttacggtcaa 60
cgcctgcctc aacggctcgc agctggctgt ggccgctggc gggtccggcc gcgcgcgggg 120
cgccgacacc tgtggctgga ggggagtggg gccagccagc agaaacagtg ggctgtacaa 180
catcaccttc aaatatgaca attgtaccac ctacttgaat ccagtgggga agcatgtgat 240
tgctgacgcc cagaatatca ccatcagcca gtatgcttgc catgaccaag tggcagtcac 300

```
cattctttgg tccccagggg ccctcggcat cgaattcctg aaaggatttc gggtaatact    360
ggaggagctg aagtcggagg gaagacagtg ccaacaactg attctaaagg atccgaagca    420
gctcaacagt agcttcaaaa gaactggaat ggaatctcaa cctttcctga atatgaaatt    480
tgaaacggat tatttcgtaa aggttgtccc ttttccttcc attaaaaacg aaagcaatta    540
ccaccctttc ttctttagaa cccgagcctg tgacctgttg ttacagccgg acaatctagc    600
ttgtaaaccc ttctggaagc ctcggaacct gaacatcagc cagcatggct cggacatgca    660
ggtgtccttc gaccacgcac cgcacaactt cggcttccgt ttcttctatc ttcactacaa    720
gctcaagcac gaaggacctt tcaagcgaaa gacctgtaag caggagcaaa ctacagagat    780
gaccagctgc ctccttcaaa atgtttctcc aggggattat ataattgagc tggtggatga    840
cactaacaca acaagaaaag tgatgcatta tgccttaaag ccagtgcact ccccgtgggc    900
cgggcccatc agagccgtgg ccatcacagt gccactggta gtcatatcgg cattcgcgac    960
gctcttcact gtgatgtgcc gcaagaagca acaagaaaat atatattcac atttagatga   1020
agagagctct gagtcttcca catacactgc agcactccca agagagaggc tccggccgcg   1080
gccgaaggtc tttctctgct attccagtaa agatggccag aatcacatga atgtcgtcca   1140
gtgtttcgcc tacttcctcc aggacttctg tggctgtgag gtggctctgg acctgtggga   1200
agacttcagc ctctgtagag aagggcagag agaatgggtc atccagaaga tccacgagtc   1260
ccagttcatc attgtggttt gttccaaagg catgaagtac tttgtggaca agaagaacta   1320
caaacacaaa ggaggtggcc gaggctcggg gaaaggagag ctcttcctgg tggcggtgtc   1380
agccattgcc gaaaagctcc gccaggccaa gcagagttcg tccgcggcgc tcagcaagtt   1440
tatcgccgtc tactttgatt attcctgcga gggagacgtc cccggtatcc tagacctgag   1500
taccaagtac agactcatgg acaatcttcc tcagctctgt tcccacctgc actcccgaga   1560
ccacggcctc caggagccgg ggcagcacac gcgacagggc agcagaagga actacttccg   1620
gagcaagtca ggccggtccc tatacgtcgc catttgcaac atgcaccagt ttattgacga   1680
ggagcccgac tggttcgaaa agcagttcgt tcccttccat cctcctccac tgcgctaccg   1740
ggagccagtc ttggagaaat ttgattcggg cttggtttta aatgatgtca tgtgcaaacc   1800
agggcctgag agtgacttct gcctaaaggt agaggcggct gttcttgggg caaccggacc   1860
agccgactcc cagcacgaga gtcagcatgg gggcctggac caagacgggg aggcccggcc   1920
tgcccttgac ggtagcgccg ccctgcaacc cctgctgcac acggtgaaag ccggcagccc   1980
ctcggacatg ccgcgggact caggcatcta tgactcgtct gtgccctcat ccgagctgtc   2040
tctgccactg atggaaggac tctcgacgga ccagacagaa acgtcttccc tgacggagag   2100
cgtgtcctcc tcttcaggcc tgggtgagga ggaacctcct gcccttcctt ccaagctcct   2160
ctcttctggg tcatgcaaag cagatcttgg ttgccgcagc tacactgatg aactccacgc   2220
ggtcgcccct ttgtaacaaa                                               2240
```

<210> SEQ ID NO 11
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 11

```
agcaagtcag gccggtccct ata                                             23
```

<210> SEQ ID NO 12
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 12
ggtgaaggtc ggagtcaacg ga 22

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
gagggatctc gctcctggaa ga 22

<210> SEQ ID NO 14
<211> LENGTH: 115
<212> TYPE: PRT
<213> ORGANISM: Artificial sequence
<220> FEATURE:
<223> OTHER INFORMATION: Partial predicted amino acid sequence of hSef-d

<400> SEQUENCE: 14

Ala Val Ala Asn Ser Arg Gly Thr Gln Arg Ala Gln Val Leu Ala Gly
1 5 10 15

Arg Arg Ala Arg Ala Asn Leu Ser Ala Leu Arg Gly Val Arg Gly Arg
20 25 30

Pro Gly Ser His Ser Ser Arg Ala Ser Ser Trp Phe Pro Ser Pro Asp
35 40 45

Ala Cys Pro Pro Ala Leu Ala Glu Met Lys Ala Ala Ala Arg Pro Arg
50 55 60

Leu Cys Val Ala Asn Glu Gly Val Gly Pro Ala Ser Arg Asn Ser Gly
65 70 75 80

Leu Tyr Asn Ile Thr Phe Lys Tyr Asp Asn Cys Thr Thr Tyr Leu Asn
85 90 95

Pro Val Gly Lys His Val Ile Ala Asp Ala Gln Asn Ile Thr Ile Ser
100 105 110

Gln Tyr Ala
115

<210> SEQ ID NO 15
<211> LENGTH: 77
<212> TYPE: PRT
<213> ORGANISM: Homo sapiens

<400> SEQUENCE: 15

Ser Gly Gln Lys Glu Trp Trp Met Met Ser Gly Asp Trp His Asp Pro
1 5 10 15

Gly Ser Gln Gln Cys Cys Leu His Leu Asp Ser Met Gly Leu Cys Val
20 25 30

Gly Arg Ala Asn Trp Leu His Ser Ala Ser Cys Ser Leu Val Phe Pro
35 40 45

Gln Gly Val Gly Pro Ala Ser Arg Asn Ser Gly Leu Tyr Asn Ile Thr
50 55 60

Phe Lys Tyr Asp Asn Cys Thr Thr Tyr Leu Asn Pro Val
65 70 75

-continued

<210> SEQ ID NO 16
<211> LENGTH: 37
<212> TYPE: DNA
<213> ORGANISM: Artificial sequence
<220> FEATURE:
<223> OTHER INFORMATION: Single strand DNA oligonucleotide

<400> SEQUENCE: 16
gaggatcctg acggccatgg ccccgtggct gcagctc 37

<210> SEQ ID NO 17
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 17
tgaagctact gttgagctgc ttcg 24

<210> SEQ ID NO 18
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 18
cagacgagtc atagatgcct gagt 24

<210> SEQ ID NO 19
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 19
cttcactctg catcatgttc tcttg 25

<210> SEQ ID NO 20
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 20
gtgactgcca cttggtcatg gca 23

<210> SEQ ID NO 21
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 21
gacacctgtg gctggagggt aag 23

<210> SEQ ID NO 22
<211> LENGTH: 60
<212> TYPE: DNA
<213> ORGANISM: Artificial sequence
<220> FEATURE:
<223> OTHER INFORMATION: hSef-b RACE derived fragment

<400> SEQUENCE: 22
aaacgggaag tggccgtggg ccggtgaatt ccgtgtagtg gccaagcttt gttccaaaga 60

<210> SEQ ID NO 23
<211> LENGTH: 19
<212> TYPE: DNA
<213> ORGANISM: Artificial sequence
<220> FEATURE:
<223> OTHER INFORMATION: ShRNA oligonucleotide

<400> SEQUENCE: 23
gtcggaggga agacagtgc 19

<210> SEQ ID NO 24
<211> LENGTH: 19
<212> TYPE: DNA
<213> ORGANISM: Artificial sequence
<220> FEATURE:
<223> OTHER INFORMATION: ShRNA oligonucleotide

<400> SEQUENCE: 24
gcactgtctt ccctccgac 19

<210> SEQ ID NO 25
<211> LENGTH: 19
<212> TYPE: DNA
<213> ORGANISM: Artificial sequence
<220> FEATURE:
<223> OTHER INFORMATION: ShRNA oligonucleotide

<400> SEQUENCE: 25
gcatgtgatt gctgacgcc 19

<210> SEQ ID NO 26
<211> LENGTH: 19
<212> TYPE: DNA
<213> ORGANISM: Artificial sequence
<220> FEATURE:
<223> OTHER INFORMATION: ShRNA oligonucleotide

<400> SEQUENCE: 26
ggcgtcagca atcacatgc 19

<210> SEQ ID NO 27
<211> LENGTH: 19
<212> TYPE: DNA
<213> ORGANISM: Artificial sequence
<220> FEATURE:
<223> OTHER INFORMATION: ShRNA oligonucleotide

<400> SEQUENCE: 27
agcaggagca aactacaga 19

<210> SEQ ID NO 28
<211> LENGTH: 19
<212> TYPE: DNA
<213> ORGANISM: Artificial sequence
<220> FEATURE:
<223> OTHER INFORMATION: ShRNA oligonucleotide

<400> SEQUENCE: 28
tctgtagttt gctcctgct 19

<210> SEQ ID NO 29
<211> LENGTH: 19

-continued

```
<212> TYPE: DNA
<213> ORGANISM: Artificial sequence
<220> FEATURE:
<223> OTHER INFORMATION: ShRNA oligonucleotide

<400> SEQUENCE: 29

cgtgacagaa gggaggctg                                              19


<210> SEQ ID NO 30
<211> LENGTH: 19
<212> TYPE: DNA
<213> ORGANISM: Artificial sequence
<220> FEATURE:
<223> OTHER INFORMATION: ShRNA oligonucleotide

<400> SEQUENCE: 30

cagcctccct tctgtcacg                                              19


<210> SEQ ID NO 31
<211> LENGTH: 613
<212> TYPE: DNA
<213> ORGANISM: Artificial sequence
<220> FEATURE:
<223> OTHER INFORMATION: In situ hybridization probe

<400> SEQUENCE: 31

acaaaggggc gaccgcgtgg agttcatcag tgtagctgcg gcaaccaaga tctgctttgc      60

atgacccaga agagaggagc ttggaaggaa gggcaggagg ttcctcctca cccaggcctg     120

aagaggagga cacgctctcc gtcagggaag acgtttctgt ctggtccgtc gagagtcctt     180

ccatcagtgg cagagacagc tcggatgagg gcacagacga gtcatagatg cctgagtccc     240

gcggcatgtc cgaggggctg ccggctttca ccgtgtgcag caggggttgc agggcggcgc     300

taccgtcaag ggcaggccgg gcctccccgt cttggtccag gcccccatgc tgactctcgt     360

gctgggagtc ggctggtccg gttgccccaa gaacagccgc ctctaccttt aggcagaagt     420

cactctcagg ccctggtttg cacatgacat catttaaaac caagcccgaa tcaaatttct     480

ccaagactgg ctcccggtag cgcagtggag gaggatggaa gggaacgaac tgcttttcga     540

accagtcggg ctcctcgtca ataaactggt gcatgttgca aatggcgacg tatagggacc     600

ggcctgactt gct                                                       613
```

HUMAN SEF ISOFORMS AND METHODS OF USING SAME FOR CANCER DIAGNOSIS AND GENE THERAPY

RELATED APPLICATIONS

This application is a Continuation of U.S. patent application Ser. No. 11/493,608, filed on Jul. 27, 2006, which is a Continuation-In-Part (CIP) of U.S. patent application Ser. No. 10/963,439, filed on Oct. 11, 2004, the contents of which are incorporated herein by reference.

FIELD AND BACKGROUND OF THE INVENTION

The present invention relates to polypeptides and polynucleotides expressing the human Sef b-d isoforms (hSefb-d), and more particularly, to the use of such isoforms in the inhibition of uncontrolled malignant proliferation of solid tumors.

Solid tumors account for the majority of human tumors and among them, carcinomas of an epithelial origin, account for over 80%. Conventional therapies for solid tumors involves the administration of anti-tumor drugs such as thymidylate synthase inhibitors (e.g., 5-fluorouracil; Rose M G et al., 2002; Clin Colorectal Cancer. 1: 220-9), nucleoside analogs [e.g., gemcitabine (Gemzar); Seidman A D., 2001. Oncology (Huntingt). 15: 11-14), non-steroidal (e.g., anastrozole and letrozole) and steroidal (exemestane) aromatase inhibitors (Lake D E and Hudis C., 2002; Cancer Control; 9: 490-8), taxanes and topoisomerase-I inhibitors (e.g., irinotecan; Van Cutsem, E. 2004; The Oncologist, 9, Suppl 2, 9-15). However, the use of such drugs often fails due to the development of drug resistance by the cancer cells. Thus, despite the tremendous progress in understanding tumor biology and early detection of cancer, cancer mortality rates have not been significantly reduced.

The growth of solid tumors depends on nutrients and oxygen which are supplied by the tumor vasculature. The growth of new blood vessels into the tumor is controlled by paracrine signals, many of which are mediated by protein ligands which modulate the activity of transmembrane tyrosine kinase receptors (RTK). These include vascular endothelial growth factor (VEGF) and its receptor families (VEGFR-1, VEGFR-2, neuropilin-1 and neuropilin-2), Angiopoietins 1-4 (Ang-1, Ang-2) and their respective receptors (Tie-1 and Tie-2), basic fibroblast growth factor (bFGF), platelet derived growth factor (PDGF), transforming growth factor β (TGF-β) and their receptors. Thus, it was conceivable that inhibition of angiogenesis can inhibit the growth of solid tumors.

Indeed, several studies have demonstrated that anti-angiogenic agents such as Endostatin, AGM-1470, angiostatin, BB-94, 2-Methoxyestradiol (2-ME) and Taxol in can inhibit tumor growth in vivo (Boehm et al., 1997; Nature; 390: 404-7; Bergers et al., 1999; Science; 284: 808-12; Klauber N et al. 1997; 57: 81-6). However, the mechanisms by which such agents exert their anti-tumor effect remain unclear (O'Reilly et al., 1997; Oreilly et al., 1996).

The interest in FGFs and their receptors as potential drug targets arose from their wide distribution in cells of different lineages and their mitogenic and angiogenic activities, two essential activities for solid tumor growth and metastasis (Zetter, B. R. 1998; Annu. Rev. Med. 49: 407-424). The oncogenic potential of FGFs is well documented in both, in-vitro studies and animal model systems (McKeehan, W. L., et al., 1998; Prog. Nucleic. Acid. Res. Mol. Biol. 59: 135-176; Szebenyi, G. and Fallon, J. F. 1999; Int. Rev. Cytol. 185: 45-106; Shaoul, E., et al., 1995; Oncogene 10: 1553-1561; Miki, T., et al., 1991; Science 251: 72-75; Kitsberg, D. I. and Leder, P. 1996. Oncogene 13: 2507-2515). Moreover, a variety of human carcinomas including pancreatic, endometrial and prostate carcinomas, overexpress FGFs (FGF-1, FGF-2 and FGF-7) and their receptors (KGFR and FGFR1), and tumor aggressiveness is correlated with the level of expression of these receptors (Giri, D., et al., 1999; Clin. Cancer Res. 5: 1063-1071; Visco, V., et al., 1999; Int. J. Oncol. 15: 431-435; Siegfried, S., et al., 1997; Cancer 79: 1166-1171; Ishiwata, T., et al., 1998; Am. J. Pathol. 153: 213-222; Kornmann, M., et al., 1998; Pancreas 17: 169-175; Siddiqi, I., et al., 1995; Biochem. Biophys. Res. Commun. 215: 309-315). Altogether, these observations strongly suggest the involvement of FGFs and their receptors in the malignant process. Thus, developing tools to target FGFRs, and their signaling pathways could be very useful for cancer therapy.

Several mechanisms collectively known as "negative signaling" have been evolved to attenuate signaling by RTKs (Christofori, G., 2003). One such mechanism involves ligand-induced antagonists of RTK signaling. The Sprouty and SPRED (Sprouty related EVH1-domain-containing) proteins belong to this category, and are regarded as general inhibitors of RTK signaling. They suppress the RTK-induced mitogen-activated protein kinase (MAPK) pathway (reviewed in Christofori, G., 2003; Dikic and Giordano, 2003).

Sef (for Similar Expression to FGF genes) is a newly identified antagonist of fibroblast growth factor (FGF) signaling. Sef encodes a putative type I transmembrane protein that is conserved across zebrafish, mouse and human but not in invertebrates (Furthauer, M., et al., 2002; Tsang M., et al., 2002; Lin, W., et al., 2002). Zebrafish Sef (zfSef) antagonizes FGF activity during embryogenesis by acting as a feedback-induced antagonist of the Ras/MAPK mediated FGF-signaling (Furthauer, M., et al., 2002; Tsang M., et al., 2002). Subsequent studies showed that the mouse (Kovalenko D, 2003) homologue of zfSef similarly inhibit FGF-induced activation of MAPK, and FGF-induced activation of protein-kinase B (pkB/Akt), a key protein in the phosphatidylinositol-3 (PI3) kinase pathway. On the other hand, the mSef was unable to inhibit PDGF-, EGF- or calf serum-induced phosphorylation of ERK in NIH 3T3 cells (Kovalenko D, 2003). Other studies showed that the human Sef homologue (which is later referred to as hSef-a by the present inventor) is capable of inhibiting FGF- and NGF-induced differentiation of PC12 cells (Xiong et al., 2003; JBC 278: 50273-50282).

The expression level of human Sef in normal and malignant tissues has been controversial. While Yang R B., et al (J. Biol. Chem. 2003, 278:33232-8) found that Sef is expressed a variety of breast cancer tissues, Darby S, (Oncogene. 2006, 25: 4122-7) found that loss of Sef expression is associated with high grade and metastais of prostate cancer only. Thus, to date, cancer diagnosis which is based on Sef expression level has not been suggested. In addition, none of these studies have suggested using Sef expression for staging of cancer, determining disease course and/or cancer prognosis and/or for selecting an anti-cancer therapy regimen.

There is thus, a widely recognized need to develop agents suitable for diagnosing and treating cancerous solid tumors.

SUMMARY OF THE INVENTION

While reducing the present invention to practice, the present inventor has uncovered three new alternatively spliced isoforms of the human Sef (designated hSefb-d) and demonstrated the capacity of hSefb to inhibit FGF and PDGF RTK signaling. In addition, the present inventor has shown that the expression of hSef is reduced in various solid tumors such as thyroid carcinoma, breast cancer, ovarian cancer and prostate cancer in a manner which correlates with an increase in tumor malignancy. Moreover, the present inventor has demonstrated that overexpression of hSef results in suppression of colony formation and growth of cancerous cells. Thus, the present inventor has uncovered that agents capable of upregulating hSef can be used to inhibit the growth of solid tumors and thereby treat cancer. In addition, the present inventor has uncovered that the decrease in hSef expression can be used as a tool for diagnosing solid tumor, determining disease course and/or cancer prognosis and/or for selecting an anti-cancer therapy regimen.

According to one aspect of the present invention there is provided a method of inhibiting a growth of a solid tumor in a subject, the method comprising administering to the subject an agent capable of upregulating the expression level and/or activity of at least a functional portion of Sef, the at least a functional portion of Sef being capable of inhibiting RTK-mediated cell proliferation, thereby inhibiting the growth of the solid tumor in the subject.

According to another aspect of the present invention there is provided a pharmaceutical composition useful for inhibiting a growth of a solid tumor in a subject comprising, as an active ingredient, an agent capable of upregulating the expression level and/or activity of at least a functional portion of Sef, the at least a functional portion of Sef being capable of inhibiting RTK-mediated cell proliferation, and a pharmaceutically acceptable carrier.

According to yet another aspect of the present invention there is provided a method of diagnosing cancer in a subject in need thereof, the method comprising detecting in a tissue sample of the subject an expression level of Sef, wherein a decrease in the expression level of the Sef compared to the expression level of the Sef in an unaffected tissue is indicative of the cancer, thereby diagnosing the cancer in the subject in need thereof.

According to still another aspect of the present invention there is provided a kit for diagnosing cancer in a subject in need thereof, the kit comprising a reagent for detecting an expression level of Sef, wherein a decrease in the expression level of the Sef compared to the expression level of the Sef in an unaffected tissue is indicative of the cancer.

According to further features in preferred embodiments of the invention described below, the RTK-mediated cell proliferation is ligand independent.

According to still further features in the described preferred embodiments the RTK-mediated cell proliferation is ligand-induced.

According to still further features in the described preferred embodiments the at least a functional portion of Sef is a polypeptide as set forth by SEQ ID NO:6.

According to still further features in the described preferred embodiments the at least a functional portion of Sef is a polypeptide as set forth by amino acid coordinates 1-10, 267-707 and/or 288-707 of SEQ ID NO:6.

According to still further features in the described preferred embodiments upregulating is effected by at least one approach selected from the group consisting of:

(a) expressing in cells of the subject an exogenous polynucleotide encoding at least a functional portion of Sef;

(b) increasing expression of endogenous Sef in cells of the subject;

(c) increasing endogenous Sef activity in cells of the subject; and (d) introducing an exogenous peptide and/or exogenous polypeptide including at least a functional portion of Sef to the subject.

According to still further features in the described preferred embodiments the exogenous polynucleotide is a nucleic acid construct comprising a polynucleotide at least 90% identical to the polynucleotide sequence set forth in SEQ ID NO:4.

According to still further features in the described preferred embodiments the exogenous polynucleotide is a nucleic acid construct comprising a polynucleotide selected from the group consisting of SEQ ID NOs:4, 8, and 9.

According to still further features in the described preferred embodiments the nucleic acid construct further comprises a promoter capable of directing an expression of the polynucleotide in the cells of the subject.

According to still further features in the described preferred embodiments the promoter is selected from the group consisting of Cytomegalovirus (CMV) promoter, simian virus (SV)-40 early promoter, SV-40 late promoter, metallothionein promoter, murine mammary tumor virus promoter, Rous sarcoma virus (RSV) promoter, and According to still further features in the described preferred embodiments the Sef is a polypeptide at least 90% homologous (identical+similar) to a polypeptide set forth by SEQ ID NO:6 as determined using the BlastP software where gap open penalty equals 11, gap extension penalty equals 1 and matrix is blosum 62.

According to still further features in the described preferred embodiments the Sef is a polypeptide set forth by SEQ ID NO:6.

According to still further features in the described preferred embodiments the solid tumor is selected from the group consisting of ovarian carcinoma, pancreatic cancer, breast cancer, endometrial carcinoma, brain tumor, adrenal carcinoma, pituitary cancer, thyroid carcinoma, tonsillar carcinoma, spleen cancer, adenoids cancer, kidney cancer, liver cancer, testis cancer, bladder cancer, colon cancer, prostate cancer, bile duct, lung cancer, and stomach cancer.

According to still further features in the described preferred embodiments the ligand is selected from the group consisting of FGF, PDGF, VEGF, NGF, insulin, and EGF.

According to still further features in the described preferred embodiments the RTK-mediated cell proliferation is effected by inhibition of activated Erk1/2 (P-Erk1/2) within the cells.

According to still further features in the described preferred embodiments the cancer is a solid tumor.

According to still further features in the described preferred embodiments the solid tumor is selected from the group consisting of breast cancer, ovarian cancer, thyroid carcinoma and prostate cancer.

According to still further features in the described preferred embodiments the Sef is a nucleic acid sequence of Sef.

According to still further features in the described preferred embodiments the Sef is an amino acid sequence of Sef.

According to still further features in the described preferred embodiments detecting is effected by an RNA detection method.

According to still further features in the described preferred embodiments detecting is effected by a protein detection method According to still further features in the described preferred embodiments the RNA detection method is selected from the group consisting of RNA in situ hybridization, RT-PCR, in situ RT-PCR and Northern blot analysis.

According to still further features in the described preferred embodiments the protein detection method is selected from the group consisting of ELISA, Western blot, immunofluorescence and immunohistochemical analysis.

According to still further features in the described preferred embodiments the solid tumor is a primary solid tumor.

According to still further features in the described preferred embodiments the Sef is Sef-a and whereas the solid tumor is breast cancer or ovarian cancer.

According to still further features in the described preferred embodiments the Sef is Sef-b and whereas the solid tumor is thyroid carcinoma.

According to still further features in the described preferred embodiments the method further comprising determining a malignancy of the solid tumor.

According to still further features in the described preferred embodiments the reagent is utilized for an RNA detection method.

According to still further features in the described preferred embodiments the reagent is utilized in a protein detection method.

According to still further features in the described preferred embodiments the reagent is an isolated nucleic acid sequence complementary to the Sef nucleic acid sequence.

According to still further features in the described preferred embodiments the reagent is an antibody or antibody fragment which comprises an antigen recognition region capable of specifically binding the Sef amino acid sequence.

The present invention successfully addresses the shortcomings of the presently known configurations by providing agents and pharmaceutical compositions suitable for inhibiting the growth of solid tumors and methods and kits for diagnosing cancer, and/or for selecting an anti-cancer therapy regimen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The patent or application file contains at least one drawing executed in color. Copies of this patent or patent application publication with color drawing(s) will be provided by the Office upon request and payment of the necessary fee.

In the drawings:

Figure 1:
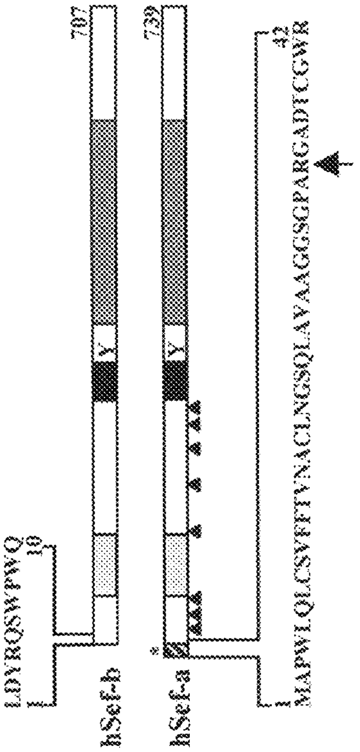

FIG. 1 is a schematic illustration depicting the structural homology between the human Sef-a and Sef-b isoforms. Shown are residues unique in each Sef isoform (bold letters), the signal for secretion (asterisk), potential N-linked glycosylation sites (arrows), transmembrane domain (black box), putative tyrosine phosphorylation site (Y), immunoglobulin like domain and the IL-17R-like domain (light and dark gray boxes). Note that while the human Sef-a contains a signal for secretion (the sequence appears left to the arrow), the hSef-b isoform lacks such a signal.

FIGS. 2*a-b* are autoradiographs depicting the identification of hSef protein products. FIG. 2*a*—Western blot analysis. HEK 293 cells were transiently transfected with either a control empty vector (lane 1) or Myc-tagged hSef-b or hSef-a vectors (lanes 2 and 3, respectively). Equal amounts of protein were subjected to SDS-PAGE followed by α-myc immunoblotting. FIG. 2*b*—in-vitro translation of hSef-b. In vitro transcription-translation was performed in the presence of [$^{35}$S]-methionine and either an expression vector including the hSef-b cDNA (lane 1) or an empty vector (lane 2). The translation products were analyzed by SDS-PAGE, and visualized by phospho-imaging.

FIGS. 3*a-d* are immunofluorescence staining depicting the cellular localization of the hSef isoforms. HEK 293 cells were transfected with the myc-tagged hSef-a (FIGS. 3*a* and *b*) or the myc-tagged hSef-b (FIGS. 3*c* and *d*) expression vectors, and 48 hours post-transfection the cells were subjected to immunostaining using α-myc (red; Figures a and c) or α-hSef (green; FIGS. 3*b* and *d*) antibodies. Nuclei were counterstained with bisbenzimide (blue).

FIGS. 4*a-d* are agarose gel images depicting the expression pattern of human Sef isoforms as determined by RT-PCR analyses. Total RNA from the indicated human tissues and human primary cells was subjected to RT-PCR using primers specific to the common hSef transcript (SEQ ID NOs:11 and 18, FIG. 4*a*), to the hSef-a (SEQ ID NOs:17 and 16, FIG. 4*b*), hSef-b (SEQ ID NOs:2 and 17, FIG. 4*c*), or GAPDH (SEQ ID NOs:12 and 13). Adrenal m=adrenal medulla; adrenal c=adrenal cortex; A.E. cells=primary aortic endothelial cells; F. Brain=fetal brain; A. Brain=adult brain; F. Kidney=fetal kidney; NC=negative control; PC=positive control. Templates for positive controls are plasmids containing hSef-a (FIGS. 4*a-b*); hSef-b (FIG. 4*c*) or GAPDH (FIG. 4*d*).

Figure 5:
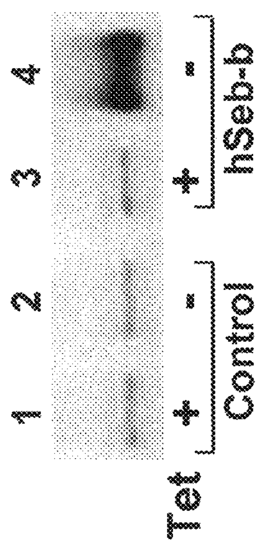

FIG. 5 is an autoradiograph depicting induced expression of hSef-b in the Tet-off NIH/3T3 cells. Cells were grown in 10% serum in the presence (lanes 1 and 3) or absence (lanes 2 or 4) of tetracycline. Following 24 hours, the cells were lysed and hSef-b expression was analyzed by immunoblotting with hSef specific antibodies. Lanes 1 and 2=Control cultures of parental cells transfected with an empty pTet-Splice vector; lanes 3 and 4=Cells transfected with the pTet-Splice-hSef-b vector.

Figure 6A:
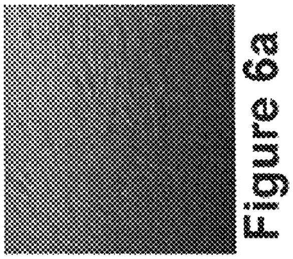
Figure 6B:
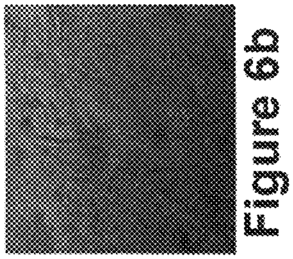
Figure 6C:
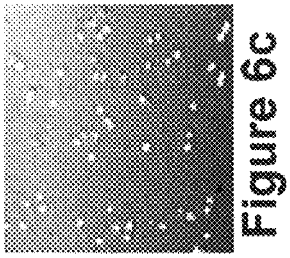

FIGS. 6*a-c* are photomicrographs illustrating the effect of hSef-b on apoptosis. NIH/3T3/hSef-b cells were grown for 48 hours in the presence (FIG. 6*a*) or absence (FIGS. 6*b* and 6*c*) of tetracycline, and in the absence of tetracycline and serum (FIG. 6*c*). Cells were washed, fixed and apoptosis was then evaluated by TUNEL staining. Note the presence of apoptotic cells in the absence of tetracycline and serum (FIG. 6*c*).

Figure 7A:
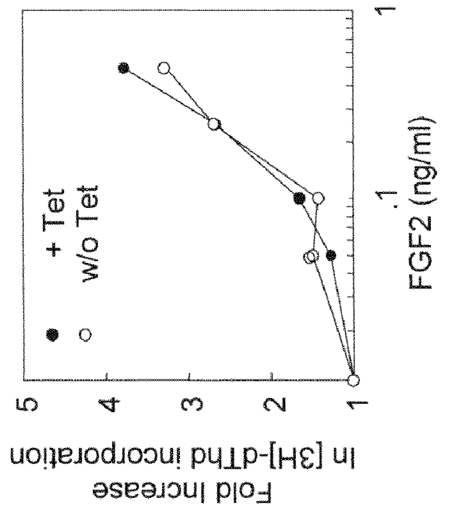
Figure 7B:
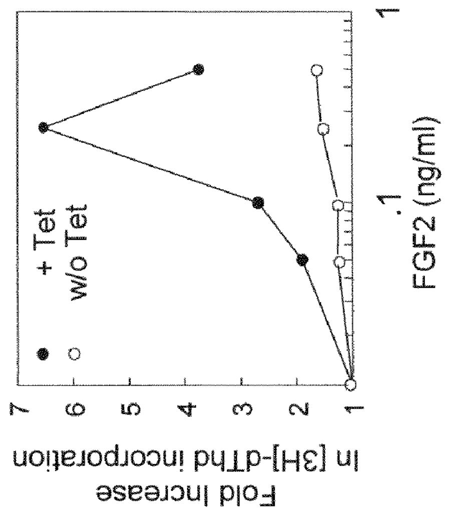

FIGS. 7*a-b* are graphs illustrating the inhibition of the mitogenic activity of FGF2 by human Sef-b. Confluent cultures of control (FIG. 7*a*) or hSef-b expressing (FIG. 7*b*) cells were serum starved (in the presence of 0.2% serum) for 24 hours in the presence or absence of tetracycline. FGF2 was added at the above-indicated concentrations and [$^{3}$H]-thymidine incorporation assay was performed as previously described (24, 26).

Figure 8:
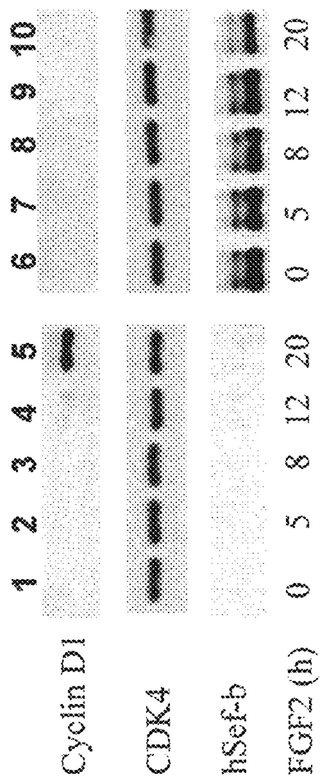

FIG. 8 is a Western Blot analysis illustrating the effect of hSef-b on cyclin D1 levels. Human Sef-b inducible NIH/3T3 cells were serum starved for 24 hours in the presence (lanes 1-5) or absence (lanes 6-10) of tetracycline, following which the cells were stimulated with FGF2 (20 ng/ml) for 0 (lanes 1 and 6), 5 (lanes 2 and 7), 8 (lanes 3 and 8), 12 (lanes 4 and 9), or 20 (lanes 5 and 10) hours. The levels of cyclin D1 were evaluated in total cell lysates over 20 hours of stimulation. Cyclin D1 and CDK proteins were analyzed by immunoblotting with anti-D1 monoclonal antibody and rabbit anti-CDK4, respectively. Note the presence of the Cyclin D1 protein in cells grown with tetracycline and the absence of such protein following tetracycline removal and activation of hSef-b expression.

Figure 9A:
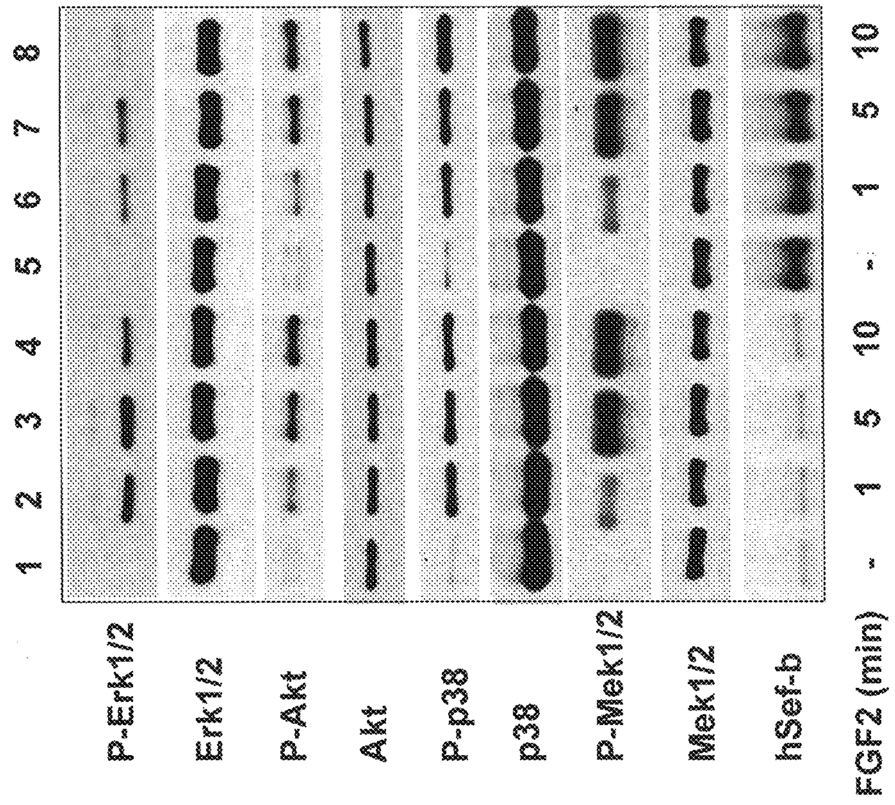
Figure 9B:
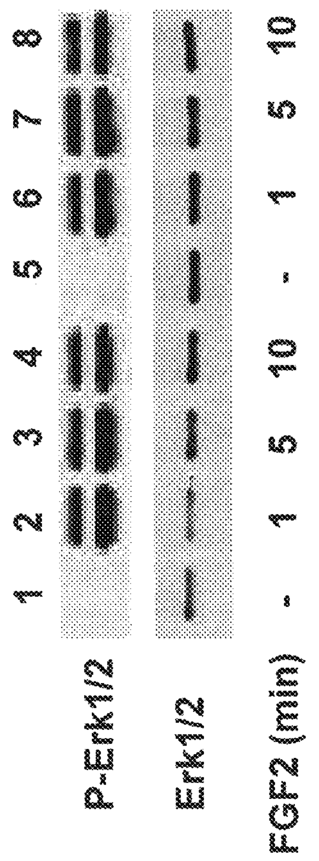

FIGS. 9*a-b* are Western Blot analyses illustrating the effect of hSef-b on FGF2-induced signaling pathways. FIG. 9*a*—NIH 3T3 hSef-b expressing cells; FIG. 9*b*—NIH 3T3 cells transfected with an empty vector (control cultures). Equal amounts of total cells lysates were analyzed by immunoblotting. The membranes were successively incubated with the indicated antibodies. Lanes 1-4: cells were grown in the presence of tetracycline; lanes 5-8: cells were grown in the absence of tetracycline. Note that while in cells transfected with the control empty vector Erk1/2 activation was not influenced by tetracycline removal (FIG. 9*b*), in hSef-b-expressing cells tetracycline removal resulted in a decrease in the level of P-Erk1/2, but not the level of total Erk1/2. Each experiment was repeated at least twice and using two independent clones of hSef-b inducible cells. P-Erk 1/2, P-Akt, P-p38 and P-MEK1/2 are antibodies directed against the phosphorylated (P) form of each of the kinases.

Figure 10A:
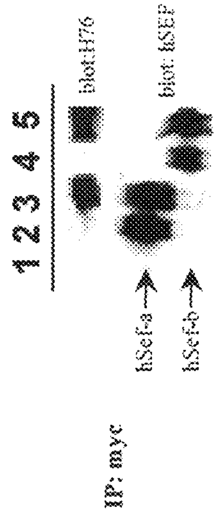
Figure 10B:

FIGS. 10*a-b* are autoradiographs illustrating co-immunoprecipitation analyses of Sef isoforms and FGFR1. HEK 293 cells were transfected with the indicated constructs and immunoblotting with α-FGFR1 (H76) or α-hSef antibodies was performed on whole cell lysates (WCL; FIG. 10*b*) or on cell lysates following α-myc immunoprecipitation (IP; FIG. 10*a*). Lane 1—transfection with the FGFR1 construct; lane 2—transfection with hSef-a construct containing the c-myc epitop at the C-terminus (hSef-a::myc); lane 3—co-transfection with the FGFR1 and the hSef-a::myc constructs; lane 4=transfection with the hSef-b construct containing the c-myc epitop at the C-terminus (hSef-b::myc); lane 5—co-transfection with the FGFR1 and the hSef-b::myc constructs.

Figure 11A:
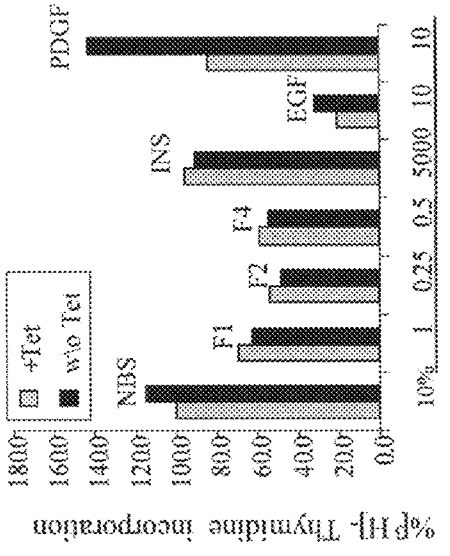
Figure 11B:
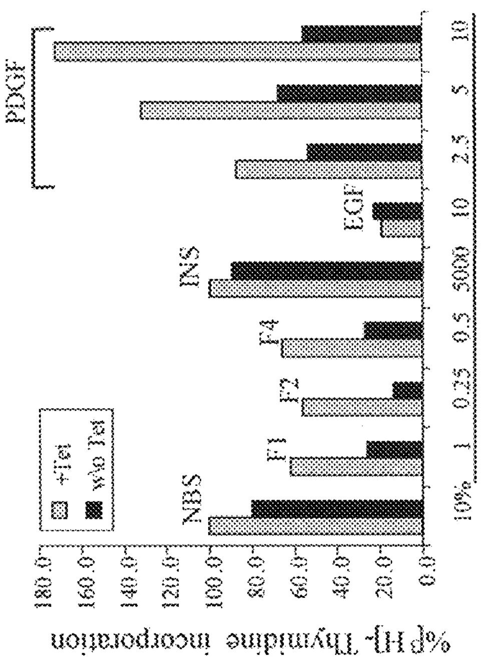

FIGS. 11*a-b* are bar graphs depicting mitogenic assays in control (FIG. 11*a*) or hSef-b expressing (FIG. 11*b*) cells. Confluent cultures were subjected to mitogenic assays as describe in FIGS. 7*a-b* and the fold increase (FI) in biological activity was calculated by dividing CPM values obtained in the presence of the indicated stimulators with those obtained in the presence of 0.2% serum alone. Percent [$^3$H]-thymidine incorporation is relative to FI obtained in cultures stimulated with 10% serum in the presence of tetracycline that was set as 100%. The concentrations of FGFs, insulin, EGF and serum are those which gave rise to a maximal biological response. F=FGF; INS=insulin.

Figure 12:
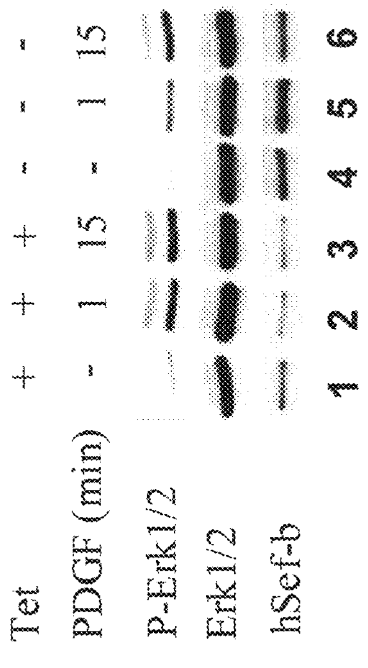

FIG. 12 is a Western Blot analysis illustrating the effect of hSef-b-mediated PDGF inhibition of ERK1/2 MAPK level. Human Sef-b inducible NIH/3T3 cells were serum starved for 24 hours in the presence (lanes 1-3) or absence (lanes 4-6) of tetracycline, following which the cells were stimulated with 20 ng/ml PDGF for the indicated time periods. Equal amounts of total cells lysates were analyzed by immunoblotting using anti-P-Erk 1/2 and anti-ERK antibodies. These experiments were repeated at least 3 times and using two independent hSef-b expressing clones.

FIGS. 13*a-b* depict the nucleic acid (FIG. 13*a*) and amino acid (FIG. 13*b*) sequences of hSef-c as determined using the RACE products. Nucleic acids and amino acids from the unique hSef-c domain are labelled in red. The potential initiation Methionine codons are labelled in green. *=termination codon.

FIGS. 14*a-b* depict the nucleic acid (FIG. 14*a*) and amino acid (FIG. 14*b*) sequences of hSef-d as determined using the RACE products. Nucleic acids and amino acids from the unique hSef-d domain are labelled in red. The potential initiation Methionine codon is labelled in green.

FIGS. 15*a-i* depict the expression of hSef in normal human breast and breast cancer. FIG. 15*a*—RT-PCR analysis of hSef A and B isoforms and GAPDH standard using total RNA from normal human breast tissue. n.c.: negative control, template minus. p.c.: positive control using hSefA expression vector as template for amplification. FIGS. 15*b-c*—RNA in-situ hybridization visualizing very strong hSef expression in normal ductal epithelium. FIG. 15*c*—higher magnification of intra-lobular ducts. Ep and F denote epithelial cells and stromal fibroblasts, respectively. FIG. 15*d*—Breast hyperplasia (red arrow) and coexisting low grade ductal carcinoma in situ (black arrow) exhibiting nearly normal hSef levels; FIG. 15*e*—heterogeneous hSef expression in low-grade well differentiated invasive carcinoma; strong expression (black arrow, and inset) in intraductal cancer cells, and very low expression (red arrow) in areas of lower differentiation. FIGS. 15*f-i*—Invasive breast carcinomas harboring low expression or loss of hSef. Low hSef expression in infiltrating ductal carcinoma grade I (FIG. 150, and lack of hSef expression in two cases of infiltrating ductal carcinoma grade II (FIGS. 15*g-h*), and a scirrhous carcinoma grade II (FIG. 15*i*). Arrow in FIG. 15*g* indicates hSef-positive normal duct surrounded by negative cancer tissue. Bars: 100 μm. Magnification in FIGS. 15*b, c-d*, and *f-i* is X160, X45, X25, respectively.

FIGS. 16*a-f* are in situ hybridization analyses depicting down-regulation of hSef in ovarian carcinoma. Strong hSef expression in normal ovarian surface epithelium (OSE, FIG. 16*a*) and epithelial lining of the fallopian tube (FT, FIG. 16*b*). Examples of hSef expression levels in ovarian carcinomas of varying grades including serous papillary cystic adenocarcinoma grade I expressing strong hSef levels (FIG. 16*c*); grade II with moderate (FIG. 16*d*) and grade II with low expression level (FIG. 16*e*); grade III tumor negative for hSef expression. Bars: 25 μm (FIG. 16*a*) and 100 μm (FIGS. 16*b-f*).

FIGS. 17*a-f* are in situ hybridization analyses depicting expression of hSef in normal thyroid gland and thyroid carcinoma. High hSef expression in follicular cells of normal thyroid (FIGS. 17*a, b*). Strong or moderate hSef levels in two cases of low-grade papillary carcinoma (FIGS. 17*c, d*). In FIG. 17*d*, note negative staining (arrow on the bottom right) and moderate hSef signal in areas of higher differentiation (arrow on top left, FIG. 17*d*). Negative hSef staining in papillary (FIG. 17*e*) and follicular (FIG. 170 carcinoma. Bars: 25 μm (FIGS. 17*a-b*); 100 μm (FIGS. 17*c-f*).

FIGS. 18*a-f* are in situ hybridization analyses depicting expression of hSef mRNA in normal prostate and prostate tumors. FIG. 18*a*—Strong hSef expression in glandular epithelium (black arrow) and weaker hSef signal of stromal fibroblasts in normal prostate. FIG. 18*b*—Down-regulation of hSef in BPH; FIG. 18*c*-heterogenous hSef expression in low-grade (GG6) prostate adenocarcinoma. Arrowhead points to a normal gland, and arrows to malignant glands with moderate hSef levels (black arrow) or negative hSef staining (red arrow). FIGS. 18*d-e*—two intermediate grade prostate adenocarcinoma (GG7) with low or negative hSef staining.

FIG. 18*f*—High grade prostate adenocarcinoma negative for hSef expression. Counterstain with Hematoxylin. Bars: 100 p.m.

Figure 19A:
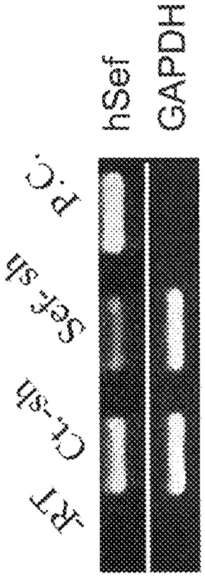
Figure 19B:
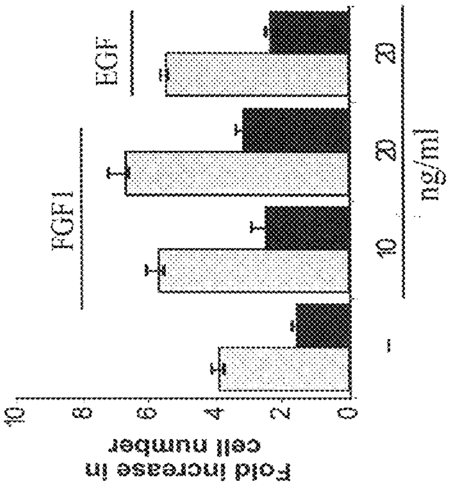

FIGS. 19*a-b* depict that silencing hSef expression enhances cell proliferation. For hSef RNA silencing, HeLa cells were transfected with the pSUPER vector bearing hSef sh-RNA (Sef-sh) or pSUPER containing control sh-RNA (Ct-sh). Mass cultures of resistant cells were prepared as described in Materials and Methods. FIG. 19*a*—RT-PCR analysis of total RNA extracted from transfected cells to determine the extent of hSef silencing. Top panel: hSef, bottom panel: GAPDH. Primers common to hSef isoforms were utilized for amplification (top panel). —RT: first strand was synthesized in the absence of reverse transcriptase; PC: positive control for amplification using hSef expression vector as template. FIG. 19*b*—HeLa cells stably expressing hSef shRNA (shaded bars) or control shRNA (solid bars) were seeded at a density of 25,000 cell/35 mm plate, and 24 hours later cells were washed and grown under serum free conditions in the absence or presence of the indicated growth factors. Growth factors were added every other day, and live cells were counted 5 days post seeding. The error bars indicate standard deviation of 3 independent experiments.

DESCRIPTION OF THE PREFERRED EMBODIMENTS

The present invention is a method of inhibiting solid tumor growth using an agent capable of upregulating the expression level and/or activity of hSef-b in FGF and/or PDGF—induced proliferating cancerous cells, and tumors that overexpress their cognate receptors. Specifically, the present invention can be used to treat cancerous tumors such as ovarian carcinoma, pancreatic cancer, breast cancer, endometrial carcinoma and brain tumors. In addition, the present invention is of methods and kits for diagnosing cancer and selecting an anti-cancer treatment regimen by detecting a decrease in the expression level of Sef in a tissue sample.

The principles and operation of the method of inhibiting solid tumor growth and diagnosing cancer according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Solid tumors account for the majority of human tumors and among them, carcinomas of an epithelial origin, account for over 80%. Conventional cancer therapy is based on chemotherapy drugs (e.g., thymidylate synthase inhibitors, nucleoside analogs, aromatase inhibitors, taxanes and topoisomerase-I inhibitors) which often fail due to the development of drug resistance by the cancerous cells.

Since the growth of solid tumors depends on nutrients and oxygen which are supplied by the tumor vasculature, new approaches of cancer therapy are focused on the inhibition of angiogenesis via the inhibition of receptor tyrosine kinases and their ligands. Thus, various anti-angiogenic agents have been designed and tested in animal models (Boehm et al., 1997; Nature; 390: 404-7; Bergers et al., 1999; Science; 284: 808-12; Klauber N et al. 1997; 57: 81-6). However, the mechanisms by which such agents exert their anti-tumor effect remain unclear (O'Reilly et al., 1997; Oreilly et al., 1996).

Recently, new ligand-induced antagonists of RTK signaling have been discovered. These include the Sprouty and SPRED (Sprouty related EVH1-domain-containing) proteins which suppress the RTK-induced mitogen-activated protein kinase (MAPK) pathway (reviewed in Christofori, G., 2003; Dikic and Giordano, 2003).

Sef (for Similar Expression to FGF genes) is a newly identified antagonist of fibroblast growth factor (FGF) signaling which antagonizes FGF activity during embryogenesis by acting as a feedback-induced antagonist of the Ras/MAPK mediated FGF-signaling (Furthauer, M., et al., 2002; Tsang M., et al., 2002). Sef encodes a putative type I transmembrane protein that is conserved across zebrafish, mouse and human (Yang R B, et al., 2003 and data not shown) but not in invertebrates (Furthauer, M., et al., 2002; Tsang M., et al., 2002; Lin, W., et al., 2002). Subsequent studies showed that the mouse (Kovalenko D, 2003) homologue of zfSef similarly inhibits FGF-induced activation of MAPK, and FGF-induced activation of protein-kinase B (pkB/Akt), a key protein in the phosphatidylinositol-3 (PI3) kinase pathway. On the other hand, the mSef was unable to inhibit PDGF-, EGF- or calf serum-induced phosphorylation of ERK in NIH 3T3 cells (Kovalenko D, 2003). Other studies showed that the human Sef homologue (which is later referred to as hSef-a by the present inventor), is capable of inhibiting FGF- and NGF-induced differentiation of PC12 cells (Xiong et al., 2003; JBC 278: 50273-50282).

FGFs comprise a family of 22 structurally related polypeptide mitogens that control cell proliferation, differentiation, survival and migration, and play a key role in embryonic patterning (14-16). They signal via binding and activation of a family of cell surface tyrosine kinase receptors designated FGFR1-FGFR4 (17-20). Activated receptors trigger several signal transduction cascades including the Ras/MAPK and the PI3-kinase pathway (15, 21). Depending on the cell type, FGF can also activate other MAPK pathways, such that leading to the activation of p38-MAPK (22, 23).

PDGF acts as a potent mitogen of mesenchymal cell proliferation via the two related receptor tyrosine kinases, alpha and beta PDGF receptors and its expression was demonstrated in various solid tumors, such as glioblastomas and prostate carcinomas (Reviewed in George D. 2003; Adv Exp Med. Biol. 532:141-51).

The expression of human Sef in normal and malignant tissues has been controversial. While Yang R B., et al (J. Biol. Chem. 2003, 278:33232-8) found that Sef is expressed a variety of breast cancer tissues, Darby S, (Oncogene. 2006, 25: 4122-7) found that loss of Sef expression is associated with high grade and metastais of prostate cancer only. Thus, to date, cancer diagnosis based on the expression level of Sef has not been suggested. In addition, none of these studies have suggested using Sef expression for staging of cancer, determining disease course and/or cancer prognosis and/or for selecting an anti-cancer therapy regimen.

While reducing the present invention to practice, the present inventor has uncovered three new alternatively spliced isoforms of the human Sef (designated hSefb-d) and demonstrated that hSef-b is uniquely capable of inhibiting FGF and PDGF RTK signaling, inhibiting the growth of cells expressing FGF and PDGF cognate receptors and reducing solid tumor growth. In addition, the present inventor has shown that the expression of hSef is reduced in various solid tumors such as thyroid carcinoma, breast cancer, ovarian cancer and prostate cancer in a manner which correlates with an increase in tumor malignancy. Moreover, the present inventor has demonstrated that overexpression of hSef results in suppression of colony formation and growth of cancerous cells. Thus, the present inventor has uncovered that agents capable of upregulating hSef can be used to inhibit the growth of solid tumors and thereby treat cancer. In addition, the present inventor has uncovered that the decrease in hSef expression can be used as a tool for diagnosing solid tumor, including staging of cancer, determining disease course and/or cancer prognosis and/or for selecting an anti-cancer therapy regimen.

As is shown in FIGS. 1-4 and Examples 1 and 2 of the Examples section which follows, while the hSef-a protein is a heavily glycosylated membrane protein, the hSef-b protein is a cytosolic protein, lacking post-translational glycosylations. Furthermore, the cytosolic isoform of the human Sef protein (hSef-b), but not the transmembrane isoform (hSef-a, See Lin W., et al., 2002) is capable of inhibiting the growth of NIH/3T3 cells via the inhibition of FGF and PDGF signaling pathway (FIGS. 1-2 and 4-12, Table 1 and Examples 1, 3, 4, and 5 of the Examples section which follows). In addition, as is shown in FIGS. 2*a-b* and Example 1 of the Examples section which follows, hSef-b is translated from a Leucine initiation codon instead of a Methionine codon. Such a usage of an alternative translation initiation codon is probably the reason for the relatively low levels of hSef-b obtained following transfection (data not shown). Notwithstanding, hSef-b was found to be more potent in inhibiting RTK-mediated cell proliferation than hSef-a (data not shown). Altogether, these results demonstrate that the unique N-terminal sequence of hSef-b (amino acids 1-10 in SEQ ID NO:6) and/or the lack of secretion signal and/or the intracellular location of hSef-b confer upon this protein (hSef-b) unique properties as a potent inhibitor of RTK-mediated cell proliferation with a wide repertoire of substrates and/or interacting proteins. As is further shown in Table 2 and is described in Example 7 of the Examples section which follows, over-expression of either hSef-a, hSef-b or hSef-c in breast cancer cells resulted colony suppression and growth inhibition. Moreover, as is shown in FIGS. 15-20 and Tables 3-6 and is described in Example 8 of the Examples section which follows, in situ hybridization analyses demonstrated that hSef is downregulated in various solid tumors such as breast cancer, ovarian cancer, prostate cancer and thyroid carcinoma, suggesting that downregulation of hSef is a common mechanism in cancer. Thus, out of a total of 155 primary carcinoma cases that were screened hSef expression was completely lost in 100/155 cases and reduced in the remaining 55 cases.

Thus, according to one aspect of the present invention there is provided a method of inhibiting a growth of a solid tumor in a subject.

As used herein, the phrase “inhibiting a growth” refers to arresting the development, causing the reduction, remission, or regression of a solid tumor, eradicating tumor cells and/or preventing tumor metastasis. Those of skill in the art will be aware of various methodologies and assays which can be used to assess the development of a solid tumor (e.g., biopsy or fine needle aspiration followed by histopathological examination, ultrasound scan, C.T. scan, X-ray, NMR and the like), and similarly, various methodologies and assays which can be used to assess the reduction, remission or regression of the solid tumor.

The phrase “solid tumor” as used herein, refers to an abnormal mass of tissue resulting from excessive cell division. Solid tumors can be benign or cancerous (i.e., with unregulated proliferation). Preferably, the phrase “solid tumor” as used herein relates to an unregulated cancerous tumor including, but not limited to, ovarian carcinoma, pancreatic cancer, breast cancer, endometrial carcinoma, brain tumor, adrenal carcinoma, pituitary cancer, thyroid carcinoma, tonsillar carcinoma, spleen cancer, adenoids cancer, kidney cancer, liver cancer, testis cancer, bladder cancer, colon cancer, prostate cancer, bile duct, lung cancer, stomach cancer, and the like.

The method is effected by administering to the subject an agent capable of upregulating the expression level and/or activity of at least a functional portion of Sef, such a functional portion of Sef being capable of inhibiting RTK-mediated cell proliferation, thereby inhibiting the growth of the solid tumor in the subject.

As used herein, the term “subject” refers to a mammal, preferably a human being (male or female) at any age which is diagnosed with a cancerous solid tumor as described hereinabove or is predisposed to developing such a tumor.

According to preferred embodiments of the present invention the functional portion of Sef encompasses a Sef protein derived sequence (i.e., of any of the hSef isoforms and homologues described herein, preferably hSef-b) which is functional as an RTK receptor antagonist and thus is capable of inhibiting RTK-mediated cell proliferation via the inhibition of activated ERK1/2.

It will be appreciated that since hSef-b (SEQ ID NO:6) lacks the secretion signal and is found entirely in the cytosol, its entire coding sequence (i.e., amino acid 1-707 in SEQ ID NO:6) can potentially contribute to its functional activity (i.e., inhibiting RTK mediated cell proliferation).

Thus, according to preferred embodiments of the present invention the functional portion of Sef is encompassed by the sequence set forth by amino acids 1-707 of SEQ ID NO:6.

Since hSef-a and hSef-b share a large common domain (i.e., amino acids 11-707 of SEQ ID NO:6) of which a large portion is cytosolic [i.e., amino acids 320-739 in SEQ ID NO:5 (hSef-a) which are identical to amino acids 288-707 in SEQ ID NO:6 (hSef-b)], the functional portion of Sef is preferably encompassed by amino acids 288-707 of SEQ ID NO:6.

Additionally or alternatively, based on targeted deletions made using hSef-a DNA constructs (Xiong S., et al., 2003, JBC 278: 50273-50282; Torii S., et al., 2004, Developmental Cell 7:33-44) which demonstrated the presence of domains required for hSef-a activity, it is conceivable that the equivalent sequence in hSef-b would contribute to the functional activity of hSef-b, i.e., inhibiting RTK-mediated cell proliferation. Thus, the functional portion of Sef is preferably encompassed by amino acids 267-707 of SEQ ID NO:6.

Yet additionally or alternatively, since as is mentioned above hSef-b is a more potent inhibitor of RTK-mediated cell proliferation than hSef-a, it is conceivable that the unique sequence of hSef-b (i.e., amino acids 1-10 in SEQ ID NO:6) is likely to contribute to the functional activity of Sef. Thus, according to preferred embodiments of the present invention the functional portion of Sef includes at least amino acids 1-10 of SEQ ID NO:6, more preferably, at least amino acids 1-10 and 267-707 of SEQ ID NO:6, more preferably, at least amino acids 1-10 and 288-707 of SEQ ID NO:6.

It will be appreciated that the method of the present invention can also utilize Sef homologues (identified from other species or other hSef isoforms) which exhibit the above described functional activity.

Preferably, the polypeptide used by the present invention is at least 85%, at least 86%, at least 87%, at least 88%, at least 89%, at least 90%, at least 91%, at least 92%, at least 93%, at least 94%, at least 95%, at least 96%, at least 97%, at least 98%, most preferably, at least 99% homologous (similar+identical) to the polypeptide sequence set forth in SEQ ID NO:6 or to a portion thereof, as determined using the BlastP software available from the NCBI (Hypertext Transfer Protocol://World Wide Web(dot)ncbi(dot)nlm(dot)nih(dot)gov) where gap open penalty equals 11, gap extension penalty equals 1 and matrix is blosum 62.

As used herein, the phrase "RTK-mediated cell proliferation" refers to RTK activation, signaling and/or over-expression which can be either ligand-induced or ligand independent. Non-limiting examples of RTK ligands include FGF, PDGF, NGF, VEGF, insulin, PLGF, c-kit, met and EGF. Ligand independent RTK-mediated cell proliferation is often found in cancerous tumors such as neuroblastoma [e.g., TrkA (Gryz E A and Meakin S O, 2003; Oncogene. 22: 8774-85)], gliomas (Kapoor G S and O'Rourke D M, 2003, Cancer Biol. Ther. 2: 330-42), lung cancer [e.g., c-Met (Ma P C, et al., 2003; Cancer Res. 63: 6272-81)], breast and prostate cancers [e.g., HER2 (Witton C J et al., 2003, J. Pathol. 200: 290-7)].

As is mentioned hereinabove, the present invention preferably targets the RTKs ligands FGF and PDGF. It will be appreciated that activity of other RTK ligands which are capable of inducing cell proliferation via the activation of ERK1/2, can also be inhibited by the various hSef isoforms of the present invention.

It is also highly likely that unique sequences present in splice variants hSef-c (i.e., amino acids 8-49, 9-49 or 28-49 of SEQ ID NO:15) and hSef-d (i.e., amino acids 37-50 of SEQ ID NO:14) are involved in specific RTK-mediated cell proliferation and/or signaling and as such, the present invention also envisages using these sequences in the method of the present invention.

As is mentioned hereinabove, the present method is effected by upregulating the expression level and/or activity of at least a functional portion of Sef.

The term "upregulating" relates to increasing the expression and/or activity of Sef.

Upregulation of Sef can be effected at the genomic level (i.e., activation of transcription via promoters, enhancers, regulatory elements), at the transcript level (i.e., correct splicing, polyadenylation, activation of translation) or at the protein level (i.e., post-translational modifications, interaction with substrates and the like). For example, upregulation can be effected using hormones or their agonists which upregulate Sef transcription or stabilize Sef RNA transcripts as is further described hereinbelow.

Following is a list of agents capable of upregulating the expression level and/or activity of Sef.

An agent capable of upregulating expression level of a Sef may be an exogenous polynucleotide sequence designed and constructed to express at least a functional portion of the Sef protein. Accordingly, the exogenous polynucleotide sequence may be a DNA or RNA sequence encoding a Sef molecule, capable of inhibiting RTK ligand-induced cell proliferation.

The entire coding region of Sef has been cloned from Zebrafish, mouse, human and chicken and partial cDNA clones are also available from bovine. Thus, coding sequences information for Sef is available from several databases including the GenBank database available through Hypertext Transfer Protocol://World Wide Web(dot)ncbi (dot)nlm(dot)nih(dot)gov/.

To express exogenous Sef in mammalian cells, a polynucleotide sequence encoding Sef (SEQ ID NO:6) or a functional portion of Sef (amino acids 1-707 of SEQ ID NO:6 or a portion thereof) is preferably ligated into a nucleic acid construct suitable for mammalian cell expression. Such a nucleic acid construct includes a promoter sequence for directing transcription of the polynucleotide sequence in the cell in a constitutive or inducible manner.

It will be appreciated that the nucleic acid construct of the present invention can also utilize Sef homologues encoding polypeptides which exhibit the desired activity (i.e., inhibiting RTK-mediated cell proliferation). Such homologues can be, for example, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO:4 or a portion thereof, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tet off system (Shockett, P., Difilippantonio, M., Hellman, N. & Schatz, D. G. (1995) *Proc. Natl. Acad. Sci. U.S.A.* 92: 6522-6526).

The nucleic acid construct (also referred to herein as an "expression vector") of the present invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of Sef mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, PLNCX (a virus shuttle vector), pAV009/A$^+$, pMTO10/A$^+$, pMAMneo-5, baculovirus pDSVE, and any other vector allowing expression of proteins under the direction of the SV-40 early promoter, SV-40 late promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, kidney cells may be targeted using the heterologous promoter present in the baculovirus *Autographa californica* nucleopolyhedrovirus (AcMNPV) as described in Liang C Y et al., 2004 (Arch Virol. 149: 51-60) and ovarian cancer cells may be targeted using a recombinant adeno-associated virus-2 (rAAV) as described by Mahendra G, et al. [Cancer Gene Ther. 2004 Sep. 10, Epub ahead of print, 2005 January; 12(1):26-34].

Recombinant viral vectors are useful for in vivo expression of Sef since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into the targeted cells (i.e., the cancerous cells of the solid tumor). Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

An agent capable of upregulating Sef may also be any compound which is capable of increasing the transcription and/or translation of an endogenous DNA or mRNA encoding the Sef polypeptide and thus increasing endogenous Sef activity. For example, FGF was found to increase Sef transcripts in chick embryos (data not shown and Ron D., ASBMB annual meeting, Boston, Jun. 12-16, 2004). In addition, as determined by RT-PCR analysis, various hormones such as FSH and LH-like hormones are capable of upregulating Sef transcription in mice ovary (data not shown). It will be appreciated that many other hormones or growth factors such as androgens, TSH, PDGF, NGF, insulin, and/or VEGF are highly likely to upregulate Sef transcription, RNA stability, translation and/or activity.

Thus, according to preferred embodiments of the present invention, the upregulating agent used by the present invention a growth factor and/or a regulating hormone.

An agent capable of upregulating Sef may also be an exogenous polypeptide including at least a functional portion (as described hereinabove) of the Sef protein. Methods of identifying such exogenous polypeptides are known in the art (Torii S, et al., 2004; Developmental Cell 7: 33-44; Tsang et al., 2002).

Upregulation of Sef can be also achieved by introducing to the subject at least one Sef substrate. Non-limiting examples of such agents include hormones such as FSH and LH which can be administered orally, intravenously or locally directly to the tumor tissue to thereby upregulate Sef expression level and/or activity within specific tumor cells.

It will be appreciated that since FGFR is expressed in many types of tumors, FGF and Sef (or an expression vector encoding same) can be co-administered to the subject to facilitate and/or improve Sef activity in reducing and/or inhibiting tumor growth.

It will be appreciated that the differential expression of the various hSef isoforms (see Examples 2 and 6 of the Examples section which follows) may suggest the use of tissue-specific Sef isoforms for the inhibition of tissue-specific tumor growth. For example, upregulation of hSef-b in a tissue where it is usually not expressed (e.g., adrenal or ovary) or moderately expressed (e.g., testes) can lead to efficient inhibition of tumor growth and subsequent treatment of the cancer and/or cancer metastases.

Each of the upregulating agents described hereinabove or the expression vector encoding Sef or a functional portion thereof can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the upregulating agent or the expression vector encoding Sef or a functional portion thereof which are accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (the upregulating agent or the expression vector encoding Sef) effective to prevent, alleviate or ameliorate symptoms of a disorder (e.g., inhibit tumor growth) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (See e.g., Fingl, et al., 1975, in "The Pharmacological Basis of Therapeutics", Ch. 1 p. 1).

Dosage amount and interval may be adjusted individually to provide plasma levels of the active ingredient are sufficient to inhibit tumor growth (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Thus, the teachings of the present invention can be used to treat individuals having a cancerous tumor (e.g., a solid tumor in the kidney) and/or a cancerous metastases. For example, an expression vector (e.g., a viral vector) including a polynucleotide sequence encoding the human Sef-b mRNA (SEQ ID NO:4) and the suitable promoter sequences to enable expression in kidney cells is introduced into the individual via intravenous administration. Expression of such a vector in the kidney is expected to upregulate the expression level and/or activity of Sef in this tissue and thus to inhibit FGF and/or PDGF-induced cell proliferation in the tumor cells. Dosage of such an expression vector should be calibrated using cell culture experiments and animal models. Success of treatment is preferably evaluated by determining the tumor size (using for example C.T. scans) and the individual general health status.

It will be appreciated, that if such a treatment is employed early following the detection of a cancerous tumor, it may prevent the complications associated with tumor growth (e.g., metastases) and thus improve the individual's prognosis and quality of life.

It will be appreciated that the agent of the present invention (which increases the transcription, translation and/or activity of Sef), can be identified using a variety of methods known in the art. For example, cells expressing low levels of endogenous Sef (e.g., NIH 3T3 cells) can be cultured in 10-cm dishes in the presence of a culture medium (e.g., DMEM medium) supplemented with serum (e.g., 10% newborn calf serum). To identify a potential agent which upregulates the transcription, translation and/or activity of Sef, various transcription factors, drugs and molecules such as hormones (e.g., FSH and LH-like hormones) can be added to the culture medium for an incubation period which is expected to cause upregulation of transcription, translation and activity. As is shown in FIGS. 9*a-b*, such incubation period can vary between minutes to hours, and it is within the capabilities of those skilled in the art to determine the suitable incubation periods.

Since the functional portion of Sef is included in the intracellular fraction (see Example 1 of the Examples section which follows), the effect of the agent on Sef expression levels and/or activity of Sef is preferably determined by analyzing the cells and not the cell medium. Thus, the cells are collected and centrifuged, the medium is discarded and the cell pellet is further subjected to RNA and/or protein detection methods.

Alternatively, the anti-mitogenic activity of Sef (see Example 3 of the Examples section which follows) can be measured by determining the level of DNA synthesis in such cells (a mitogenic assay), or counting cell number as a measure for Sef effect on proliferation.

Following is a list of methods useful for detecting Sef RNA level in cells.

Northern Blot analysis: This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR analysis: This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers [e.g., the forward and reverse hSef-b primers (SEQ ID NOs:2 and 1, respectively)] and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA in situ hybridization stain: In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The probe can be for example an RNA-oligonucleotide probe (e.g., a 5'-biotinylated 2-O-methyl RNA oligonucleotide) which is synthesized according to a selected sequence from the unique 5' region of hSef-b (i.e., nucleic acids 1-240 as set forth in SEQ ID NO:7). The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

In situ RT-PCR stain: This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Oligonucleotide microarray: In this method oligonucleotide probes capable of specifically hybridizing with the polynucleotides of the present invention (i.e., human Sef RNA) are attached to a solid surface (e.g., a glass wafer). Each oligonucleotide probe is of approximately 20-25 nucleic acids in length. To detect the expression pattern of the polynucleotides of the present invention in a specific tissue sample (e.g., a breast tissue), RNA is extracted from the tissue sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

Following is a list of immunological detection methods which can be used to detect the level of Sef protein in cells.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis. In addition, using phospho-specific antibodies, this method allows the determination of the activation state of specific proteins [e.g., P-p38 or P-ERK1/2 (see Example 4 of the Examples section which follows)].

Radio-immunoassay (RIA): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate (i.e., Sef) in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

It will be appreciated that Sef activity (i.e., inhibition of RTK ligand-induced proliferation and/or downregulation of the over-expressed RTK receptors via the inhibition of P-ERK1/2) can be detected as described in details in Examples 3-5 of the Examples section which follows.

Thus, the agent of which addition to the cells results in upregulation of the expression level and/or activity of endogenous Sef in the cells is identified as a potential upregulating agent and can be used to inhibit tumor growth in the subject.

As is mentioned hereinabove and is described in Example 8 of the Examples section which follows, hSef expression was significantly downregulated and/or completely lost in various solid cancerous tumors, in a manner which correlates with tumor invasiveness and/or malignancy. Thus, a decrease in the expression level of hSef in a tissue of a solid tumor as compared to a normal, unaffected tissue (i.e., devoid of cancer) which is derived from either an unaffected subject or from the same subject in need of diagnosis (e.g., a mammary tissue devoid of cancer) can be used to determine the presence and/or degree of malignancy of solid tumors and thus diagnose cancer.

Thus, according to another aspect of the present invention there is provided a method of diagnosing cancer in a subject in need thereof. The method is effected by detecting in a tissue sample of the subject an expression level of Sef, wherein a decrease in the expression level of the Sef compared to the expression level of the Sef in an unaffected tissue sample is indicative of the cancer, thereby diagnosing the cancer in the subject.

As used herein the term “diagnosing” refers to classifying a disease or a symptom, determining a severity of the disease, monitoring disease progression, forecasting an outcome of a disease and/or prospects of recovery. Preferably, the term “diagnosing” as used herein also encompasses determining a malignancy of the solid tumor, e.g., determining course of disease, cancer staging, invasiveness and/or metastatic stage (e.g., presence or absence of cancer metastases). It will be appreciated that determining the course of disease (e.g., a highly malignant cancer which develops fast or a slow growing cancer) as well as forcasting the outcome of the disease (e.g., prognosis) can be used to determine the type and/or dosage i.e., regimen of the anti-cancer therapy used to treat the subject in need.

For example, a significant downregulation of Sef expression (e.g., a complete loss of Sef expression) in a relatively small-size tumor (e.g., a breast tumor of less than 0.5-1 cm) may indicate the presence of highly malignant and/or highly aggressive cancerous cells which may result in a fast growing tumor and/or highly metastatic cancer. On the other hand, a moderate downregulation of Sef expression in a moderate-size tumor may indicate the presence of a less aggressive, slow growing cancer. Additionally or alternatively, downregulation of Sef in cancerous cells along with overexpression of an oncogene such as c-erb, and/or downregulation of the expression level of another tumor suppressor gene may indicate the degree of cancer malignancy and/or aggressiveness. Thus, the choice of treatment can be selected according to the degree of malignancy and/or aggressiveness of cancer as determined by Sef expression alone and/or in combination with other known cancer diagnostic markers (e.g., HER-2, P53, ER, PR).

As used herein the phrase a “subject in need thereof” refers to a mammal, preferably a human being (male or female) at any age which is in need of diagnosis of a solid tumor. Such a subject can be predisposed to develop a solid tumor due to a mutation in an oncogene or a tumor suppressor (e.g., a carrier of a mutation in BRCA1, BRCA2, P53), family history of cancer (e.g., having a first degree relative with cancer) and/or exposure to environmental hazard (e.g., DNA damaging agents, carcinogens, irradiation). Additionally or alternatively, such a subject is suspected to have a solid tumor based on abnormal physical findings (e.g., a suspicious lump, a cyst and the like) observed using endoscopy (e.g., colonoscopy), physical examination and/or a suspicious imaging finding (e.g., obtained by ultrasound, X-ray, CT scan or MRI).

The cancer which is diagnosed by the method according to this aspect of the present invention can be any type of cancer in which Sef expression is down-regulated. Non-limiting examples of cancers which can be diagnosed according to the method of this aspect of the present invention include cancer of epithelial origin, cancer of mesenchymal origin (e.g., sarcoma) or cancer of the nervous system (e.g., brain tumor, glial and astrocyte tumors). For example, such a cancer can be breast cancer, ovarian cancer, thyroid carcinoma, prostate cancer, brain cancer, colon cancer, skin cancer, pancreatic cancer, endometrial carcinoma, adrenal carcinoma, pituitary cancer, tonsillar carcinoma, spleen cancer, adenoids cancer, kidney cancer, liver cancer, testis cancer, bladder cancer, bile duct, lung cancer and stomach cancer.

Preferably, the cancer is a solid tumor cancer. It will be appreciated that the solid tumor can be a primary solid tumor (i.e., a tumor which is located in the place where the cancer started) as well as a secondary solid tumor [i.e., a tumor that forms as a result of spread (metastasis) of cancer from its site of origin].

The phrase "tissue sample" as used herein refers to any sample of a tissue derived from a subject (e.g., a tissue in which cancer is suspected), including but not limited to, for example, a mammary tissue (breast tissue), an ovary tissue, a thyroid tissue, a prostate tissue, as well as other tissues such as a brain tissue, a skin tissue or colon tissue. The sample of the tissue can be a tissue biopsy, fine needle aspiration and/or core needle biopsy which can be derived by any known surgical mean such as using a scalpel or a needle.

As used herein the phrase "unaffected tissue sample" refers to a tissue sample of the same type as the test tissue (i.e., a tissue which is subject to diagnosis according to the method of the present invention, e.g., with a suspected solid tumor) which is devoid of any solid tumor. Such a tissue sample can be derived from a healthy, unaffected individual or from the same subject however from a healthy tissue. For example, if a mammary tissue derived from a left breast of a female is suspected to have a solid tumor, the unaffected tissue sample can be a mammary tissue derived from the right breast of the same female subject. Additionally or alternatively, the unaffected tissue can be derived from the same breast of the suspected tumor but from a location that is suspected to be free of cancer cells.

As is shown in FIGS. 4*a-c* and 15*a-c* and is described in Examples 2 and 8 of the Examples section which follows, human Sef splice isoforms exhibit a tissue specific expression pattern. Thus, while human Sef-a is highly expressed in normal human breast, brain, pituitary, tonsils, spleen, adenoids, fetal kidney, liver, testes and ovary, and moderately expressed in primary aortic endothelial cells, human umbilical vein endothelial cells (HUVEC) and adrenal medulla; human Sef-b is highly expressed in thyroid and testes; moderately expressed in pituitary, fetal brain and HUVEC cells and not expressed (negative) in normal human breast tissue. As the pattern of expression is known, a reduction of the expression level of a specific Sef isoform may indicate the presence of cancer. For example, a decrease in the expression level of human Sef-a in a breast tissue or an ovary tissue of the subject who is suspected to have cancer is indicative of the diagnosis of cancer in the subject. Similarly, a decrease in the expression level of human Sef-b in a thyroid tissue of the subject who is suspected to have cancer is indicative of the diagnosis of cancer in the subject.

Diagnosis of the cancer (e.g., solid tumor) according to the method of this aspect of the present invention is performed by detecting a decrease in the expression level of Sef in a tissue sample of the subject. Such a decrease can be in the Sef amino acid sequence of the tissue (e.g., the amino acid sequence as set forth by SEQ ID NO:5 or 6) or in the Sef nucleic acid sequence of the tissue (e.g., the nucleic acid sequence as set forth by SEQ ID NO:4, 8, 9 or 10). Detecting the expression level of Sef can be performed using any RNA detection method and/or a protein detection method. Non-limiting examples of RNA detection methods which can be used along with the method of this aspect of the present invention include Northern blot analysis, RT-PCR, RNA in situ hybridization, in situ RT-PCR and RNA microarrays as further described hereinabove and in the Examples section which follows. Non-limiting examples of protein detection methods which can be used along with the method of this aspect of the present invention include Western blot analysis, immunohistochemistry, immunofluorescence, radio immuno assay and FACS analysis as further described hereinabove.

It will be appreciated that prior to detecting the expression level of Sef in the tissue sample, the tissue sample is preferably processed and treated according to the desired detection method. For example, for in situ (i.e., within the cell or tissue where Sef is naturally expressed) detection of Sef expression level (using e.g., RNA in situ hybridization, in situ RT-PCR, immunohistochemistry or immunofluorescence), the tissue sample is preferably processed to enable tissue sectioning (e.g., paraffin-embedded sections, cryosections). Such processing may include, fixation (e.g., using formaline, paraformaldehyde), treatment with various agents which facilitate detection of nucleic acids in the tissue (e.g., hydrogen peroxide, proteases such as proteinase K) or with agents facilitating detection of specific polypeptides while preventing non-specific binding of antibodies (e.g., anti-Sef antibody) to the tissue sample (e.g., by blocking the tissue with a blocking agent such as serum, milk). Alternatively, detection of Sef expression level can be performed on isolated nucleic acid sequences (i.e., RNA molecules, e.g., mRNA) or proteins which are extracted from the tissue. It will be appreciated that for such applications the tissue is preferably a freshly obtained, non-fixed tissue. Methods of extracting RNA or proteins from tissue samples are well known in the art.

Preferably, detection of Sef nucleic acid sequence (using any of the RNA detection methods described hereinabove) can be performed using a reagent such as an isolated nucleic acid sequence capable of specifically hybridizable to Sef nucleic acid sequence [e.g., a nucleic acid sequence which is complementary (i.e., by means of hydrogen bonding] to the nucleic acid sequence of Set). A non-limiting example of such an isolated nucleic acid sequence is described in Example 8 of the Examples section which follows and is set forth by SEQ ID NO:31.

The term "isolated nucleic acid sequence" includes oligonucleotides composed of naturally-occurring bases, sugars and covalent internucleoside linkages (e.g., backbone) as well as oligonucleotides having non-naturally-occurring portions which function similarly to respective naturally-occurring portions.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

Specific examples of preferred oligonucleotides useful according to this aspect of the present invention include oligonucleotides containing modified backbones (e.g., those that retain a phosphorus atom in the backbone) or non-natural internucleoside linkages, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C). Further base modifications include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

It will be appreciated that the isolated nucleic acid sequence of the present invention can be of any size, e.g., from 10-40 nucleic acids to about 100-300 nucleic acids or even 1000-3000 nucleic acids in length.

Preferably, for the specific hybridization of the isolated nucleic acid sequence with Sef, the isolated nucleic acid sequence is of at least 25, at least 50, at least 75, at least 100, at least 150, at least 250, at least 350 bases.

It will be appreciated that for certain detection methods (e.g., an oligonucleotide microarray as is further described hereinbelow), the isolated nucleic acid sequence of the present invention is preferably bound to a solid support, such as a solid surface (e.g., a glass wafer) as is further described hereinunder. Usually the solid support is a microsphere (bead), a magnetic bead, a nitrocellulose membrane, a nylon membrane, a glass slide, a fused silica (quartz) slide, a gold film, a polypyrrole film, an optical fiber and/or a microplate well.

As is further described hereinunder, the isolated nucleic acid sequence of the present invention can be labeled. Various methods can be used to label the isolated nucleic acid sequence of the present invention. These include fluorescent labeling with a fluorophore conjugated via a linker or a chemical bond to at least one nucleotide, or the use of a covalently conjugated enzyme (e.g., Horse Radish Peroxidase) and a suitable substrate (e.g., o-phenylenediamine) which upon interaction therebetween yields a colorimetric or fluorescent color. Thus, the isolated nucleic acid sequence can be radiolabeled, Digoxigennin labeled and/or biotinylated using e.g., in vitro transcription in the presence of labeled nucleotides.

Preferably, the expression level of Sef amino acid sequence can be detected using a protein detection method with an antibody or antibody fragment which comprises an antigen recognition region capable of specifically binding to Sef amino acid sequence (e.g., as set forth by SEQ ID NO:5 or 6).

The term "antibody" as used in this invention includes intact antibody molecules as well as functional fragments thereof, such as Fab, F(ab')2, Fv or single domain molecules such as VH and VL to an epitope of an antigen. As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics. The functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

It will be appreciated that for certain detection methods as described hereinunder, the antibody or antibody fragment is bound to a solid support (such as nylon filters, glass slides or silicon chips) using methods which are well known in the art.

Preferably, for detecting Sef nucleic acid sequence the antibody or antibody fragment is labeled (e.g., radiolabeled, biotinylated or fluorescent labeling) using methods known in the art.

The agents of the present invention which are described hereinabove for detecting expression level of Sef nucleic acid sequence or amino acid sequence may be included in a diagnostic kit/article of manufacture preferably along with appropriate instructions for use and labels indicating FDA approval for use in diagnosing cancer.

Such a kit can include, for example, at least one container including at least one of the above described diagnostic agents (e.g., reagents such as the isolated nucleic acid sequence and/or the antibody or antibody fragment) and an imaging reagent packed in another container (e.g., HRP, alkaline phosphatase, fluorescently-labeled secondary antibodies, buffers, chromogenic substrates, fluorogenic material). The kit may also include appropriate buffers and preservatives for improving the shelf-life of the kit. Most preferably, the kit can include the addressable oligonucleotide microarray (DNA chip) described hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Material and Experimental Methods

Enzymes, growth factors, reagents and chemicals—Restriction enzymes and Taq-polymerases were from NEB (Beverly, Mass.), Pharmacia (Amersham Pharmacia Biotech LTD, UK) and Roche (Indianapolis, Ind., USA). Purified recombinant FGF2 was produced as described (24-26). Bovine brain FGF1, recombinant human FGF4, epidermal growth factor (EGF) and platelet derived growth factor (PDGF) were from R&D Systems (R&D Systems Inc, Minneapolis, Minn., USA). [$^{35}$S]-Methionine (1000 Ci/mmol) and [$^{3}$H]-Thymidine (25 Ci/mmole) were from Amersham HVD Biotech. Fibronectin, fetal and newborn calf serum and media were from Biological Industries (Beth Ha'emek, Israel, Israel) or Gibco-Laboratories (Grand Island, N.Y., USA). Fluoromount-GTM was from Southern Biotechnology Associates, Inc. (Birmingham, Ala., USA). BSA was from ICN (UK). All other chemicals were from Sigma (St Louis, Mo.).

cDNA cloning and plasmid construction—RT-PCR was utilized to amplify the entire coding region of hSef-a from human brain or fibroblast RNA, and of hSef-b from testes RNA. First strand cDNA was synthesized using the following primer: 5'-AGTGGCAATGCTTAGACTCTTTCGT-3' (SEQ ID NO:1) which is designed according to the 3' un-translated region (UTR) of a partial hSef EST clone (GenBank Accession No. AL133097, i.e., a common primer for both hSef-a and b isoforms). Amplification of the coding region of hSef-b was performed with nested primer: 5'-GAGGATCCAAGCTTTGTTACAAAGGGGCGACCGCGT-3' (SEQ ID NO:3), and a primer flanking the amino terminal part unique to the hSef-b isoform: 5'-GCGTGCCAGACAGAGTGCTAGGCAT-3' (SEQ ID NO:2) which is designed according to the Testes EST clone GenBank Accession No. BG721995 and is located at the unique 5' sequence of hSef-b (nucleic acids 426-150 of SEQ ID NO:7; This clone was served as a platform to reconstruct hSef-a cDNA containing its entire ORF. Thus, the 5' portion of hSef-a was amplified from human brain or normal fibroblasts using a primer unique to hSef-a: 5'-GAGGATCCTGACGGCCATGGC CCCGTGGCTGCAGCTC-3' (SEQ ID NO: 16, which is designed according to the EST clone GenBank Accession No. BE750478 and is located at the unique 5' sequence of hSef-a (nucleic acids 1-37 of SEQ ID NO:10), and a primer common to both Sef isoforms (SEQ ID NO:3). This fragment was digested with BamH1 following sequence verification and ligated to the remainder of hSef-a sequences. The cDNA of hSef-a or hSef-b was cloned into pcDNA3.1, pTET splice and pcDNA3.1/myc-His expression vectors (Invitrogen).

Analysis of the expression pattern of hSef transcripts—Total RNA was extracted from human tissues and cell lines as described elsewhere (19). Two μg of total RNA were used for first strand synthesis with random hexamer primers. RT-PCR was performed with primers specific to the common region (SEQ ID NO:11 and SEQ ID NO:18); the hSef-a (SEQ ID NO:16 and SEQ ID NO:17); the hSef-b (SEQ ID NO:2 and SEQ ID NO:17); the hSef-c (SEQ ID NO:20 and SEQ ID NO:19); and the GAPDH transcript (SEQ ID NO:12 and SEQ ID NO:13). Amplification was performed in a solution of 1 μM of each oligonucleotide primer, 0.2 mM of each dNTPs, 50 mM KCl, 2 mM $MgCl_2$, 1 mM β-mercoptoethanol, 25 mM TAPS pH 9.3 and 0.02 units of Super-Therm polymerase in a total volume of 25 μl. After pre-denaturation at 95° C. for 5 min, the reaction mixture was incubated as follows: 30 sec at 94° C., 30 sec at 65° C., and 2 min at 72° C. for 25 (GAPDH), 35 (hSef-a and hSef-b) or 40 (hSef-c) cycles. 5 μl of each reaction were analyzed by gel electrophoresis on 1.8% agarose gels in TAE buffer (40 mM Tris-acetate, 1 mM EDTA) and stained with ethidium bromide. The PCR products of the amplification with hSef-c specific primers were separated by electrophoresis on 3% Nusieve-agarose gels (3% Nusieve GTC agarose, 1% Seakem LE agarose in TBE buffer) in TBE buffer (45 mM Tris-Borate, 1 mM EDTA).

Cell Cultures—HEK 293 and NIH/3T3 cells were grown in Dulbecco's modified Eagle's medium (DMEM) containing 10% fetal bovine serum or newborn calf serum, respectively.

Transient transfections of HEK 293 cells—Transient transfections of HEK 293 cells were performed using Lipofectamine Plus in Opti-MEM (Invitrogen). For co-immunoprecipitation (CO-IP) assays the cells were transiently transfected with hSef-a or hSef-b in the presence or absence of FGFR1. Briefly, cells were cultured in 6-cm dishes and were transfected with 3 μg of each FGFR1 and hSef-a plasmids (for hSef-a/FGFR1 CO-IP) or cells (in 10-cm dishes) were transfected with 4 μg of FGFR1 and 12 μg of hSef-b plasmids (for hSef-b/FGFR1 CO-IP).

Stable transfections in NIH/3T3 cells—Stable transfections were performed using calcium-phosphate, essentially as described in Ron, D. et al., 1988 (27). Tet-off NIH3T3 cells [S2-6 cells, a gift from Dr. David. G. Schatz (28)] were cultured in histidine-deficient DMEM containing 0.5 mM L-histidinol, serum, and 1 μg/ml tetracycline (tet). HSef-b Tet-off NIH/3T3 cell lines were established by co-transfection of the S2-6 cells with pTet splice-hSef-b or the same vector without the insert (i.e., an empty vector) and pTK-Hyg (Clontech) followed by selection in complete medium plus 150 μg/ml hygromycin. Colonies of resistant cells were isolated 3 weeks post transfection.

Cell Growth and Apoptosis Assays—[$^3$H]-thymidine incorporation assay was done in 96-well microtiter plates as described elsewhere (24, 26). Confluent cultures were growth arrested in 0.3% serum for 24 hours, and when indicated, tet was removed 24 hours prior to serum (10%) or growth factors stimulation. For apoptosis studies, the control cells (S2-6) or S2-6/hSef-b cells were grown for 48 hours in the presence or absence of tet. The level of apoptosis was detected using the In Situ Cell Death detection kit (TUNEL staining, Roche Molecular Biochemicals) followed by a confocal microscopy examination.

In vitro translation of the hSef-b construct (pcDNA3.1/Hygro-hSef-b)—In vitro translation of hSef-b was performed using TnT Quick Coupled Transcription/Translation System in the presence of [$^{35}$S]-methionine according to manufacturer's instructions (Promega). Translation products were analyzed by SDS-PAGE and visualized using Phospho-imaging.

hSef antibodies—Polyclonal antibodies against hSef were generated by injecting rabbits with a polypeptide containing the last 402 residues of hSef fused to the amino-terminal portion of Bactriophage a T7 θ10 protein as described in Studier, F W et al., 1990 (29).

CO-IP and immunoblotting—were performed essentially as described elsewhere (30). Briefly, for CO-IP, cells were lysed 24 hours post transfection in HTNG buffer (20 mM HEPES, pH 7.4, 150 mM NaCl, 10% glycerol, 1% Triton X-100, 1 mM EGTA, 1 mM $NaVO_4$ and protease inhibitors). After incubation with antibody, immunocomplexes were captured on Protein G Dynabeads (Dynal), and washed with HTNG buffer. Following SDS-PAGE and immunoblotting, bound antibodies were visualized by chemiluminescence.

Immunofluorescence analysis—Transfected HEK 293 cells were fixed 48 hours post transfection with 4% paraformaldehyde, and incubated in PBS containing 1% BSA, 0.1% saponin and were subjected to immunostaining using the anti-myc (α-myc) antibody (anti-myc epitope, 9E10, Santa Cruz, Santa Cruz, Calif.) or the anti-human Sef antibody (α-hSef). Nuclear staining was done using 10 μM DRAQ5 (Biostatus limited, Shepshed, Leicestershire, UK). Examination of the immunofluorescent staining was performed using the MRC-1024 laser confocal microscope (BioRad, Hercules, Calif.).

Antibodies used in Western Blot and immunoprecipitation analysis—Commercial antibodies were obtained from various suppliers. The anti-myc epitope (9E10), p38, MEK, Akt, CDK4 and FGFR1 (H-76) rabbit polyclonal antibodies were from Santa Cruz; the phospho-p44/42 MAP kinase [Thr202/Tyr204], E10 mouse monoclonal antibodies (NEB), Phospho-Akt [Ser473], phospho-p38, peroxidase conjugated-goat anti-rabbit or anti-mouse IgG were from Sigma; the cyclin D1 and phospho-MEK were from Cell Signaling (Arundel, Australia); the FITC conjugated-Goat anti-rabbit IgG was from ICN; the Rhodamine-RedTM-x-conjugated Affinipure goat anti-mouse IgG was from Jackson Immunoresearch (West Grove, Pa., USA). The ERK-2 rabbit polyclonal antibodies was a gift from Dr. Y. Granot, Ben Gurion University, Israel.

Example 1

Cloning of the Human Sef-b Isoform

Experimental Results

Database search revealed the presence of additional human Sef isoforms—A database search with the zfSef sequence revealed an expressed sequence tag (EST clone AL133097) containing the entire 3'-UTR of hSef and most of its coding region except for the first 170 residues. The remainder of the coding region was obtained by searching the human genome database for upstream exons of hSef and based on homology with bovine Sef (EST clone BE750478). A cDNA fragment encoding the entire open reading frame (ORF) of hSef was amplified from primary human fibroblast or human fetal brain RNA (FIG. 1*a* and data not shown). Human Sef has been mapped to a single locus on chromosome 3p14.3 (data not shown). Further database searches with the amino-terminal sequence of hSef revealed an EST clone from human testes that was 577 nucleotides long and contained an ORF of 122 residues. This EST clone differed from the original hSef in its amino-terminal and the upstream 5'-UTR sequences. Since the human genome contains a single Sef locus, these findings suggest the existence of alternatively spliced Sef isoforms.

Cloning of the human Sef-b isoform—To examine the possibility of additional hSef isoforms, an RT-PCR analysis was performed as follows: first strand was synthesized using a complementary to the 3' UTR of hSef (SEQ ID NO:1), Amplification was performed with primers set forth by SEQ ID NOs:3 and 2. A single product of 2214 nucleotides was obtained (SEQ ID NO:4), confirming the existence of alternate isoforms of hSef (designated hSef-a and hSef-b for the brain and testes isoforms, respectively).

Identification of the hSefb using RACE analysis—The present inventor also identified the hSef-b common and unique sequences using the RACE protocol on human keratinocytes RNA with three consecutive primers designed according to the common region (e.g., SEQ ID NO:17). The experimentally sequence obtained using the RACE protocol is provided in SEQ ID NO:22.

Human Sef-b isoform contains alternative N-terminal amino acid residues—As is schematically illustrated in FIG. 1, while the human Sef-a isoforms contains an ORF of 739 residues (SEQ ID NO:5), the human Sef-b contains an ORF of 707 amino acid residues (SEQ ID NO:6), of them the last 697 residues (i.e., amino acids 11-707 of SEQ ID NO:6) are identical in both isoforms. These results demonstrate the presence of alternative splicing in the human Sef gene resulting in the substitution of the first 42 amino acid residues of hSef-a ORF with 10 new residues of the hSef-b ORF.

Human Sef-b isoform lacks a secretion signal—Similar to hSef-a, the new isoform contains 8 potential N-linked glycosylation sites, a potential transmembrane spanning domain and tyrosine phosphorylation site, immunoglobulin and IL-17 receptor like domains (FIG. 1). Unlike hSef-a which contains a signal for secretion amino acid residues 1-34 as set forth by SEQ ID NO:5; FIG. 1, marked by a star (*) and the sequence which appears left to the arrow], the hSef-b isoform lacks such a signal (FIG. 1), suggesting that it is not a secreted or trans-membrane protein.

Human Sef-b isoforms contains a putative CUG translation initiation codon Interestingly, the unique hSef-b region exhibits a CUG initiation codon. The next putative initiation codon (AUG) is located within the region that is identical in both isoforms. Thus, while translation from the CUG codon is expected to result in a protein of 707 amino acids with a predicted molecular weight of 78 kDa, translation from the AUG codon is expected to result in a protein of 595 residues and a predicted molecular weight of 65 kDa.

The hSef-b isoform uses the CUG translation initiation codon in vitro and in HEK 293 cell cultures—To characterize the hSef-b product and elucidate whether the alternative initiation codon in hSef-b can serve as a translation start site, a cDNA fragment encoding the entire ORF of hSef-b (SEQ ID NO:4) was subcloned into the either pcDNA3.1/Hygro or in pcDNA3.1/myc-His(+)B eukaryotic expression vector (Invitrogen) which contains the myc epitope-tag at the carboxyl terminus of the recombinant hSef-b coding sequence allowing the detection of the translation product with the α-myc antibody. As is shown in FIG. 2*a*, expression of the pcDNA3.1/myc-His-hSef-b DNA construct in HEK 293 cells revealed a single protein product with a molecular weight of about 80 kDa. Similarly, when the hSef-b cDNA was cloned into the pcDNA3.1/Hygro vector (Invitrogen) and was subjected to an in vitro transcription-translation in the presence of [$^{35}$S]-methionine, a major product with a similar molecular weight (~80 kDa) was obtained (FIG. 2*b*). These findings strongly suggest that the CUG codon functions as a major translation start site in the hSef-b isoform.

Human Sef-b is a putative intracellular protein—As is mentioned hereinabove, and depicted in FIG. 1, both hSef isoforms have 8 potential N-linked glycosylation sites. Thus, although hSef-a has a predicted size of 83 kDa, when the coding sequence of hSef-a was expressed in HEK 293 cells, a broad band with an average molecular weight of 120 kDa was observed (FIG. 2*a*), suggesting massive post-translational glycosylations. On the other hand, the similarity between the apparent (80 kDa, FIG. 2*a*) and the predicted (i.e., 78 kDa) molecular weight of hSef-b suggests that the hSef-b isoform does not undergo any significant post-translational modifications. To test the hypothesis that hSef-b, unlike hSef-a, is not subjected to post-translational glycosylations, transfected HEK 293 cells were treated with tunicamycin, an inhibitor of N-linked glycosylation, and the molecular weight of the recombinant proteins was examined on an SDS-PAGE. While tunicamycin treatment resulted in a reduced molecular weight of the hSef-a isoform, such a treatment had no effect on the molecular weight of the hSef-b product (data not shown).

Altogether, these results indicate that hSef-a, but not hSef-b, is a glycoprotein synthesized in the classical secretory pathway, and further suggest that the hSef-b product is an intracellular protein.

Cellular localization of the human Sef isoforms—To further test the possibility that hSef-b is an intracellular protein, transfected HEK 293 cells expressing each of the human Sef isoforms were subjected to immunofluorescence analysis. Detection was performed using antibodies directed against the myc epitope-tag fused to the hSef products or antibodies directed against the carboxyl-terminus of hSef proteins. As shown in FIGS. 3*a-d*, while hSef-a was localized to the cell surface (in agreement with prior art findings Tsang, M. et al., 2002) the hSef-b protein was detected in the cytosol of the transfected cell. These findings demonstrate that the hSef-b product is a cytosolic protein.

Altogether, these results demonstrate that the hSef gene undergoes alternative splicing which result in at least two distinct hSef isoforms (hSef-a and b). These results further show that while hSef-a is a heavily glycosylated, membrane protein, the hSef-b isoform apparently lacks any post-translational glycosylation modifications and is localized to the cytosol.

Example 2

The Expression of Human Sef Isoforms is Differentially Regulated

To further understand the role of the newly identified hSef-b isoform, the expression pattern and function of the hSef isoforms were determined, as follows.

Experimental Results

Tissue type specific expression of human Sef isoforms—The pattern of expression of hSef isoforms in a variety of human tissues and cell lines was examined by RT-PCR. Primers were designed to amplify a region common to both hSef transcripts or to specifically amplify each transcript. All 16 samples examined were positive for Sef transcripts when amplified with the primers from the common region of Sef isoforms (FIG. 4*a*). As is shown in FIG. 4*b*, hSef-a transcript was differentially expressed in 15 samples; HSef-a transcript was highly expressed in both fetal and adult brain, pituitary, tonsils, spleen, adenoids, fetal kidney, liver, testes and ovary, and moderate levels were detected in primary aortic endothelial cells, human umbilical vein endothelial cells (HUVEC) and adrenal medulla. As is further shown in FIG. 4*b*, low levels of hSef-a were observed in adrenal cortex, barely detected in placenta and completely absent in thyroid. In contrast, as is shown in FIG. 4*c*, hSef-b transcript was highly expressed in thyroid and testes; moderately expressed in pituitary, fetal brain and HUVEC cells; remaining tissues were either negative or expressed barely detectable levels of the hSef-b transcript. These findings demonstrate a unique expression pattern of hSef isoforms in a variety of tissues and suggest that the expression of the human Sef isoforms is regulated at the level of splicing or mRNA stability.

Example 3

Human Sef-B Isoform Inhibits Proliferation of NIH/3T3 Cells and Interferes with Human HEK 293 Cell Growth The different biochemical properties and subcellular localization of the two hSef isoforms raised the question whether hSef-b can inhibit FGF biological activity similar to hSef-a. NIH/3T3 cells were chosen to study the effect of hSef-b on biological responses to FGFs since they proliferate in response to various members of the FGF family, and have been extensively utilized as a model to study oncogenesis, regulation of cell proliferation and growth factor-mediated signaling. In addition, preliminary RT-PCR analyses revealed that NIH/3T3 cells express the mouse-Sef gene (data not shown). To study the effect of hSef-b on NIH/3T3 proliferation, cells were transfected with an expression vector containing the hSef-b coding sequence and the effect of hSef-b expression on colony number and proliferation was studied, as follows.

Experimental Results

Human Sef-b isoform reduces the number of NIH/3T3 colonies—The general effect of hSef-b on the growth of NIH/3T3 cells was studied as follows. Cells were stably transfected with either the pcDNA/hSef-b or an empty vector (i.e., a pcDNA without the hSef-b insert) and one day following transfection the cells were diluted (1:25) and were further cultured for 2-3 weeks in the presence of hygromycin B (marker selection), following which resistant colonies were counted. As is shown in Table 1, hereinbelow, a significant decrease (75%) in the number of colonies was observed in cells transfected with the hSef-b expression vector as compared with cells transfected with the empty vector.

TABLE 1

Number of colonies in cell stably transfected with hSef-b

| vector | No. of colonies | Ratio (%) |
|---|---|---|
| Empty vector | 110 | 100 |
| hSef-b | 28 | 25.9 |

Table 1: NIH 3T3 cells were stably transfected with either an expression vector (pCDNA3.1) containing the hSef-b coding sequence (SEQ ID NO: 4) or with the pCDNA3.1 vector alone (empty vector) and 2-3 weeks following transfection in the presence of the hygromycin B selection the number of colonies (five plates for each vector) was counted. Results represent the average of three independent experiments.

These results clearly demonstrate that similarly to hSef-a, hSef-b isoform inhibits NIH/3T3 cell growth.

Establishment of tet-off hSef-b NIH 3T3 cells lines—To understand the mechanisms leading to the inhibitory effect of hSef-b on the number of colonies of NIH 3T3 cells and to study the effect of hSef-b on FGF mediated signaling, NIH 3T3 stable cell lines in which the expression of hSef-b is regulated by tetracycline (tet) were established. S2 cells (NIH 3T3) were co-transfected with the pTet splice-hSef-b or an empty vector (i.e., the pTet splice alone, control cells) and the pTK-Hyg vector and were cultured for three weeks in the presence of hygromycin. Clones that did not express detectable levels of hSef-b in the presence of tetracycline were chosen for further analysis. Maximal level of hSef-b protein was obtained 16 hours following removal of tetracycline (FIG. 5, and data not shown).

Expression of hSef-b in NIH/3T3 cells does not affect the level of apoptosis—The inhibitory effect of hSef-b on colony formation could have resulted from either induction of apoptosis or inhibition of cell growth. The effect of hSef-b on apoptosis was tested using the TUNEL staining. Stable transfectants of hSef-b NIH 3T3 cells were grown for 48 hours in the presence or absence of tetracycline, or in the absence of tetracycline and serum, following which the cells were washed and fixed and were subjected to a TUNEL assay. As is shown in FIGS. 6*a-c*, while apoptotic cells were readily detected in NIH 3T3 cells grown in the absence of tetracycline and serum (FIG. 6*c*), no significant level of apoptosis was observed in NIH 3T3 grown in the presence (i.e., when hSef-b expression is downregulated) or absence (i.e., when hSef-b expression is upregulated) of tetracycline (FIGS. 6*a* and 6*b*, respectively).

Thus, these results demonstrate that over-expression of hSef-b in cells doesn't affect apoptotic processes in the cells.

Over-expression of human Sef-b affects the growth of human HEK 293 cells—When HEK 293 cells were transiently transfected with the hSef-b expression vector the morphology of the cells was changed (i.e., more round cells) and the cells came easily off the plate (data not shown). These results suggest that hSef-b affects the normal growth of human cells and likely causes cell death.

Human Sef-b inhibits NIH 3T3 growth via inhibition of the FGF2 mitogenic activity—To test the possibility that expression of hSef-b involves in FGF2 mitogenic activity, [$^3$H]-thymidine incorporation assays were employed. Confluent cultures of control or hSef-b-expressing cells were serum starved (for 24) and were grown in the presence or absence of tetracycline, following which the level of [$^3$H]-thymidine incorporation was measured in the presence of increasing concentrations of FGF2. As is shown in FIGS. 7*a-b*, while in control cells [$^3$H]-thymidine incorporation increased along with the increase of FGF2, in hSef-b-expressing cells, at 0.7 ng/ml FGF2, [$^3$H]-thymidine incorporation was reduced. These results demonstrate that over-expression of hSef-b strongly inhibits the mitogenic activity of FGF2.

Altogether, these findings indicate that hSef-b acts by restricting cell division and not by inducing apoptosis in NIH/3T3 cells.

Example 4

Human Sef-B Prevents Activation of Erk1/2 Map-Kinases

To further understand the mechanisms leading to hSef-b-mediated inhibition of cell growth the present inventor has studies the level of Cyclin-D1 which regulates S-phase entry (31), as well as the level of Erk1/2 MAP-kinases, pkB/Akt and p38 MAP-kinase, which are known to regulate cyclin D1 levels by transcriptional and post-translational mechanisms (31, 32). Erk1/2 MAP-kinases enhance Cyclin D1 expression and regulate the assembly of cyclin-CDK complex, whereas pkB/Akt regulates the turnover of cyclin D1 protein (31, 32). The p38 MAP-kinase can inhibit Cyclin D1 expression in a cell type dependent manner. p38 MAP-kinase has been generally associated with cellular response to stress, but several reports suggest its involvement in cellular responses to growth factors including FGF2 (22, 23).

Experimental Results

The hSef-b isoform reduces the level of cyclin D1—Sef-inducible cell lines were utilized to explore the mechanism underlying hSef-b inhibition of cell division. Cyclin D1 protein levels were evaluated at different time intervals post FGF2 growth-factor stimulation. As is shown in FIG. 8, while 20 hours following growth factor stimulation the cyclin D1 protein was readily observed in cells cultured in the presence of tetracycline, hSef-b-expressing cells failed to express cyclin D1. Since the levels of cyclin dependent kinase 4 (CDK4) do not fluctuate during the cell cycle (31), the level of CDK4 was examined as a probe for protein levels in each time point. CDK4 levels were similar in all time points in cultures grown in the presence or absence of tetracycline (FIG. 8). In addition, the levels of cyclin D1 remained unchanged in the control cells grown with or without tetracycline (data not shown).

Human Sef-b isoform prevents the activation of Erk1/2 MAP-kinases—Stimulation over time of control cells and hSef-b expressing cells revealed that hSef-b inhibited the activation of Erk1/2 MAP-kinases (phosphorylated Erk1/2) whereas total Erk1/2 levels remained unaltered (Compare P-Erk1/2 (activated) and Erk1/2 in FIGS. 9*a* and *b*). On the other hand, HSef-b had no effect on FGF2 induced activation of pkB/Akt or p38 MAP-kinase (FIG. 9*a*).

Expression of hSef-b does not affect MAP-kinase kinase level and state of activation—To further localize the site of hSef-b action, its effect on the activation of the dual specificity MAP-kinase kinase (MEK1/2), which phosphorylate Erk1/2 was examined in response to growth factor stimulation. As is shown in FIG. 9*a*, hSef-b had no effect on MEK1/2 activation in FGF2 stimulated cells, suggesting that the MAPK signaling pathway is blocked at the level or downstream of MEK.

The hSef-b protein associates with FGFR1—Prior studies utilizing co-immunoprecipitation assays demonstrated the association of the cell surface Sef isoform with several members of the FGFR family. Moreover, the site of interaction between the cell surface Sef and FGFR was mapped to the intracellular domain (8, 10, 13). Since as is shown in Example 1 hereinabove, the intracellular domain of hSef-a is shared in common with the hSef-b isoform, the ability of hSef-b to form a complex with FGFR1 was tested. To this end, HEK293 cells were transiently transfected with myc-tagged Sef constructs in the presence or absence of FGFR1. As shown in FIGS. 10*a-b*, FGFR1 co-immunoprecipitated with hSef-a in the absence of ligand stimulation, in agreement with published data (8, 10, 13). Human Sef-b, notwithstanding its lower expression levels compared to hSef-a, efficiently associated with FGFR1 but not with EGF receptor (FIGS. 10*a-b* and data not shown). These results lend further support to the importance of the C-terminal domain of Sef for the association with FGFRs.

Example 5 hSef-B Inhibits the Mitogenic Activity of FGF1, FGF2, FGF4, and PDGF

The subcellular localization of hSef-b may extend the repertoire of receptor tyrosine kinases (RTKs) that it can inhibit. To explore this hypothesis, the effect of hSef-b on mitogenic activity of additional members of the FGF family, as well as a subset of other RTK ligands, and serum was examined, as follows.

Experimental Results

A dose response curve was performed for each ligand, and representative results are shown in FIGS. 11*a-b*. In addition to FGF2, hSef-b inhibited the mitogenic activity of FGF1 and FGF4 (80% inhibition of FGF2, and 60% inhibition of FGF1 or FGF4) as well as the activity of platelet derived growth factor (PDGF) (40, 57 and 68% inhibition at 2.5, 5 and 10 ng/ml ligand, respectively). These results are in contrast the lack of effect of Sef-a on PDGF signaling (10). Inhibition of PDGF was accompanied with reduction in the activation of Erk1/2 MAPK (FIG. 12). By contrast, hSef-b had little or no effect on the activity of serum, insulin or EGF (FIG. 11*b*). The mitogenic activity of serum and each of the other growth factors was similar in control cultures grown in the presence or absence of tetracycline (FIG. 11*a*).

Example 6

Identification of Additional Human Sef Splice Forms: hSef-C and hSef-D

Experimental Results

Identification of additional alternative spliced forms of hSef—Using the RACE protocol the present inventor has identified two additional human Sef isoforms from normal human ovary RNA. FIGS. 13*a* and 14*a* depict the nucleic acid sequences of hSef-c and hSef-d RACE products, respectively. The predicted amino acid sequences are shown in FIGS. 13*b* and 14*b*, for hSef-c and hSef-d, respectively. First strand was using the primer set forth by SEQ ID NO:1, and amplification was performed using the primers set forth by SEQ ID NOs:19 and 3 (for hSef-c) or SEQ ID NOs:21 and 3 (for hSef-d), RT-PCR fragments of approximately 2.2 kb each were identified (data not shown), indicating that the hSef-c and hSef-d are alternative splice forms of the hSef gene. These results suggest the identification of the entire coding region of each isoform. Both isoforms exhibit sequences which are common with the other hSef isoforms (i.e., hSef-a and hSef-b), these include amino acids 50-77 in SEQ ID NO:15 (hSef-c) and amino acids 71-115 in SEQ ID NO:14 (hSef-d). Noteworthy, that while amino acids 21-98 of SEQ ID NO:14 were predicted from the experimentally identified RACE product, the rest of the sequence set forth in SEQ ID NO:14 was predicted using the EST clone (GenBank Accession No. BG149830).

Prediction of open reading frame within the new hSef isoforms—In the coding sequence of human Sef-c isoform there are three potential initiation codons (methionine residues, labeled with a green M in FIG. 13*b*), and further experiments (e.g., using Edman degradation or Mass Spectrometry) are expected to reveal the active translation initiator. On the other hand, in hSef-d, the predicted initiation codon is the Methionine residue at position 57 of SEQ ID NO:14.

Differential expression of hSef-c in breast and ovary—RT-PCR analysis using primers specific to hSef-c (SEQ ID NOs: 19 and 20) revealed differential expression of this isoform; hSef-c is highly expressed in breast and ovary tissues, moderately expressed in brain and to a much lesser extent in fetal kidney (data not shown).

Analysis and Discussion

The results presented in Examples 1-6, hereinabove, indicate that different hSef isoforms are generated via an alternative splicing mechanism. One isoform, hSef-a, is similar to the previously reported Sef from zebrafish and mammals (7-9, 13). This isoform is thought to encode a type I transmembrane protein, and immunofluorescence staining confirmed that hSef-a product is located at the cell surface. On the other hand, in the novel isoform, hSef-b, the leader sequence and the next 8 residues of hSef-a were replaced with 10 different residues. This isoform lacks a signal for secretion and immunofluorescence staining revealed that it is a cytosolic protein. Furthermore, the hSef-b product does not undergo significant post-translational modification, a property that is typical for proteins that are translated in the cytosolic compartment. Collectively these results demonstrate that alternative splicing differentially influences the subcellular localization of hSef isoforms.

Besides lacking a signal for secretion, the alternate sequence contained a CUG initiation codon instead of the conventional AUG initiation codon. Initiation from this CUG codon is consistent with the apparent molecular weight of both the in vitro and in vivo expressed hSef-b. The utilization of CUG as a translation start site may be responsible for the observed differences in the expression levels of hSef-a and hSef-b products, as non-AUG codons direct less efficient translation initiation (34, 35).

The hSef-b isoform exhibits a restricted pattern of expression compared to hSef-a. It is highly expressed in testes and thyroid and to a much lesser extent in tissues of neuronal origin and primary endothelial cells whereas hSef-a transcript is expressed in all the tissues and primary cells that were examined except for the thyroid. Interestingly, the expression profile of hSef-a parallels that of FGFRs (19, 20, 36-38) suggesting that this isoform regulates a wide array of biological processes where FGFs are implicated. The high levels of hSef-b in thyroid and testes could imply that this isoform regulates unique biological processes and may be more specific to cells of epithelial origin. With respect to FGFs, it may control signaling by specific receptor isoforms. Therefore, an important avenue of future research would be to determine how each Sef isoform affects signaling by the distinct FGFRs.

Human Sef-b inhibited mitogenic response of NIH/3T3 cells to several members of the FGF family, but not to serum, insulin or EGF. Unlike the cell surface Sef (10), hSef-b inhibited PDGF-induced mitogenic response suggesting that intracellular machinery, common to signaling by FGF and PDGF, is affected. Consistent with this is the finding that hSef-b inhibited the Ras/MAPK pathway and reduced cyclin D1 levels. However, hSef-b does not globally affect RTK-induced signaling pathways since it had no effect on FGF induction of the PI 3-kinase or the p38 MAPK pathway, which is consistent with hSef-b action downstream of Ras. Lack of an effect on the PI 3-kinase pathway also correlates with the finding that hSef-b inhibited cell growth but did not lead to an increase in apoptosis. The inhibition of the MAPK pathway and maintenance of PI 3-kinase pathway may allow cells expressing hSef-b to cease proliferation but remain viable upon growth factor stimulation.

Altogether these results restrict hSef-b activity to a narrow window at the level of, or down stream from MEK. Similar to the hSef-a isoform [(8, 10, 13), and present data], the hSef-b isoform can associate with FGFR1 in co-immunoprecipitation assays. Since, unlike hSef-a, the hSef-b isoform is cytosolic, its association with the receptor could function as a mean to bring hSef-b in the vicinity of the components of the Ras/MAPK pathway. Although both isoforms interact with FGFR1, the outcome of this association is not identical because the cell surface Sef isoform inhibits multiple FGF-signaling pathways [(10), and data not shown]. As the entire hSef-b isoform is located inside the cells, its folding must be quite different from that of the hSef-a isoform, and is likely to influence its mode of action. For example, the amino-terminal domain of hSef-b, which also contains the unique hSef-b residues, can interact with proteins in the signaling cascade whereas in hSef-a, this domain is extracellular and is not required for inhibitory activity (8, 10, 13). Alternatively, it could function as an autoregulatory domain that prevents hSef-b from interacting with certain proteins in the signaling cascade. Studies are in progress to address these questions.

Example 7

Human Sef-B Induces Efficient Colony Suppression and Inhibits Growth of Breast Cancer Cell Lines Materials and Experimental Methods Cell Culture, transfection methods and colony suppression assay—Human cell lines MDA-MB-435, HeLa, and human embryonic kidney, HEK 293, were maintained in Dulbecco's modified Eagle's medium (DMEM) supplemented with 10% fetal bovine serum (FCS). For transfection, cells from sub-confluent cultures were plated at a density of $2\times10^6$ cells per 60 mm plate, and 24 hours later, were transfected with either the hSef-a [pcDNA3.1/hSef-a (SEQ ID NO:10), containing the hygromycin selection marker], the hSef-b [pcDNA3.1/myc-His/hSef-b (SEQ ID NO:4), containing the neomycin selection marker] or the hSef-c [pcDNA3.1/hSef-c (SEQ ID NO:8)] expression vectors (5 μg DNA per plate). An empty pcDNA3.1 vector was used as control. Transfection was performed with DreamFect reagent according to the manufacturer's instructions (OZ Biosciences). Six to eight hours post transfection, the medium was replaced with fresh DMEM containing 10% FCS. The following day, cultures were trypsinized and plated at various dilutions (e.g., 1:5 and 1:10). Selection was carried out with complete medium containing 1 mg/ml G418 or 150 μg/ml hygromycin (depending on the plasmid used). Colonies of resistant cells were counted at the end of the selection process 1-2 weeks post transfection.

Experimental Results

Overexpression (ectopic expression) of hSef-a, hSef-b or hSef-c results in suppression of colony formation and reduced cell growth of MDA-MB 435 breast cancer cells—To ascertain the biological effect of hSef expression in human cancer cells, a colony suppression assay was employed. The breast cancer cell line MDA-MB-435, extensively used for studying breast cancer biology (Sellappan, S., Grijalva, R., Zhou, X., Yang, W., Eli, M. B., Mills, G. B. and Yu, D. Lineage infidelity of MDA-MB-435 cells: expression of melanocyte proteins in a breast cancer cell line, Cancer Res., 64: 3479-3485, 2004), was transfected with either hSef-a, hSef-b or hSef-c expression vectors and colonies were counted 1-2 weeks following marker selection. Cells transfected with hSef-a, hSef-b or hSef-c expression vector formed about 94-95% less colonies as compared with cells transfected with control empty vector (Table 2, hereinbelow). It is noteworthy, that while the majority (over 95%) of resistant colonies transfected with the control empty vector were dense, the colonies formed following transfection with the hSef-b, hSef-a or hSef-c were very sparse, small, made of few cells, grew extremely slowly, and the majority did not survive trypsinization and plating.

TABLE 2

| Number of colonies in cell stably transfected with hSef-a, hSef-b, hSef-c or empty vector | | |
|---|---|---|
| Vector | No. of colonies | Ratio (%) |
| Empty vector | 250 | 100 |
| hSef-a | 15 | 6 |
| hSef-b | 12 | 5 |
| hSef-c | 12 | 5 |

Table 2: MDA-MB 435 cells were stably transfected with expression vector bearing hSef-a (pCDNA/hSef-a), hSef-b (pCDNA/hSef-b), hSef-c (pCDNA3.1/hSef-c) or an empty vector (pCDNA). After one day, cells were diluted and marker-selected for 1-2 weeks. Resistant clones were counted at the end of the selection process (3 plates for each vector). The results are representative of 3 different experiments, and show the average number of colonies/plate.

Altogether, these results clearly demonstrate that overexpression of hSef-a, hSef-b or hSef-c results in a significant inhibition of cancerous colony formation and cancerous cell growth.

Example 8

Downregulation of Sef Expression Correlates with Increased Malignancy of Solid Tumors As described in Example 2, hereinabove, hSef is highly expressed in the epithelial cells of normal breast, prostate and the thyroid glands as well as the ovarian surface. To further substantiate the role of hSef in the initiation and/or progression of solid tumors, the present inventor has further investigated the expression of Sef in normal epithelial tissues and cancer derived from these tissues.

Materials and Experimental Methods

Enzymes, Reagents, Chemicals, and expression vectors—Restriction enzymes were from NEB, Pharmacia and Roche. Blocking reagent, Digoxigenin (DIG)-RNA Labeling Kit, 5-Bromo-4-chloro-3-indolyl-phosphate, 4-toluidine salt, Nitroblue tetrazolium chloride, maleic acid, T7 RNA Polymerase, Proteinase K, Yeast tRNA and Anti-digoxigenin [Fab] conjugated to alkaline phosphatase were from Roche. M-MLV Reverse Transcriptase and random hexamer primers were from GIBCO BRL. Mounting solution was from Southern Biotech, BSA from ICN, and all other chemicals were from Sigma. Expression plasmids containing the hSef-a or hSef-b coding region were generated as described in the "General Marterials and Experimental Methods" of the Examples section, hereinabove. The different hSef cDNA isoforms (hSef-a or hSef-b) were cloned into pcDNA3.1, or pcDNA3.1/myc-H is expression vectors (Invitrogen) containing the hygromycin or neomycin selection marker, respectively.

RNA extraction and RT-PCR—For detection of hSef transcripts in normal breast tissues, total RNA was extracted from human breast tissues, as described (Eisemann, A., et al., Oncogene, 6: 1195-1202, 1991; Preger, E., et al., Proc Natl. Acad. Sci. U.S.A, 101: 1229-1234, 2004). Half microgram (0.5 μg) of total RNA was used for first-strand synthesis with random hexamer primers. The PCR was performed with a primer common to both hSef isoforms (5'-TGAAGCTACT-GTTGAGCTGCTTCG-3' SEQ ID NO:17) and a primer specific for each isoform. (hSef-a; 5'-GAGGATCCTGACGGC-CATGGCCCCGTGGCTGCAGCT-3' SEQ ID NO:16 or hSef-b; 5'-GCGTGCCAGACAGAGTGCTAGGCAT-3' SEQ ID NO:2). Amplification was carried out in 25 μl using standard conditions of 1 μM primers, using Redimix (ABgene), for 32 cycles at 95° C. for 30 seconds, 64° C. for 30 seconds and 72° C. for 1 minute. For detection of hSef RNA in HeLa cells, 1 μg of total RNA was used for first strand synthesis, and amplification was carried out with primers common to hSef isoforms as previously described (Preger et al., PNAS 2004, Supra). GAPDH amplification was carried out for monitoring RNA quantity and amplification efficiency.

Tissue microarrays, tissue sections, and in situ hybridization—Tissue microarrays containing 1.5 mm cores of normal and cancer tissues were purchased from Cybrdi, Gaithersburg, Md. The microarray contained breast cancer specimens from 62 different cases, 53 ovarian cancer specimens, 33 prostate cancer specimens in duplicate, or 16 thyroid carcinoma specimens in triplicate. Morphology of each tissue was confirmed by hematoxylin & Eosin staining. All samples were pathologically confirmed prior to hybridization by the manufacturer, and following in-situ hybridization by two experienced pathologists. Formalin fixed, paraffin embedded sections of breast and prostate tumors as well as normal breast, ovary, and thyroid tissues were obtained from the Departments of Pathology, Rambam Medical Center, (Haifa, Israel), and the Bnai Zion Medical Center, (Haifa, Israel). Grading of breast and thyroid cancers was according to the World Health Organization criteria (for breast: Tavassoli F A, Devilee P. eds In: World Health Organization classification of tumours. Pathology and Genetics of Tumors of the breast, and female genital organs. Lyon: IARC Press; 2003. p. 18-19; for thyroid: DeLellis R A, Llowd R V, Heitz P U, Emg C eds. In: World Health Organization classification of tumours. Pathology and genetics of tumors of endocrine organs. Lyon:IARC press; 2004. p. 64); ovarian carcinomas were graded according to the International Federation of Gynecology and Obstetrics (FIGO) grading system, and prostate cancer grading was according the Gleason grading system (for prostate: Maygarden, S. J. and Pruthi, R. Gleason grading and volume estimation in prostate needle biopsy specimens: evolving issues, Am. J. Clin. Pathol., 123 Suppl:S58-66.: S58-S66, 2005; for ovarian: Kosary, C. L. FIGO stage, histology, histologic grade, age and race as prognostic factors in determining survival for cancers of the female gynecological system: an analysis of 1973-87 SEER cases of cancers of the endometrium, cervix, ovary, vulva, and vagina, Semin. Surg. Oncol., 10: 31-46, 1994). RNA in-situ hybridization was carried out as previously described (Sher, I., et al., Targeting perlecan in human keratinocytes reveals novel roles for perlecan in epidermal formation, J. Biol. Chem., 281: 5178-

5187, 2005). For probe preparation, a cDNA fragment spanning nucleotides 1606-2208 from the hSef common region (accession # AY489047) and cloned in both orientations, relative to the T7 RNA polymerase promoter, into pBluescript II plasmid (Stratagene). Digoxigenin-labeled (DIG) antisense and sense riboprobes were synthesized by using T7 RNA polymerase according to the manufacturer's protocol. Probe preparation, sectioning, pretreatment of the sections, and hybridization of the probes were done under strict RNase-free conditions, using reagents supplied by Roche Applied Science. All reagents were prepared using diethyl pyrocarbonate-treated distilled water. Sections (5 μm thick) were incubated overnight at 45° C. in the prehybridization solution containing 0.5 μg/ml of DIG-labeled RNA probe, for the breast, prostate and thyroid sections, and 1 μg/ml for the ovary sections. The detection of the hybridized probes was carried out using anti-DIG antibodies alkaline phosphatase-conjugated (antibodies dilution 1/2500) in 4° C. for 16 hours. The signal was detected using the NBT/BCIP substrates. Where indicated, sections were counterstained with Mayer's hematoxylin. Hybridization with the sense probe used as hybridization specificity control and did not result in detectable signal. Slides were analyzed with a Nikon eclipse E400 microscope. Staining intensity was semiquantitatively classified as very strong (typical for normal epithelium), strong (few tumors with ~50-75% staining intensity of normal epithelium), moderate (~25-50% intensity of normal epithelium), weak (<25% of normal epithelium) and negative (<5% of normal epithelium). Statistical significance of associations between tumor grade and hSef expression was determined by Chi square test.

Experimental Results

Expression of hSef-a, but not hSef-b, in normal human breast tissues—To determine whether hSef is expressed in normal mammary epithelium, and to find out which of the hSef isoforms is expressed in breast tissues, initial RT-PCR analysis was employed. The analysis was performed with RNA extracted from different healthy donors using primer sets that specifically detect the hSef-a or the hSef-b isoforms. As is shown in FIG. 15*a*, hSef-a but not hSef-b, is expressed in normal human breast. In situ analysis with probe common to the different hSef isoforms revealed in normal human breast tissue very strong hSef signal in the ductal and lobular epithelial cells (Ep) and a weaker signal in stromal fibroblasts (F) and endothelial cells (FIGS. 15*b-c*). hSef transcripts were not detected in vascular smooth muscle cells (Vsm), myoepithelial cells (My) and adipose tissue (Ad) (Data not shown). A sense probe failed to generate a signal (data not shown) confirming specificity of hSef transcript detection.

The expression of hSef is downregulated in invasive breast cancer—The expression of hSef in 68 carcinoma cases and 2 benign lesions was surveyed by RNA in situ hybridization. Two of 68 cases were classified as well-differentiated non-invasive carcinoma (grade I), and 66/68 cases as invasive carcinoma (6, 43, and 17 grade I, II, and III, respectively). Representative illustrations and a summary of hSef expression levels in the different cancer types are shown in FIGS. 15*d-i* and Table 3, respectively. Ductal epithelial cells of benign lesions and non-invasive carcinoma exhibited high hSef expression levels close to the very strong staining of normal mammary epithelial cells (FIG. 15*d* and data not shown). In contrast, striking reduction in hSef expression was observed in the invasive carcinoma cases: 7/66 tumors expressed uniformly weak hSef levels (FIG. 15*f*), 3/66 displayed heterogeneous expression pattern (FIG. 15*e*), and 56/66 tumors were negative (FIGS. 15*g-i*). The 3 tumors with heterogenous expression, diagnosed as grade I well differentiated invasive carcinoma, displayed a mixed morphology with more than 85% solid growth pattern, and less than 15% ductal architecture. Strong hSef expression was observed in only a small fraction of the cancerous ducts whereas the rest of the tumor was negative or expressed low hSef levels (FIG. 15*e*). The negative cases were 1/6 grade I, 40/43 grade II, and 15/17 grade III (see Table 3, hereinbelow). These results, therefore, indicate a strong association between loss of hSef expression and breast cancer invasion.

TABLE 3

Summary of hSef expression in breast carcinomas

| Histological type | N | Expression Level: Very Strong | Low | Negative |
|---|---|---|---|---|
| Non - invasive carcinoma (DCIS low grade) | 2 | 2 | | |
| Invasive carcinoma/grade I | 6 | | 5[a] | 1 |
| grade II | 43 | | 3 | 40 |
| grade III | 17 | | 2 | 15 |
| Number of cases examined | 68 (100%) | 2 (3%) | 10 (14%) | 56 (83%) |

Table 3- hSef expression levels in breast carcinomas according to tumor grade. Expression levels in tumors were compared to those observed in normal ductal epithelial cells (8 cases). Signal intensity score was determined as described under the Materials and Experimental Methods.

[a]denotes heterogeneous staining observed in 3 tumor samples diagnosed as grade I well differentiated invasive carcinoma. In these tumors hSef signal was low in about 75-90% of the tumor cells, and moderate to strong in about 10-25% tumor cells where ductal architecture was still apparent (see FIGS. 17a-j). Examples for the different staining intensities are shown in FIGS. 15b-i.

Down regulation of hSef expression is common to a variety of human epithelial tumors—To determine whether the profound reduction in hSef expression during breast cancer invasion is organ-specific or common to epithelial carcinogenesis in vivo, the present inventor has expanded the analysis comparing hSef expression in normal tissues and malignancies of the ovary, prostate and thyroid gland. Representative expression analysis by RNA in situ hybridization is illustrated in FIGS. 16*a-f* (ovary), 17*a-f* (thyroid) and 18*a-f* (prostate) and comprehensive results of hSef expression levels in various cancer types are summarized in Table 4, hereinbelow.

As shown in FIGS. 16*a-b*, hSef transcript levels were high in ovarian surface epithelium (OSE) and epithelium of the fallopian tube (FT) (4 cases). This was consistent with detection of hSef-a expression in normal human ovary using RT-PCR (Preger, E., et al., Proc Natl. Acad. Sci. U.S.A, 101: 1229-1234, 2004). For comparison of hSef expression in epithelial ovarian cancer (EOC), 43 primary ovarian epithelial tumors and 10 secondary ovarian malignancies were analyzed. EOC is the sixth most common cancer in women and the most frequent cancer-related cause of death from gynecologic tumors (Jemal, A., et al., Cancer statistics, 2006, CA Cancer J. Clin., 56: 106-130, 2006; Bell, D. A. Origins and molecular pathology of ovarian cancer, Mod. Pathol., 18 Suppl 2:S19-32.: S19-S32, 2005). Ninety-five percent of EOC originate from the ovarian surface epithelium (OSE), where high hSef levels were detected, and ~5% of EOC represent metastases from other organ sites (Bell, D. A., 2005, Supra; Kaku, T., et al., Med. Electron Microsc., 36: 9-17, 2003). Thirty-two primary EOC represented serous carcinomas, the most common ovarian malignancy (Jemal, A., 2006, Supra; Bell, D. A. 2005, Supra). The remaining 11 primary tumors were EOC of lower incidence including mucinous, endometrioid, clear cell and undifferentiated tumors. The group of primary EOC comprised 12% (5/43 cases) grade I, 35% (15/43) grade II, and 53% (23/43) grade III tumors. Secondary malignancies included metastases from the GI tract and breast (9 and 1 case, respectively). hSef was clearly down-regulated in 95% of primary EOCs exhibiting low expression in 17/43 cases and was undetectable in 19/43 cases (FIGS. 16*e-f* and Table 4). In the remaining 7/43 cases, moderate hSef expression was observed in 5 (3 cases of grade II and 2 of grade III) and strong expression in 2 low grade tumors (FIGS. 16*c-d*). Among the metastatic tumors to the ovary, nine out of ten cases were negative, and 1 case expressed low hSef levels (Table 4). These findings clearly indicate that hSef expression was also down-regulated in tumors of the ovary.

Thyroid carcinoma is the most common malignancy of the endocrine system, and the majority of tumors originate from the follicular cells of the thyroid gland (DeLellis R A, Llowd R V, Heitz P U, Emg C. (ed). World Health Organization classification of tumours. Pathology and genetics of tumors of endocrine organs, IARC press: Lyon, 2004; Hundahl, S. A., Fleming, I. D., Fremgen, A. M. and Menck, H. R. A National Cancer Data Base report on 53,856 cases of thyroid carcinoma treated in the U.S., 1985-1995, Cancer., 83: 2638-2648, 1998). As shown in FIGS. 17*a-b*, a very strong hSef signal was observed in the follicular cells of normal thyroid (n=3) confirming detection of hSef by RT-PCR (Preger, E., 2004, Supra). Sixteen thyroid malignancies screened for hSef expression included 8 papillary and 8 follicular carcinomas (summarized in Table 4). These tumor types arise from the follicular cells of the thyroid gland where hSef transcripts are expressed physiologically. Papillary carcinoma is a slow growing cancer, accounting for 70-80% of all thyroid cancers. Follicular carcinoma is generally considered more aggressive than papillary carcinoma and accounts for about 15% of thyroid gland tumors (Gimm, O. Thyroid cancer, Cancer Lett., 163: 143-156, 2001). hSef transcripts were absent in 75% of the tumors (5/8 papillary, 7/8 follicular, FIGS. 17*e-f*). The staining intensity in the remaining 4 cases, which were from low grade tumors, was strong in 3 (2 papillary and 1 follicular carcinoma) and moderate in the forth case [(papillary carcinoma), FIGS. 17*c-d*]. These results demonstrate a marked reduction of hSef expression in thyroid carcinomas.

Prostate cancer is the most common visceral cancer and the second leading cause of cancer-related death in men (Jemal, A., 2006, Supra; Hughes, C., et al., J. Clin. Pathol., 58: 673-684, 2005). To assess hSef expression in prostate tumors, 31 primary prostatic adenocarcinomas, 5 cases of benign prostate hyperplasia (BPH), as well as 4 examples of morphologically normal prostate tissue were screened. Grading of cancer specimen is listed in Table 4, including 4 low grade [Gleason Grade (GG) 6], 10 intermediate grade (GG7) and 17 high-grade (GG8-10) tumors. Representative results shown in FIGS. 18*a-f* indicated that hSef is highly expressed in the glandular epithelium, and to a much lesser extent in stromal cells, of the normal prostate gland (FIG. 18*a*). Its expression in the glandular epithelium of 4/5 BPH cases was markedly decreased (FIG. 18*b*), and was lost in the fifth BPH case. In 77.5% of the prostate cancer cases hSef expression was either lost (16/31 cases, FIGS. 18*c, e-f*) or was markedly reduced (8/31 cases, FIG. 18*d*). Only 3 of these 24 cases were from low grade tumors. Moderate hSef levels were observed in only 2 tumor samples of low and an intermediate grade, respectively. In the remaining tumor cases (5/31) hSef signal was heterogeneous. While part of the tumor was negative other parts revealed moderate or low expression (FIG. 18*c* and Table 4). These observations indicated that a fraction of prostate malignancies harbored higher hSef expression levels than BPH. Furthermore, they showed that hSef expression is down-regulated in a significant fraction of prostate cancers.

TABLE 4

Summary of hSef expression in ovarian carcinomas, thyroid tumors and prostate tumors

| Histological type | N | Strong (%) | Moderate | Low | Negative | Heteroa |
|---|---|---|---|---|---|---|
| | Expression Level | | | | | |
| Ovarian Tumors | | | | | | |
| Serous papillary adenocarcinoma/grade I | 4 | 1 | | 3 | | |
| grade II | 11 | | 3 | 4 | 4 | |
| grade III | 17 | | 1 | 5 | 11 | |
| Others(a) | 11 | 1 | 1 | 5 | 4 | |
| Summary of primary ovarian tumors | 43 (100%) | 2 (5%) | 5 (12%) | 17 (38%) | 19 (45%) | |
| Metastasis from other organs | 10 (100%) | | | 1 (10%) | 9 (90%) | |
| Thyroid Tumors | | | | | | |
| Papillary carcinoma | 8 | 2 | 1 | | 5 | |
| Follicular carcinoma | 8 | 1 | | | 7 | |
| Summary of carcinoma cases | 16 (100%) | 3 (19%) | 1 (6%) | | 12 (75%) | |
| Prostate Tumors | | | | | | |
| BPH | 5 | | | 4 | 1 | |
| Prostatic adenocarcinoma | | | | | | |
| /G6 | 4 | | | 2 | 1 | 1 |
| /G7 | 10 | | 2 | 2 | 5 | 1 |

TABLE 4-continued

Summary of hSef expression in ovarian carcinomas, thyroid tumors and prostate tumors

| Histological type | N | Expression Level Strong (%) | Moderate | Low | Negative | Heteroa |
|---|---|---|---|---|---|---|
| /G8-10 | 17 | | | 4 | 10 | 3 |
| Summary of adenocarcinoma cases | 31 (100%) | | 2 (6%) | 8 (26%) | 16 (52%) | 5 (16%) |

Table 4 - Summary of hSef expression levels in ovarian, prostate and thyroid tumors. Expression levels in the tumors were compared to hSef expression in the epithelial cells of the corresponding normal tissues which was scored very strong. For ovarian tumors levels are relative to those observed in the in normal OSE and fallopian tube epithelium (3 cases). For thyroid, relative to expression in follicular cells (3 cases), and for prostate relative to the level observed in morphologically normal glandular epithelium (4 cases). Signal intensity score was determined as described under Materials and Methods. The secondary ovarian tumor positive for hSef expression was a Krukenberg tumor (1/6 cases). The remaining secondary tumors were 3 colon and 1 breast carcinoma cases. Other ovarian tumors (a) include low grade transitional cell (1 case), and endometrioid (1) carcinoma, and high grade mucinous (3), squamous (1), clear cell (2), un-differentiated (2), and small cell (1) carcinoma.

hSef is downregulated in four carcinoma types—A summary of hSef levels in the primary tumors is shown in Table 5, hereinbelow. Down regulation was observed in 95% (151/158) of these tumors. In 65% of the cases hSef signal was absent or extremely low, and in 22% of the cases hSef signal was weak. The remaining 8% of the cases displayed 3-5 fold reduced hSef signal. Of the negative cases, 98% were from intermediate and high-grade tumors. The cases where hSef signal was relatively strong (5%), were from low grade tumors. The marked down regulation of hSef expression in the four carcinoma types, suggest that loss of hSef expression may be a common theme in human carcinomas.

TABLE 5

| Expression level | Carcinoma grade Low (%) N = 22 | Intermediate (%) N = 75 | High (%) N = 61 | Total cases (%) N = 158 |
|---|---|---|---|---|
| strong | 7 (32) | none | none | N = 7 (5) |
| moderate | 3 (14) | 6 (8) | 4 (7) | N = 13 (8) |
| low | 10 (45) | 9 (12) | 16 (26) | N = 35 (22) |
| Negative | 2 (9) | 60 (80) | 41 (67) | N = 103 (65) |

Table 5 - Summary of hSef expression levels in the various human primary carcinoma types according to tumor grade. Low grade includes all tumors that were classified as grade I carcinoma and prostate adenocarcinoma GG6. Intermediate grade includes all tumors classified as grade II, 7/8 cases follicular carcinoma of the thyroid, and prostate adenocarcinoma GG7. High grade includes all grade III carcinomas, and prostatic adenocarcinoma GG8-10. Prostatic carcinoma cases with heterogeneous expression pattern were included in the moderate expression level group. Chi square test indicated that association of hSef down-regulation and tumor progression was statistically significant ($p \leqq 0.001$).

Example 9

Inhibition of Human Sef by RNA Interference Facilitates the Growth of Cervical Carcinoma As is shown in Table 2 and is described in Example 7, hereinabove, cells transfected with the hSef-a or the hSef-b expression vector formed 95% less colonies relative to empty control vector. In addition, as is shown in FIGS. 15-18 and is described in Example 8, hereinabove, the expression level of hSef is downregulated in a variety of human carcinomas as compared with the high expression in the corresponding normal epithelial cells. These results strongly suggest a role for hSef in constraining proliferation. Thus, it is expected that suppression of endogenous hSef expression would accelerate tumor cell growth. To test this hypothesis, the present inventor has employed the RNAi approach, as follows.

Materials and Experimental Methods

Generation of hSef silencing constructs—The Whitehead siRNA Selection Web Server and Oligoengine shockwave program were employed for prediction of homologous hSef-a RNA oligonucleotides (19 nucleotides). Three test sequences and one control sequence were designed as follows: shRNA 1, forward, 5'-GTCGGAGGGAAGACAGTGC (SEQ ID NO:23); reverse, 5'-GCACTGTCTTCCCTCCGAC (SEQ ID NO:24); shRNA 2, forward, 5'-GCATGTGATTGCTGACGCC (SEQ ID NO:25); reverse, 5'-GGCGTCAGCAATCACATGC (SEQ ID NO:26). shRNA 3, forward, 5'-AGCAGGAGCAAACTACAGA (SEQ ID NO:27); reverse, 5'-TCTGTAGTTTGCTCCTGCT (SEQ ID NO:28). Control, forward, 5'-CGTGACAGAAGGGAGGCTG (SEQ ID NO:29); reverse, 5'-CAGCCTCCCTTCTGTCACG (SEQ ID NO:30). shRNA 1 in reverse orientation was used as control. The 3' and 5' end of the oligonucleotide primers were adapted for cloning into the BglII and HindIII sites of pSUPER. To generate shRNAs, equimolar amounts of complementary sense and antisense strands were mixed, annealed and ligated into pSUPER digested with BglII/HindIII. Positive clones were sequenced to ensure accuracy of RNAi.

Cell Culture, transfection methods and colony suppression assay—as described in Example 7, hereinabove.

RNA interference—For hSef RNA interference, the efficiency of hSef silencing was initially tested by co-transfecting an hSef expression vector individually with each shRNA construct into HEK-293 cells, using previously described transfection protocol (Preger, 2004, Supra). Each Sef shRNA, but not the control shRNA or empty pSUPER vector, reduced hSef protein levels when compared to cells transfected with hSef construct alone (data not shown). Subconfluent cultures of HeLa cells were then transfected with each shRNA vector, a combination of the three hSef shRNA constructs (1.5 μg each) or the control shRNA construct, together with pcDNA 3.1 (for selection). Following selection with 0.5 mg/ml G418, mass cultures were tested for the reduction of endogenous hSef RNA. The most efficient reduction was observed with cells transfected with the combination of constructs. These cells were subsequently used for future studies.

Proliferation assay—The assay was performed as previously described (Shaoul, E., et al., Oncogene, 10: 1553-1561, 1995). Briefly, Hela cells stably expressing hSef sh-RNA or control sh-RNA were seeded into 24 well microtiter plates ($2.5\times10^4$ cells/well) in DMEM containing 10% FCS. The following day, cells were washed 3 times with DMEM, and grown in DMEM alone or in the presence of desired concentrations of growth factors. Fresh growth factors were added every other day, and viable cells were counted on day 5 of incubation. Each data point was performed in duplicates or triplicates and each experiment was repeated at least 3 times.

Experimental Results

Downregulation of hSef enhances proliferation of HeLa cervical carcinoma cells—The pSUPER system for RNA interference was utilized to stably express hSef sh-RNA in HeLa cervical carcinoma cells. RT-PCR analysis demonstrated that hSef RNA levels were substantially reduced in cells stably expressing hSef sh-RNA, but not in cells expressing the control sh-RNA (FIG. 19*a*). Proliferation rate of the transfected cells in serum free conditions (SFM) or in the presence of EGF (20 ng/ml) or FGF1 (10 or 20 ng/ml), was determined. The results clearly demonstrate that hSef silencing enhances proliferation of HeLa cells by 2-4 folds in serum-free conditions, and following exogenous ligand stimulation (FIG. 19*b*). These results establish that endogenous hSef exerts a growth constraining effect that is removed upon hSef downregulation in tumor cells.

Analysis and Discussion

Subversion of physiological RTK signaling is a common mechanism by which cancer cells gain uncontrolled growth potential (Blume-Jensen, P. and Hunter, T. Oncogenic kinase signalling, Nature., 411: 355-365, 2001) Although there is extensive evidence implicating oncogenic RTK activation by overexpression, mutation and autocrine ligand expression in human cancer, less is known about abrogation of negative regulatory constraints resulting in chronic activation of RTK-mediated signaling pathways. Sef is a novel inhibitor of RTK-mediated signaling whose role in the neoplastic process has not been established. The results described in Examples 7-9 hereinabove provide the first comprehensive expression analysis of hSef in different human carcinoma types of high incidence, as well as functional studies that clearly indicate a role for hSef in the neoplastic process. These findings demonstrate that hSef is highly expressed in epithelial cells of normal human breast, ovary, thyroid and prostate glands. In striking contrast, hSef expression was significantly down-regulated in 95% of malignancies originating from these epithelia overall. A tumor-specific decrease comprised loss of hSef expression in 65% and substantial reduction in additional 22% of tumors. Among the remaining tumors, 8% showed moderate reduction in hSef expression, and merely 5% displayed a strong hSef signal approaching expression levels of normal epithelium. The small subset of tumors displaying strong hSef expression was exclusively from low-grade tumors, accounting for only one third of tumors of this grade (7/21 cases). In contrast, 98% of malignancies devoid of hSef expression were intermediate or high-grade tumors (summary in Table 5, hereinabove). The marked down-regulation of hSef expression in all four carcinoma types implies that loss of hSef expression may be a common mechanism in human epithelial neoplasia. Moreover, association of hSef loss of expression with tumor grade indicates that hSef down-regulation relates to the aggressiveness of the tumor cell in vivo.

The extent of hSef loss of expression varied among the different tumor types studied. Accordingly, hSef loss of expression was observed in 83% of breast carcinoma, while 75% of a smaller cohort of thyroid tumors lacked hSef expression.

By comparison, the percentage of ovarian and prostate malignancies devoid of hSef expression was 45% and 52%, respectively. The different cancer types varied also with respect to kinetics of hSef loss of expression during tumor progression. In ovary, 36% intermediate grade and 50% high grade primary ovarian carcinomas lost hSef expression. In prostate cancer 50% of intermediate grade and 59% of high grade tumors did not express hSef in agreement with Darby et al., (Darby, S., et al., Oncogene., 25:4122-7, 2006). In contrast, in breast and thyroid carcinomas the majority of intermediate grade tumors were already negative for hSef expression (93%, and 100%, respectively). These observed variations in the extent and kinetics of hSef loss of expression during tumor progression may reflect differences in organ or tissue specific mechanisms utilized for silencing hSef expression.

The current study provided compelling evidence that hSef may function as a tumor suppressor. First, hSef transcripts are highly expressed in the normal epithelium of the four tissue types analyzed. Second, significant down-regulation of hSef expression occurred in primary carcinomas derived from these epithelial tissues. Third, overexpression of either hSef isoform in human breast cancer cells inhibited colony formation. Finally, lowering hSef expression in cervical carcinoma cells by RNA interference significantly augmented their proliferation rate in response to EGF and FGF. These results combined with the known capacity of mammalian Sefs to inhibit two major pathways for transduction of oncogenic signals including RAS/MAPK and PI 3-K (Preger, E., 2004, Supra; Xiong, S., et al., J Biol. Chem., 278:50273-50282, 2003; Torii, S., et al., Dev. Cell, 7: 33-44, 2004; Yang, X., et al., J. Biol. Chem., 279: 38099-38102, 2004; Ziv, I., et al., Human Sef-a isoform utilizes different mechanisms to regulate FGFR signaling pathways and subsequent cell fate. In: Anonymous 2006; Kovalenko, D., et al., J. Biol. Chem., 278: 14087-14091, 2003), strongly support a role for hSef in negatively regulating cellular growth and clearly indicate a role for hSef loss of function in the neoplastic process.

A characteristic of feedback antagonists of RTK signaling involves induction of expression by the same pathway they inhibit (Niehrs, C. and Meinhardt, H. Modular feedback, Nature, 417: 35-36, 2002). Consistently, induction of Sef expression by FGFs in zebrafish or chick embryos (Tsang, M., et al., Nat. Cell Biol., 4: 165-169, 2002; Furthauer, M., et al., Nat. Cell Biol., 4: 170-174, 2002; Harduf, H., et al., Dev. Dyn., 233: 301-312, 2005). In addition, both EGF and FGFs induced hSef expression in vitro (unpublished results). The current findings revealed downregulation of hSef expression in malignancies in which expression of various ligands and receptors of the EGF and FGF families is known to be elevated (Normanno, N., et al., Curr. Drug Targets., 6: 243-257, 2005; Furthauer, M., et al., Nat. Cell Biol., 4: 170-174, 2002; Steele, I. A., et al., Oncogene., 20: 5878-5887, 2001). Therefore, specific mechanisms must prevent induction of hSef by these growth factor/RTK pathways in cancer cells. Such mechanisms may involve transcriptional repression, decreased RNA stability, DNA methylation or deletion. The hSef gene maps to chromosome 3p14, where defined genetic and epigenetic alterations have been identified in a number of human malignancies, including lung and breast cancer (Matsumoto, S., et al., Genes Chromosomes. Cancer., 20: 268-274, 1997; Kovacs, G., et al., Int. J. Cancer, 43: 422-427, 1989; Pathak, S., et al., Science, 217: 939-941, 1982). In this context, it is noteworthy that we have identified two CpG islands that overlap with the first exon of hSef-a and hSef-b (unpublished observation), raising the possibility that hSef methylation may be one mechanism involved in loss of hSef expression in human carcinomas.

In summary, these results strongly indicate that hSef down-regulation might be a general characteristic of human cancer and suggest a role for hSef loss of function in the neoplastic process. Further insights into the mechanism(s) underlying hSef loss of expression in human malignancy would not only advance the understanding of tumor pathogenesis, but also facilitate the design of novel therapeutic strategies based on upregulating hSef in human carcinomas.

Example 10

Administration of a Human Sef Upregulating Agent to Animal Models Induced to Bear Cancerous Tumors To test the effect of upregulation of Sef on the inhibition of solid tumor growth in vivo, the present inventor has designed the following experimental approaches.

Tumor formation in transgenic mice overexpressing an oncogene—A transgenic mouse model for cancer (e.g., breast cancer) such as the erb model (Shah N., et al., 1999, Cancer Lett. 146: 15-2; Weistein E J., et al., 2000, Mol. Med. 6: 4-16) or MTV/myc model (Stewart T A et al., 1984, Cell, 38: 627-637), the c-myc model (Leder A., et al., 1986, Cell, 45:485-495), v-Ha-ras or c-neu model (Elson A and Leder P, 1995, J. Biol. Chem. 270: 26116-22) can be used to test the ability of hSef to suppress tumor growth in vivo.

Tumor formation in mice administered with cancerous cell lines—For the formation of solid tumors, athymic mice can be injected with human or animal (e.g., mouse) cancerous cells such as those derived from breast cancer, ovarian cancer, prostrate cancer or thyroid cancer, and following the formation of cancerous tumors the mice can be subjected to intratumor and/or systemic administration of an agent capable of upregulating hSef expression level and/or activity (e.g., by overexpression of hSef).

The following cell lines (provided with their ATCC Accession numbers) can be used for each type of cancer model:

For Breast Cancer:

Human breast cancer cell lines—MDA-MB-453 (ATCC No. HTB-131), MDA-MB-231 (ATCC No. HTB-26), BT474 (ATCC No. HTB-20), MCF-7 (ATCC No. HTB-22), MDA-MB-468, (for additional cell lines see Hypertext Transfer Protocol://World Wide Web(dot)path(dot)cam(dot)ac(dot)uk/~pawefish/index (dot)html);

For Ovarian Cancer:

Human ovarian cancer cell lines—SKOV3 (ATCC No. HTB-77), OVCAR-3 HTB-161), OVCAR-4, OVCAR-5, OVCAR-8 and IGROV1;

For Prostate Cancer:

Human prostate cancer cell lines~DU-145 (ATCC No. HTB-81), PC-3 (ATCC No. CRL-1435);

For Thyroid Cancer:

Human derived thyroid cancer cell lines—FTC-133, K1, K2, NPA87, K5, WRO82-1, ARO89-1, DRO81-1;

For Lung Cancer:

Mouse lung carcinoma LL/2 (LLC1) cells (Lewis lung carcinoma)—These cells are derived from a mouse bearing a tumor resulting from an implantation of primary Lewis lung carcinoma. The cells are tumorigenic in C57BL mice, express H-2b antigen and are widely used as a model for metastasis and for studying the mechanisms of cancer chemotherapeutic agents (Bertram J S, et al., 1980, Cancer Lett. 11: 63-73; Sharma S, et al. 1999, J. Immunol. 163: 5020-5028).

For Melanoma:

Mouse B16-F10 cells (Melanoma)—The cells are derived from mouse (C57BL/6J) bearing melanoma (Briles E B, et al., 1978, J. Natl. Cancer Inst. 60: 1217-1222).

Culturing conditions of cancerous cells—The cancerous cells can be cultured in a tissue culture medium such as the DMEM with 4 mM L-glutamine adjusted to contain 1.5 g/L sodium bicarbonate and 4.5 g/L glucose, supplemented with 10% fetal calf serum (FCS), according to known procedures (e.g., as described in the ATCC protocols).

Tumor formation in animal models by administration of cancerous cells—Athymic nu/nu mice (e.g., female mice) can be purchased from the Jackson Laboratory (Bar Harbor, Me.). Tumors can be formed by subcutaneous (s.c.) injection of cancerous cells (e.g., $2\times10^6$ cells in 100 μl of PBS per mouse). Tumors are then allowed to grow in vivo for several days (e.g., 6-14 days) until they reach a detectable size of about 0.5 cm in diameter. It will be appreciated that injection of cancerous cells to an animal model can be at the organ from which the cell line is derived (e.g., mammary tissue for breast cancer, ovary for ovarian cancer) or can be injected at an irrelevant tissue such as the rear leg of the mouse.

Modes of administration of hSef—To test the effect of hSef on inhibition of tumor growth, hSef is administered to the animal model bearing the tumor either locally at the site of tumor or systemically, by intravenous injection of infusion, via, e.g., the tail vein. The time of Sef administration may vary from immediately following injection of the cancerous cell line (e.g., by systemic administration) or at predetermined time periods following the appearance of the solid tumor (e.g., to the site of tumor formation, every 3 days for 3-10 times as described in Ugen K E et al., Cancer Gene Ther. 2006 Jun. 9; [Epub ahead of print]).

Ectopic expression (overexpression) of hSef in solid tumors—Administration of hSef can be effected using a nucleic acid construct designed to express hSef coding sequence (e.g., a viral vector), naked pDNA and/or hSef liposomes, as follows.

Viral vectors—Overexpression of hSef can be effected using viral expression vectors as described hereinabove [e.g., the recombinant adeno-associated virus 2 (AAV) as described in Mahendra, 2005 (Supra), SV40-based as described in Kimchi-Sarfaty C, and Gottesman M M, 2004, Curr. Pharm. Biotechnol. 5: 451-8; retroviruses such as Molony murine leukemia virus (Mo-MuLV); and lentiviruses (Amado R G, Chen I S., 1999, Science. 285: 674-6]. Briefly, null adenovirus (i.e., an adenovirus vector lacking an insert) or adenovirus expressing either hSef-a (SEQ ID NO:10) or hSef-b (SEQ ID NO:4) or hSef-c (SEQ ID NO:8) can be amplified and titered in host cells (e.g., bone marrow cells derived from the animal) which are further administered back to the animal (i.e., ex vivo gene therapy) essentially as described elsewhere (He L., Yu J. X., et al., Cancer Res., 58: 4238-4244, 1998). Alternatively, the adenovirus vector expressing hSef-a or hSef-b can be administered directly to the individual (e.g., animal model) using systemic or local modes of administrations (i.e., in vivo gene therapy).

Adenovirus preparations of about $8\times10^{10}$ particles of virus/dose of the null, hSef-a or hSef-b coding sequences are administered intratumoral or peritumoral in a volume of about 100 μl. PBS is injected as a negative control. Doses can be every other day for total of four doses to mice bearing tumors. For further details see Guang-Liang Jiang and Shi Huang, 2001, Cancer Research 61: 1796-1798.

Liposome delivery system—Liposomes can be used for in vivo delivery of hSef polynucleotides to target cells. For example, the cationic lipid formulation 3 beta [N—(N',N'-Dimethylaminoethane)-Carbamoyl] Cholesterol (DC-Chol) is a non-viral delivery agent which can be used to target of hSef into cells of interest (e.g., cancerous cells). For example, allogeneic and xenogeneic MHC DNA-liposome complexes were successfully employed in a phase I study of immunotherapy of cutaneous metastases of human carcinoma using the DC-Chol/DOPE cationic liposomes (see for example, Hui K M, Ang P T, Huang L, Tay S K., 1997, Gene Ther. 1997, 4(8):783-90; Serikawa T., et al., 2006, Journal of Controlled Release, 2006 Apr. 26; [Epub ahead of print]).

The hSef liposomes can be administered directly into the tumor cells or can be administered intravenously and be directed to the cells-of-interest using a cell specific recognition moiety such as a ligand, antibody or receptor capable of specifically binding to the cell-of-interest. For example, in order to direct the hSef-liposomes to cancerous cells of an epithelial origin (e.g., breast cancer cells), the liposomes can include a ligand that can specifically recognize the cancerous cells due to overexpression of the receptor for this specific ligand. For example, one such ligand can be the keratinocyte growth factor (KGF or FGF7) molecule which is specific for cells of epithelial origin. Thus, KGF can be directed to tumors such as endometrial carcinoma or pancreatic carcinoma where the KGF receptor is overexpressed (Visco, V., et al., 1999, Expression of keratinocyte growth factor receptor compared with that of epidermal growth factor receptor and erbB-2 in endometrial adenocarcinoma, Int. J. Oncol., 15: 431-435; Siegfried, S., et al., 1997, Distinct patterns of expression of keratinocyte growth factor and its receptor in endometrial carcinoma, Cancer, 79: 1166-1171). Similarly other ligands such as EGF can be used to target lyposomes into tumors where the EGF receptor is overexpressed such as glyomas and endometrial carcinomas (for a review see: Normanno, N., et al., 2005, The ErbB receptors and their ligands in cancer: an overview, Curr. Drug Targets. 6:243-257). It should be noted, that since malignant cells of epithelial origin overexpress the KGF receptor, they are more susceptible to hSef-liposome treatment than other non-malignant cells. To this end, the present inventor has prepared KGF which can be attached to the liposomes.

Additionally or alternatively, targeting of the liposome to specific cells can be performed by antibodies essentially as described in Dass C R. and Choong P F, J Control Release. 2006 May 9; [Epub ahead of print]. For example, a single chain FV antibody, against the KGF receptor can be used to target the hSef liposome to cancerous cells of epithelial origin.

Naked nucleic acids—Naked DNA [e.g., naked plasmid DNA (pDNA)] is an attractive simple, non-viral vector which can easily be produced in bacteria and manipulated using standard recombinant DNA techniques. It does not induce antibody response against itself (i.e., no anti-DNA antibodies generated) and enables long-term gene expression even without chromosome integration. Naked hSef DNA can be introduced by intravascular and electroporation techniques as described in Wolff J A, Budker V, 2005, Adv. Genet. 54: 3-20. Alternatively, naked hSef DNA can be administered locally (intratumorally) followed by eletroporation as described for the DNA plasmid expressing interleukin-15 (pIL-15) which was administered into melanoma tumors in mice and induced complete tumor regression in 37% of the treated mice [Ugen KE, 2006 (Supra)]. Still alternatively, naked hSef DNA can be administered in vivo by jet injection essentially as described in Walther W, et al., 2004, Mol. Biotechnol. 28: 121-8. Still alternatively, naked hSef DNA can be administered into epidermis cells via DNA-coated gold particles as described in Dean H J, 2005, Expert Opin Drug Deliv. 2: 227-36. Still alternatively, naked hSef DNA can be administered to cancerous cells via cavitation bubbles which induce transient membrane permeabilization (sonoporation) on a single cell level [using low frequency sonication (kilohertz frequencies), lithotripter shockwaves, HIFU, and even diagnostic ultrasound (megahertz frequencies)]. Cavitation initiation and control can be enhanced by cavitation nucleation agents, such as an ultrasound contrast agent [for further details see Miller D L, et al., 2002, Somat Cell Mol. Genet. 27:115-34; using e.g., the Sonitron 2000 sonoporation system (Sonidel Limited, Dublin, Republic Ireland).

Evaluation of solid tumor inhibition—Tumor sizes are measured two to three times a week. Tumor volumes are calculated using the length and width of the tumor (in millimeters). The effect of hSef treatment can be evaluated by comparing the tumor volume using statistical analyses such as Student's t test. In addition, histological analyses can be performed using markers typical for each type of cancer.

Altogether, once the tumors are formed, the agent capable of upregulating hSef expression level and/or activity is administered to the individual in need thereof, e.g., the animal model bearing the tumor, either locally or systemically, and the effect of the agent on tumor growth is detected using methods known in the art.

Example 11

Formation of an Animal Model with Conditional Upregulation of Sef

To test the ability of hSef to inhibit the growth of solid tumor, a conditioned animal model in which Sef expression is upregulated in a spatial and a temporal manner following or concomitant with tumor formation can be utilized. Mice with conditioned expression of Sef can be subjected to in vivo formation of tumors by overexpression of an oncogene at the tissue-of-choice where Sef is expressed or by subjecting the tissue-of-choice to carcinogenic agents, as follows.

Animal model with a spatial and a temporal expression of hSef can be used to inhibit tumor growth by upregulation of Sef—A transgenic mouse model where hSef is specifically expressed in a certain tissue (e.g., breast or skin) and switches on hSef expression at specific times during tumor growth can be designed. Temporal expression of Sef can be achieved by a vector for conditioned expression such the Tet-off/Tet-On expression systems (Clontech Laboratories, Inc). For example, when the Tet-Off expression system is used, hSef expression (preferably in a specific tissue) is upregulated in the absence of tetracycline (doxycycline). On the other hand, hSef expression (in the specific tissue) can initiate following the appearance of a tumor in a transgenic mouse expressing erb and transfected with a Tet-On expression system. In this mouse, once the breast cancer tumors are detectable (e.g., using ultrasound), the mouse can be treated with tetracycline which activates the expression of hSef-Tet-On expression system. Overexpression of hSef will therefore result in inhibiting tumor growth and treatment of cancer.

Generation of a mouse model with spatial and a temporal expression of Sef in which an oncogen is expressed in a tissue specific manner—To generate a mouse model in which hSef expression is not only conditioned but also tissue specific, the tet system can be used, as follows. The tTA (tet transactivator) expression is controlled under a tissue specific promoter. For this purpose a transgenic mouse is generated in which the expression of hSef is under the control of the tTa. Then another mouse model is generated, in which the oncogene—of choice (e.g., erb) that create tumors is chosen such that it induces the tumors in one of the sites of interest (e.g., breast, skin). This mouse is then mated with the first mouse where Sef-tTa expression is under the control of a tissue-specific promoter and kept under conditions that hSef expression is silenced. At different time intervals during tumor development, hSef can be switched on, and then, the effect of its expression can be tested. It is expected that that hSef will suppress or even completely eradicate the tumor.

Generation of a mouse model with spatial and a temporal expression of Sef in which tumors are formed due to exposure to carcinogens—A transgenic hSef mouse under the control of tTa is mated with a mouse of choice where the tTa itself is preferably tissue specific. This mouse will be grown under conditions that silence hSef. Such a mouse will be treated with carcinogens to develop tumors in specific sites [e.g., dimethyl benzanthracene (DMBA) and tetradecanoyl-phorbol acetate (TPA) for skin tumors (Hecker E. Toxicol Pathol. 1987; 15(2):245-58)]. hSef expression will be switched on at different time intervals during tumor progression and the effect of this expression can be followed. It is expected that hSef will be able to suppress tumor growth pr to eradicate it.

For further description of animal models using conditioned expression of the gene-of-interest (e.g., Sef) see Takashi M., et al., 2004, Mol. Carcinogenesis. 40: 189-200; Gunther E J., et al., 2002, FASEB, 16: 283-292; Miyazaki S., et al., 2005, Biochem. Biophys. Res. Commun., 338: 1083-8; Kistner A., et al., 1996, Proc. Natl. Acad. Sci. 93: 10933-10938; which are incorporated herein by references.

Altogether, the experimental approaches described in Examples 10 and 11, hereinabove can be used to test the ability of the Sef upregulating agents of the present invention in inhibiting the growth of solid tumor in vivo.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Schlessinger, J. (2000) *Cell* 103, 211-225.
2. Pawson, T. & Saxton, T. M. (1999) *Cell* 97, 675-678.
3. Simon, M. A. (2000) *Cell* 103, 13-15.
4. Hunter, T. (2000) *Cell* 100, 113-127.
5. Christofori, G. (2003) *Nat. Cell Biol.* 5, 377-379.
6. Dikic, I. & Giordano, S. (2003) *Curr. Opin. Cell Biol.* 15, 128-135.
7. Furthauer, M., Lin, W., Ang, S. L., Thisse, B. & Thisse, C. (2002) *Nat. Cell Biol.* 4, 170-174.
8. Tsang, M., Friesel, R., Kudoh, T. & Dawid, I. B. (2002) *Nat. Cell Biol.* 4, 165-169.
9. Lin, W., Furthauer, M., Thisse, B., Thisse, C., Jing, N. & Ang, S. L. (2002) *Mech. Dev.* 113, 163-168.
10. Kovalenko, D., Yang, X., Nadeau, R. J., Harkins, L. K. & Friesel, R. (2003) *J. Biol. Chem.* 278, 14087-14091.
11. Krasilnikov, M. A. (2000) *Biochemistry* (*Mosc.*) 65, 59-67.
12. Scheid, M. P. & Woodgett, J. R. (2001) *Nat. Rev. Mol. Cell. Biol.* 2, 760-768.
13. Yang, R. B., Ng, C. K., Wasserman, S. M., Komuves, L. G., Gerritsen, M. E. & Topper, J. N. (2003) *J. Biol. Chem.* (on-line)
14. Klint, P. & Claesson-Welsh, L. (1999) *Front. Biosci.* 4:D165-77, D165-77.
15. Powers, C. J., McLeskey, S. W. & Wellstein, A. (2000) *Endocr. Relat Cancer* 7, 165-197.
16. Ornitz, D. M. & Itoh, N. (2001) *Genome Biol.* 2, REVIEWS 3005.
17. McKeehan, W. L., Wang, F. & Kan, M. (1998) *Prog. Nucleic. Acid. Res. Mol. Biol.* 59, 135-176.
18. Miki, T., Fleming, T. P., Bottaro, D. P., Rubin, J. S., Ron, D. & Aaronson, S. A. (1991) *Science* 251, 72-75.
19. Eisemann, A., Ahn, J. A., Graziani, G., Tronick, S. R. & Ron, D. (1991) *Oncogene* 6, 1195-1202.
20. Ron, D., Reich, R., Chedid, M., Lengel, C., Cohen, O. E., Chan, A. M., Neufeld, G., Miki, T. & Tronick, S. R. (1993) *J. Biol. Chem.* 268, 5388-5394.
21. Ong, S. H., Hadari, Y. R., Gotoh, N., Guy, G. R., Schlessinger, J. & Lax, I. (2001) *Proc. Natl. Acad. Sci. U.S.A.* 98, 6074-6079.
22. Maher, P. (1999) *J. Biol. Chem.* 274, 17491-17498.
23. Boilly, B., Vercoutter-Edouart, A. S., Hondermarck, H., Nurcombe, V. & Le, B., X (2000) *Cytokine Growth Factor Rev.* 11, 295-302.
24. Reich-Slotky, R., Shaoul, E., Berman, B., Graziani, G. & Ron, D. (1995) *J. Biol. Chem.* 270, 29813-29818.
25. Ron, D., Bottaro, D. P., Finch, P. W., Morris, D., Rubin, J. S. & Aaronson, S. A. (1993) *J. Biol. Chem.* 268, 2984-2988.
26. Sher, I., Weizman, A., Lubinsky-Mink, S., Lang, T., Adir, N., Schomburg, D. & Ron, D. (1999) *J. Biol. Chem.* 274, 35016-35022.
27. Ron, D., Tronick, S. R., Aaronson, S. A. & Eva, A. (1988) *EMBO J.* 7, 2465-2473.
28. Shockett, P., Difilippantonio, M., Hellman, N. & Schatz, D. G. (1995) *Proc. Natl. Acad. Sci. U.S.A.* 92, 6522-6526.
29. Studier, F. W., Rosenberg, A. H., Dunn, J. J. & Dubendorff, J. W. (1990) *Methods Enzymol.* 185, 60-89.
30. Shaoul, E., Reich-Slotky, R., Berman, B. & Ron, D. (1995) *Oncogene* 10, 1553-1561.
31. Sherr, C. J. & Roberts, J. M. (1999) *Genes Dev.* 13, 1501-1512.
32. Lavoie, J. N., L'Allemain, G., Brunet, A., Muller, R. & Pouyssegur, J. (1996) *J. Biol. Chem.* 271, 20608-20616.
33. Niehrs, C. & Meinhardt, H. (2002) *Nature* 417, 35-36.
34. Kozak, M. (1989) *Mol. Cell. Biol.* 9, 5073-5080.
35. Kozak, M. (1991) *J. Biol. Chem.* 266, 19867-19870.
36. Miki, T., Bottaro, D. P., Fleming, T. P., Smith, C. L., Burgess, W. H., Chan, A. M. & Aaronson, S. A. (1992) *Proc. Natl. Acad. Sci. U.S.A.* 89, 246-250.
37. Finch, P. W., Cunha, G. R., Rubin, J. S., Wong, J. & Ron, D. (1995) *Dev. Dyn.* 203, 223-240.
38. Yazaki, N., Hosoi, Y., Kawabata, K., Miyake, A., Minami, M., Satoh, M., Ohta, M., Kawasaki, T. & Itoh, N. (1994) *J. Neurosci. Res.* 37, 445-452.
39. Darby S, et al., Oncogene. 2006 Feb. 13; [Epub ahead of print] Loss of Sef (similar expression to FGF) expression is associated with high grade and metastatic prostate cancer.

What is claimed is:

1. A method of diagnosing thyroid cancer or prostate cancer in a subject in need thereof, the method comprising:

(a) detecting in a thyroid or prostate tissue sample of the subject, respectively an expression level of a Sef polynucleotide which is hybridizable to SEQ ID NO:31, wherein a decrease in said expression level of said Sef polynucleotide in said tissue sample as compared to said expression level of said Sef polynucleotide in a corresponding unaffected or normal tissue is indicative of the presence of the thyroid or prostate cancer, respectively; and (b) determining a malignancy of said cancer based on said decrease in said expression level, wherein a reduced expression of said Sef polynucleotide in said thyroid or prostate tissue sample correlates with an increase in said malignancy of the thyroid or prostate cancer, respectively, and (c) classifying patients with reduced expression of said Sef polynucleotide in said prostate tissue or in said thyroid tissue as having prostate cancer or thyroid cancer, respectively, thereby diagnosing the thyroid cancer or prostate cancer, respectively, in the subject in need thereof.

2. The method of claim 1, wherein said detecting is effected by an RNA detection method.

3. The method of claim 2, wherein said RNA detection method is selected from the group consisting of RNA in situ hybridization, RT-PCR, in situ RT-PCR and Northern blot analysis.

4. The method of claim 1, wherein said cancer is a primary solid tumor.

5. A method of selecting a treatment regimen for a subject having thyroid carcinoma or prostate cancer, the method comprising:

(a) detecting in a thyroid or prostate tissue sample of the subject, respectively an expression level of a Sef polynucleotide which is hybridizable to SEQ ID NO:31, wherein a decrease in said expression level of said Sef polynucleotide in said tissue sample as compared to said expression level of said Sef polynucleotide in a corresponding unaffected or normal tissue is indicative of the presence or malignancy of the thyroid or prostate cancer, respectively; and (b) classifying patients with reduced expression of said Sef polynucleotide in said prostate tissue or in said thyroid tissue as having prostate cancer or thyroid cancer, respectively, and (c) selecting an anti-cancer therapy regimen based on said presence or said malignancy of the thyroid or prostate cancer, respectively, thereby selecting the treatment regiment for the subject.

6. A method of diagnosing thyroid carcinoma or prostate cancer in a subject in need thereof, the method comprising:

(a) determining a presence of a cancer diagnostic marker in a thyroid or prostate tissue sample of the subject, respectively, and;

(b) detecting in said thyroid or prostate tissue sample an expression level of a Sef polynucleotide which is hybridizable to SEQ ID NO:31, and (c) classifying patients with reduced expression of said Sef polynucleotide in said prostate tissue or in said thyroid tissue as having prostate cancer or thyroid cancer, respectively, wherein said decrease in said expression level of said Sef correlates with an increased malignancy and/or aggressiveness of said thyroid or prostate cancer, respectively, thereby diagnosing the thyroid carcinoma or prostate cancer, respectively, in the subject in need thereof.

7. The method of claim 6, further comprising selecting a treatment regimen based on said diagnosis.

8. The method of claim 1, further comprising selecting a treatment regimen based on said diagnosing.

9. A method of determining a prognosis of a subject having cancerous solid tumor selected from the group consisting of thyroid carcinoma and prostate cancer, comprising:

(a) selecting a subject diagnosed with the cancerous solid tumor, and;

(b) detecting in a sample of the cancerous solid tumor an expression level of a Sef polynucleotide which is hybridizable to SEQ ID NO:31, wherein a complete loss of said expression level of said Sef polynucleotide in said sample is indicative of a poor prognosis, and (c) classifying patients with said complete loss of expression level of said Sef polynucleotide in said prostate tissue or in said thyroid tissue as having poor prognosis, respectively, thereby determining the prognosis of the subject having cancerous solid tumor.

10. The method of claim 9, wherein said poor prognosis is associated with a malignant, aggressive and/or metastatic cancer.

11. A method of selecting a treatment regimen for a subject having a skin cancer, the method comprising:

(a) detecting in a skin cancer tissue sample of the subject, an expression level of a Sef polynucleotide which is hybridizable to SEQ ID NO:31, wherein a decrease in said expression level of said Sef polynucleotide in said skin cancer tissue sample as compared to said expression level of said Sef polynucleotide in a corresponding unaffected or normal tissue is indicative of the presence of the skin cancer; and (b) selecting an anti-cancer therapy regimen based on said presence of the skin cancer, thereby selecting the treatment regiment for the subject.

12. The method of claim 11, wherein said skin cancer is melanoma.

13. A method of diagnosing skin cancer in a subject in need thereof, the method comprising:

(a) determining a presence of a cancer diagnostic marker in a skin tissue sample of the subject, respectively, and;

(b) detecting in said skin tissue sample an expression level of a Sef polynucleotide which is hybridizable to SEQ ID NO:31, wherein said presence of said cancer diagnostic marker in said tissue in combination with a decrease in said expression level of said Sef polynucleotide in said tissue sample as compared to said expression level of said Sef polynucleotide in a corresponding unaffected or normal tissue is indicative of a diagnosis of the cancer, (c) classifying patients with reduced expression of said Sef polynucleotide in said skin tissue as having skin cancer, thereby diagnosing the skin cancer, respectively, in the subject in need thereof.

14. The method of claim 13, further comprising selecting a treatment regimen based on said diagnosing.

* * * * *